(12) United States Patent
Iketaki et al.

(10) Patent No.: US 6,844,963 B2
(45) Date of Patent: *Jan. 18, 2005

(54) DOUBLE-RESONANCE-ABSORPTION MICROSCOPE

(75) Inventors: Yoshinori Iketaki, Tokyo (JP); Mashaaki Fujii, Aichi (JP); Takeshige Omatsu, Kanagawa (JP); Osamu Sato, Kanagawa (JP); Kimiyoshi Yamamoto, Tokyo (JP)

(73) Assignees: Olympus Optical Co., Ltd., Tokyo (JP); Japan Science and Technology Agency, Saitama Prefecture (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/814,125

(22) Filed: Mar. 22, 2001

(65) Prior Publication Data

US 2001/0045529 A1 Nov. 29, 2001

(30) Foreign Application Priority Data

Mar. 23, 2000 (JP) ....................................... 2000-082890
Mar. 23, 2000 (JP) ....................................... 2000-082893
Mar. 23, 2000 (JP) ....................................... 2000-082898
Mar. 23, 2000 (JP) ....................................... 2000-082930
Mar. 23, 2000 (JP) ....................................... 2000-085368

(51) Int. Cl.[7] ............................. G02B 21/00; G01J 3/30
(52) U.S. Cl. ....................... 359/368; 359/385; 356/311; 356/318; 250/458.1
(58) Field of Search ................................. 359/368, 370, 359/385, 352, 355, 386; 250/458.1, 203.3; 356/311, 318, 301

(56) References Cited

U.S. PATENT DOCUMENTS 5,783,814 A * 7/1998 Fairley et al. ............ 250/201.3
5,835,262 A * 11/1998 Iketaki et al. ................ 359/352
6,184,535 B1 * 2/2001 Kashima et al. .......... 250/459.1
6,667,830 B1 * 12/2003 Iketaki et al. ................ 359/368

* cited by examiner

*Primary Examiner*—Audrey Chang
(74) *Attorney, Agent, or Firm*—Wenderoth, Lind & Ponack L.L.P.

(57) ABSTRACT

The present invention provides various embodiments of a double-resonance-absorption microscope which realizes a super-resolution by using double resonance absorption. In particular, a double-resonance-absorption microscope includes a light source for a pump light of a wavelength $\lambda_1$ which excites a sample molecule to a first electronic excited state from a ground state, a light source for an erase light of a wavelength $\lambda_2$ which excites the sample molecule to a second electronic excited state or a higher excited state from the first electronic excited state, and an overlap component for partially overlapping irradiating areas of the pump light and the erase light with each other. An emission area upon deexcitation of the sample molecule to the ground state from the first electronic excited state is partially inhibited by irradiating the pump light and the erase light through the overlap means. On an optical path of the erase light, a spatial filter is provided which has a condenser lens, a collimate lens, and a pinhole therebetween, and performs condensing of the erase light onto the pinhole by the condenser lens and collimating of the erase light passed through the pinhole into a parallel beam by the collimate lens.

22 Claims, 64 Drawing Sheets

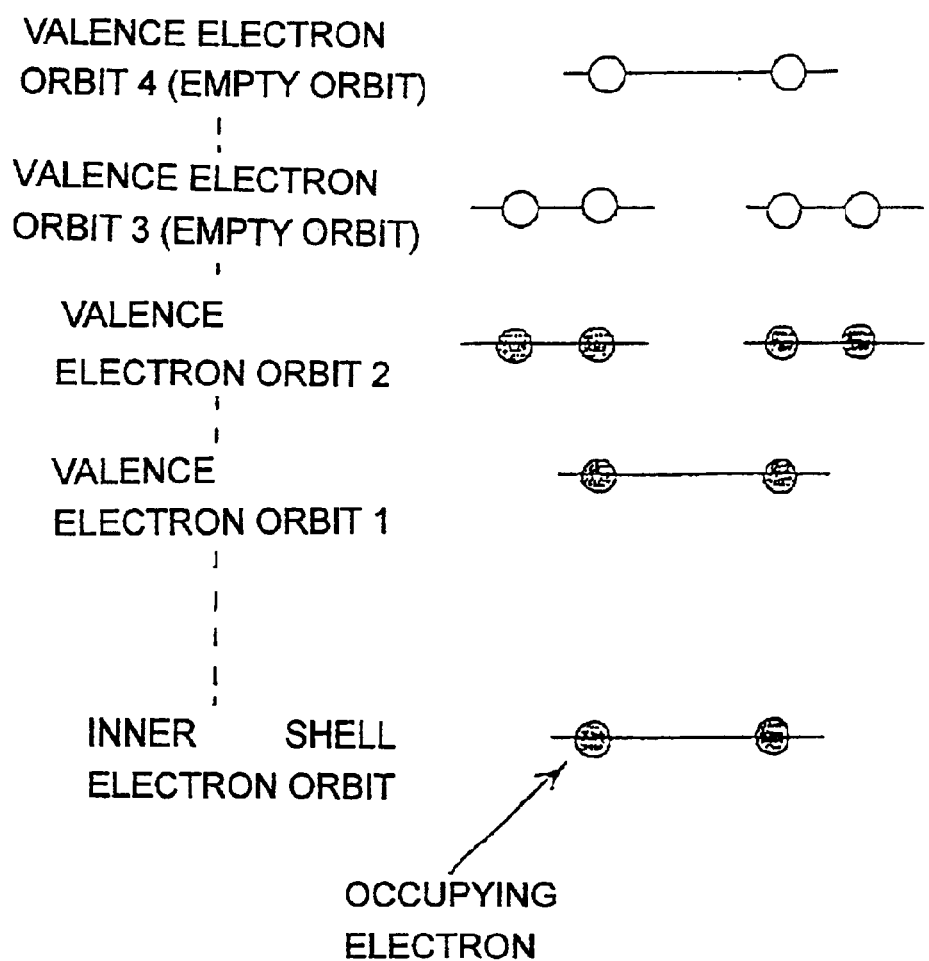
F I G. 1

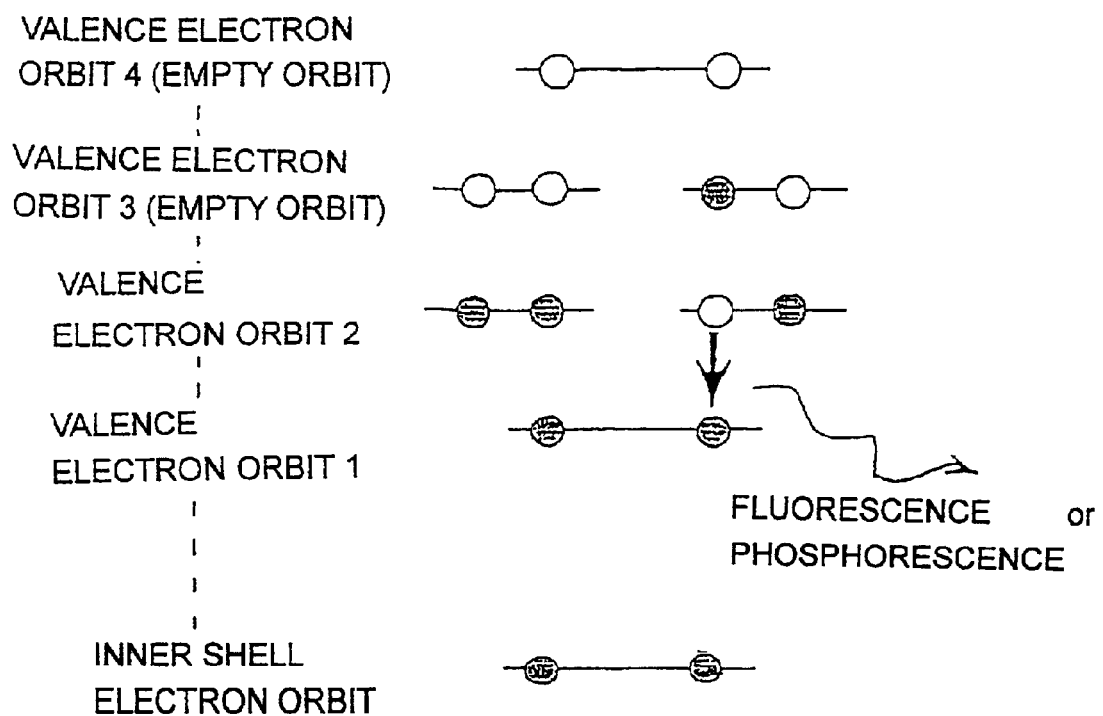
F I G. 4

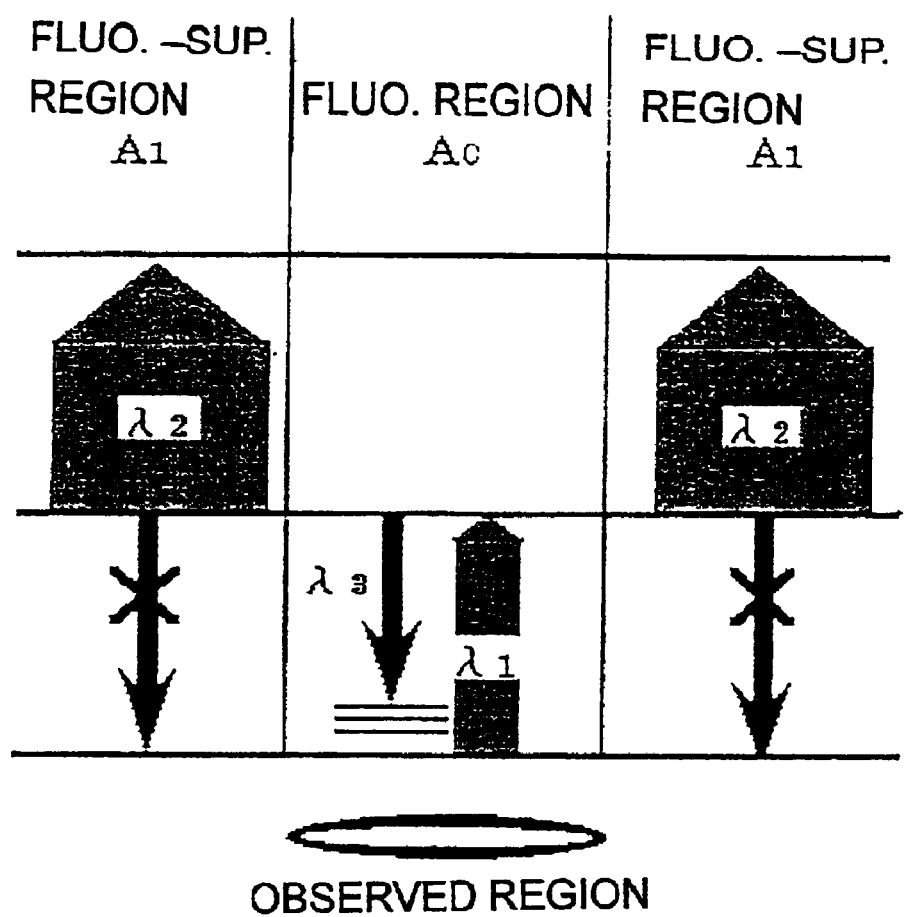
F I G. 6

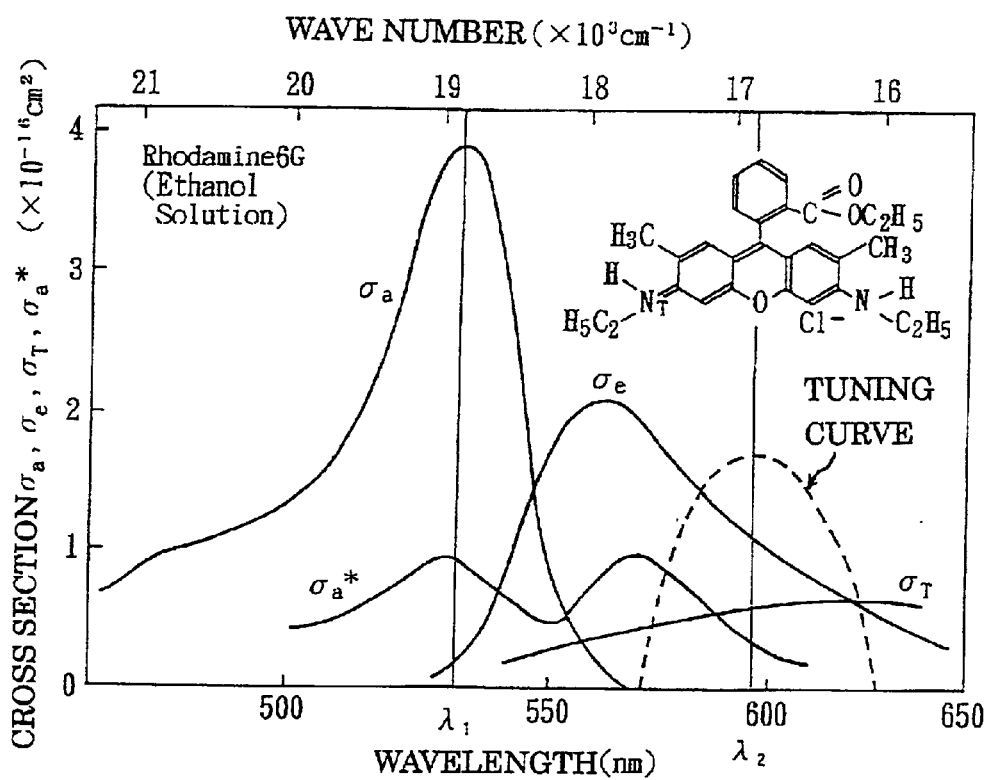
F I G. 1 0

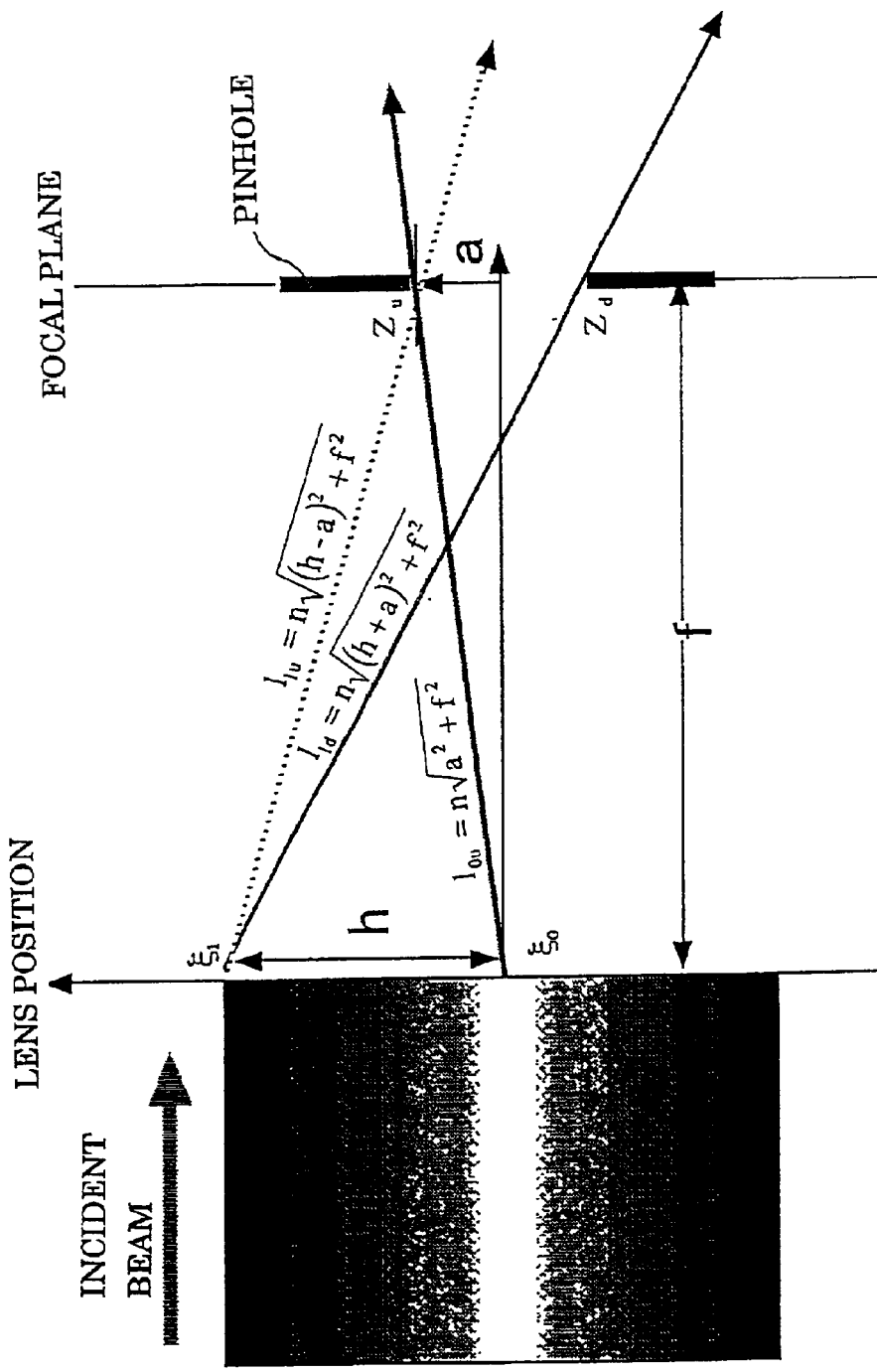
F I G. 12

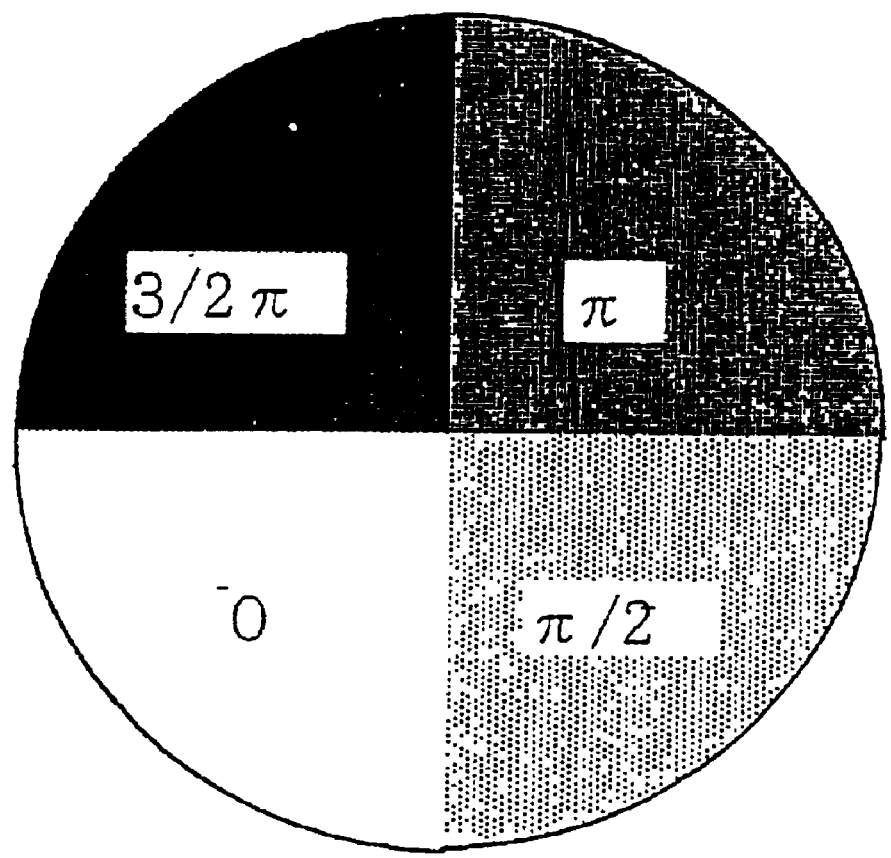
F I G. 1 9

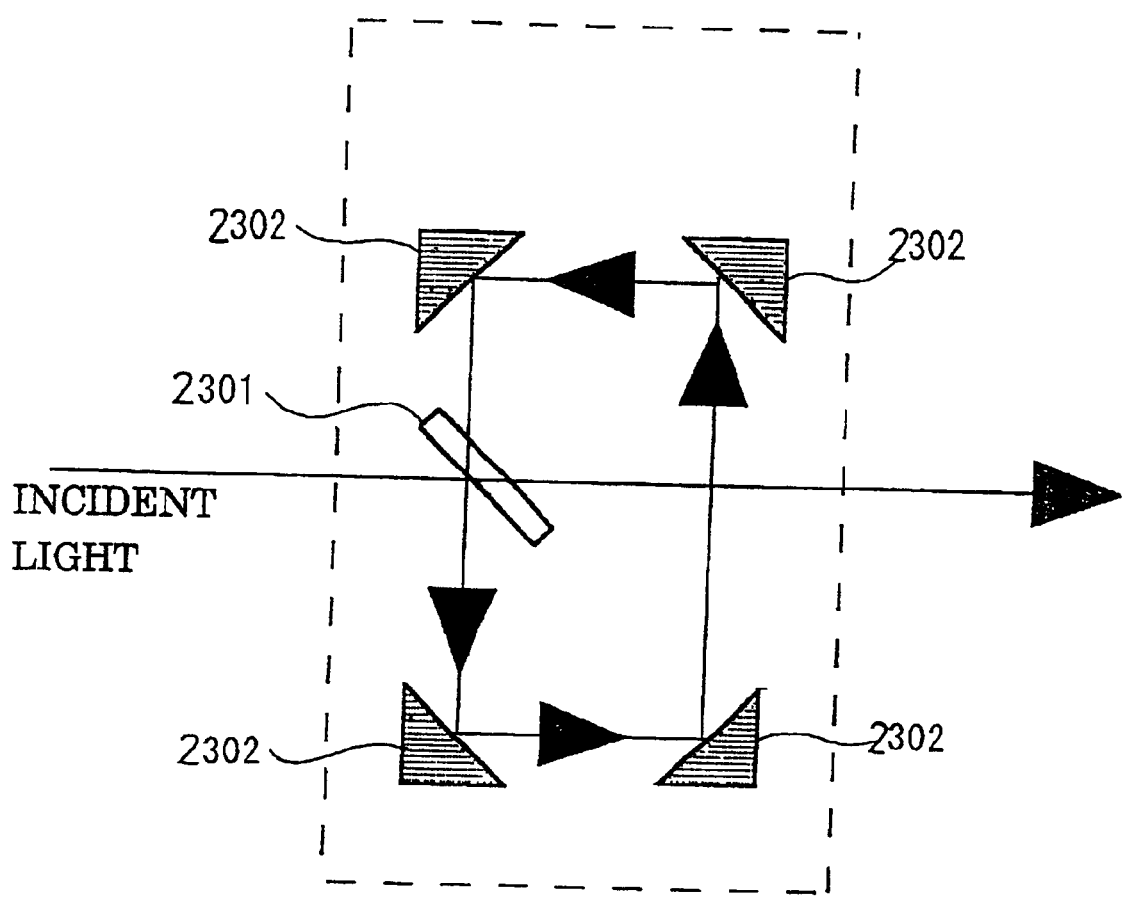
F I G. 2 3

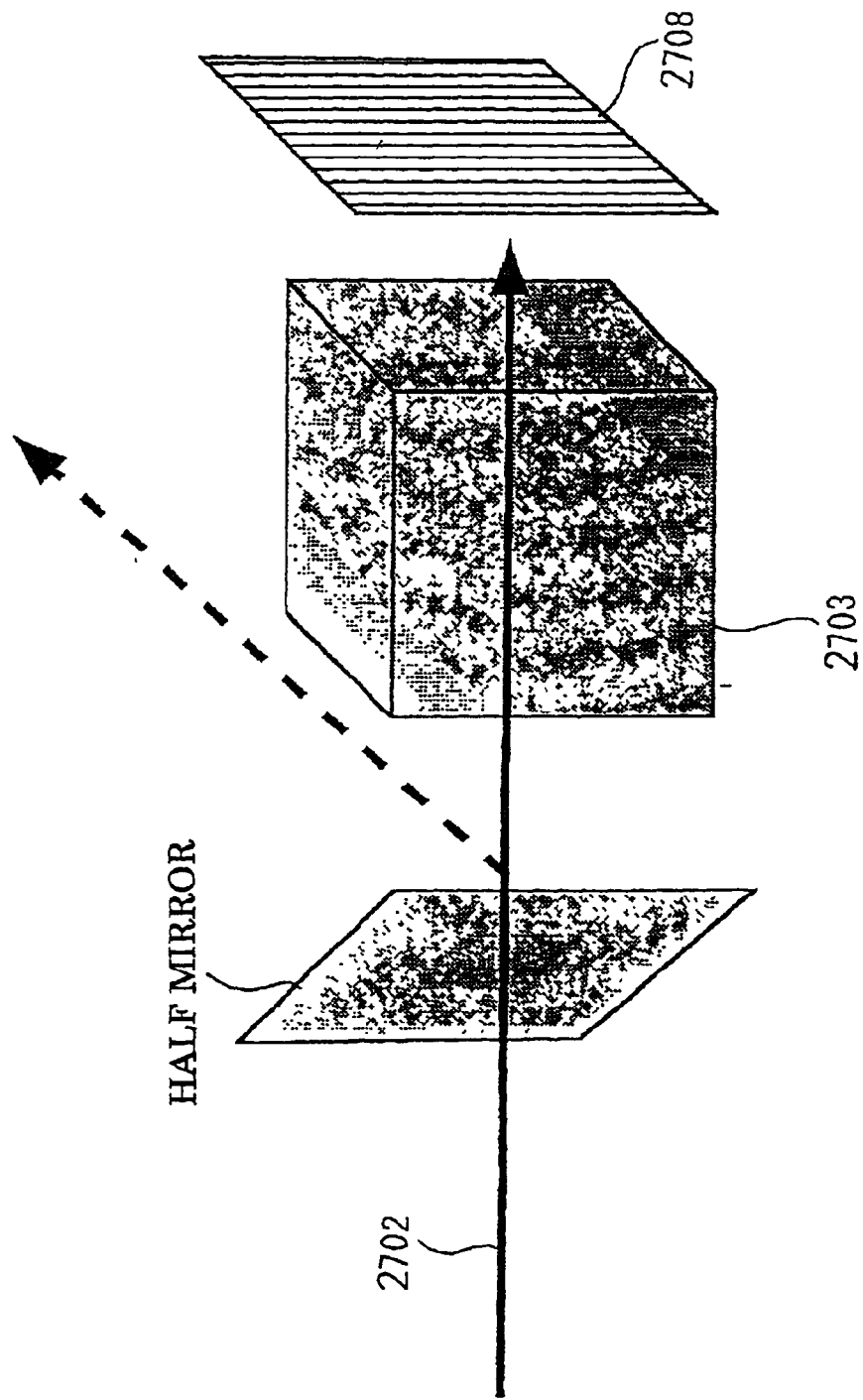

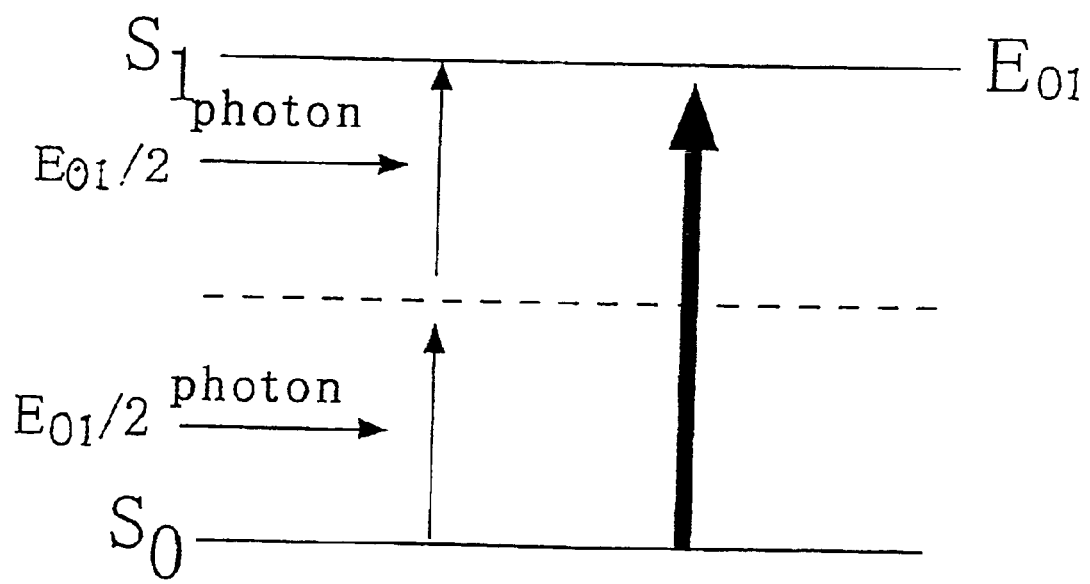
F I G. 3 2

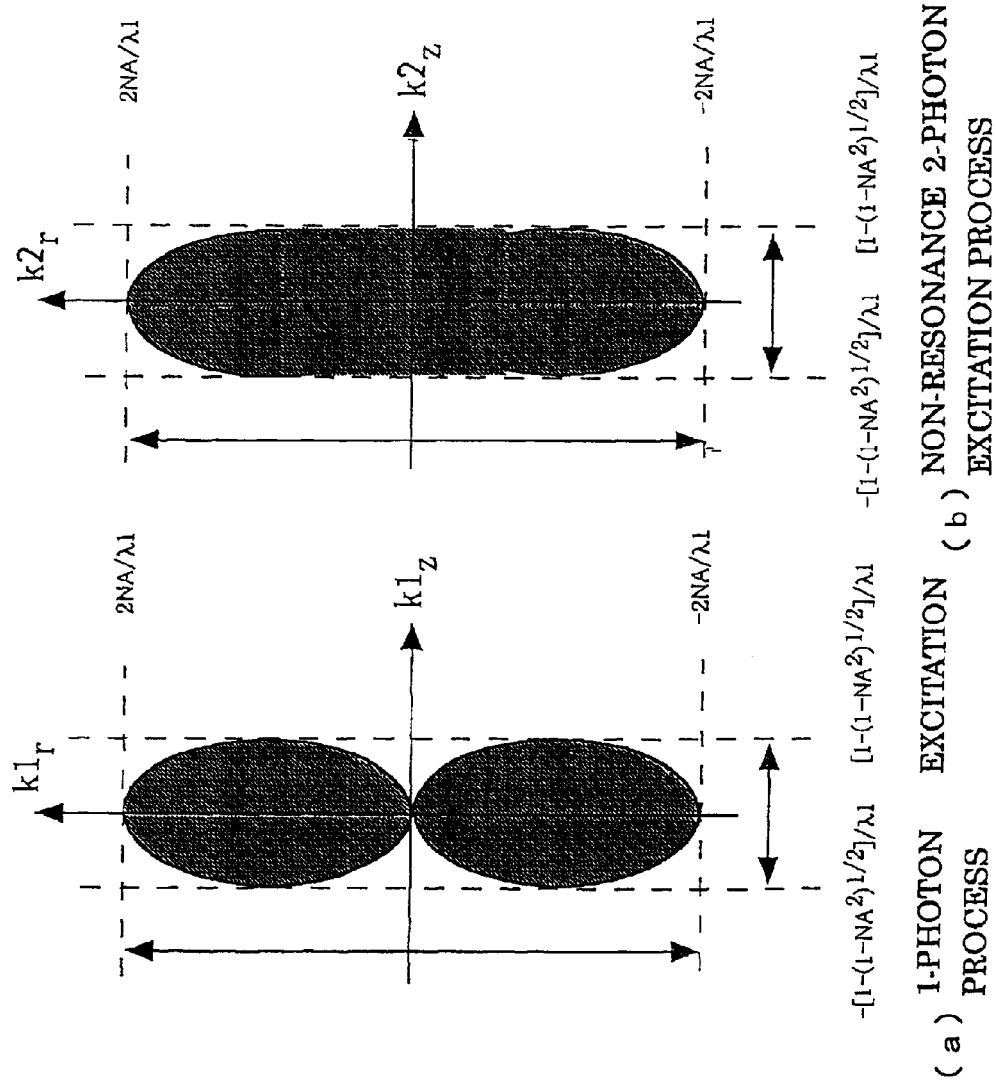
F I G. 3 5

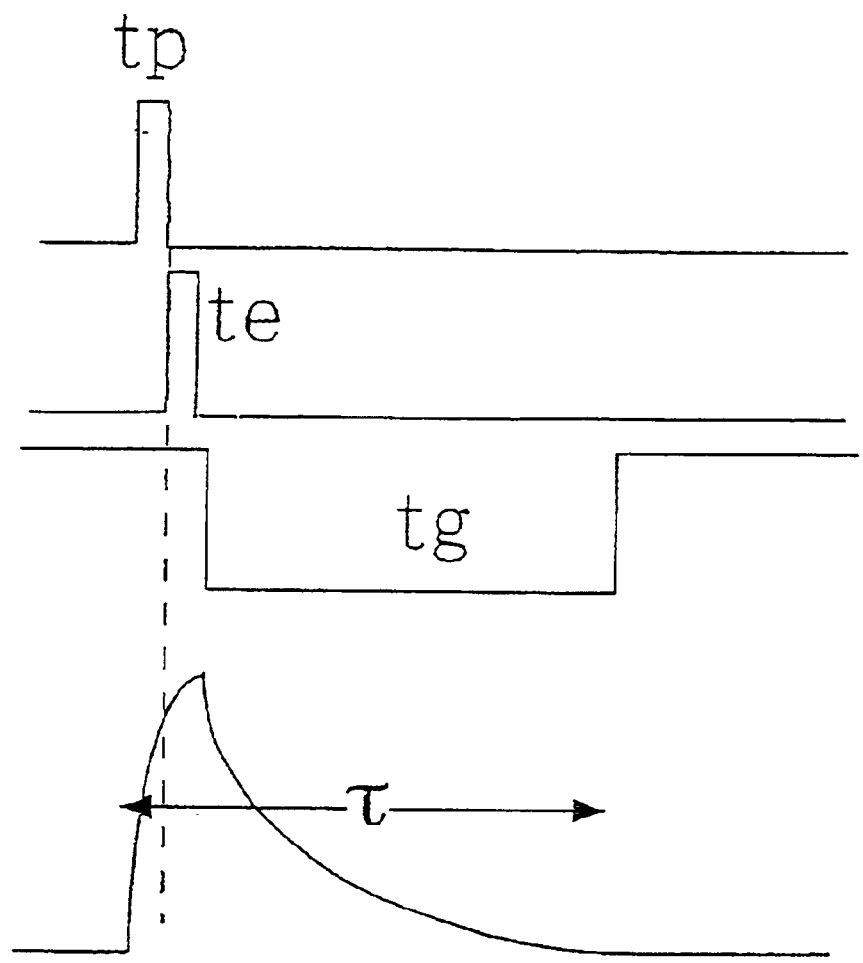
F I G. 3 7

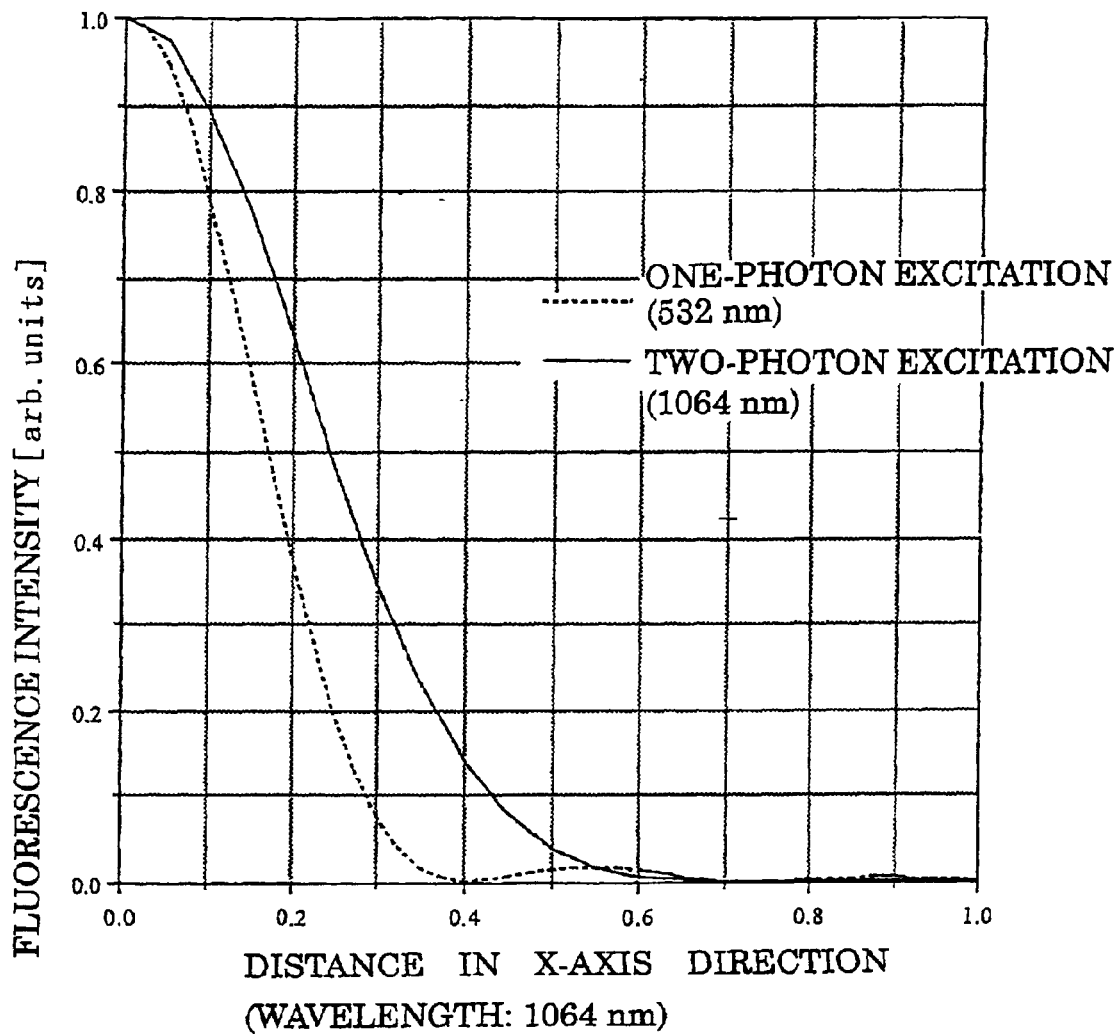
F I G. 3 9

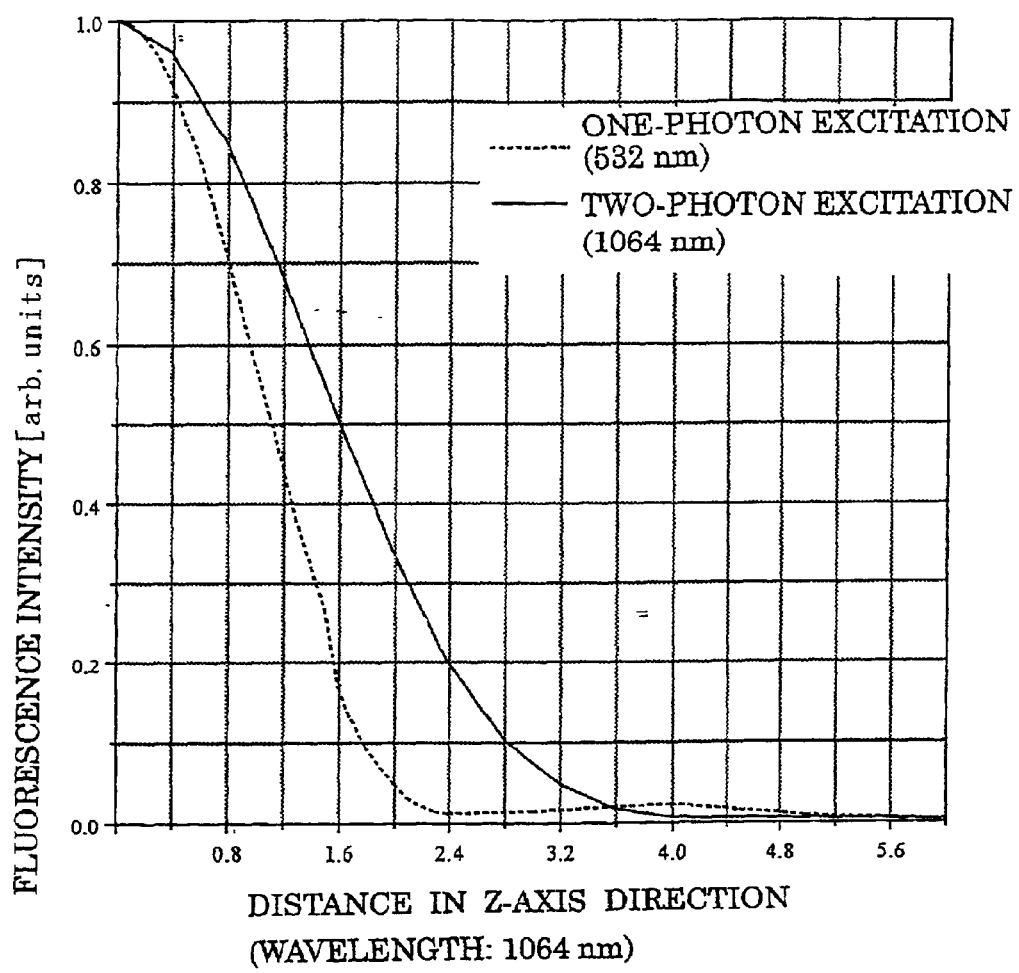
F I G. 40

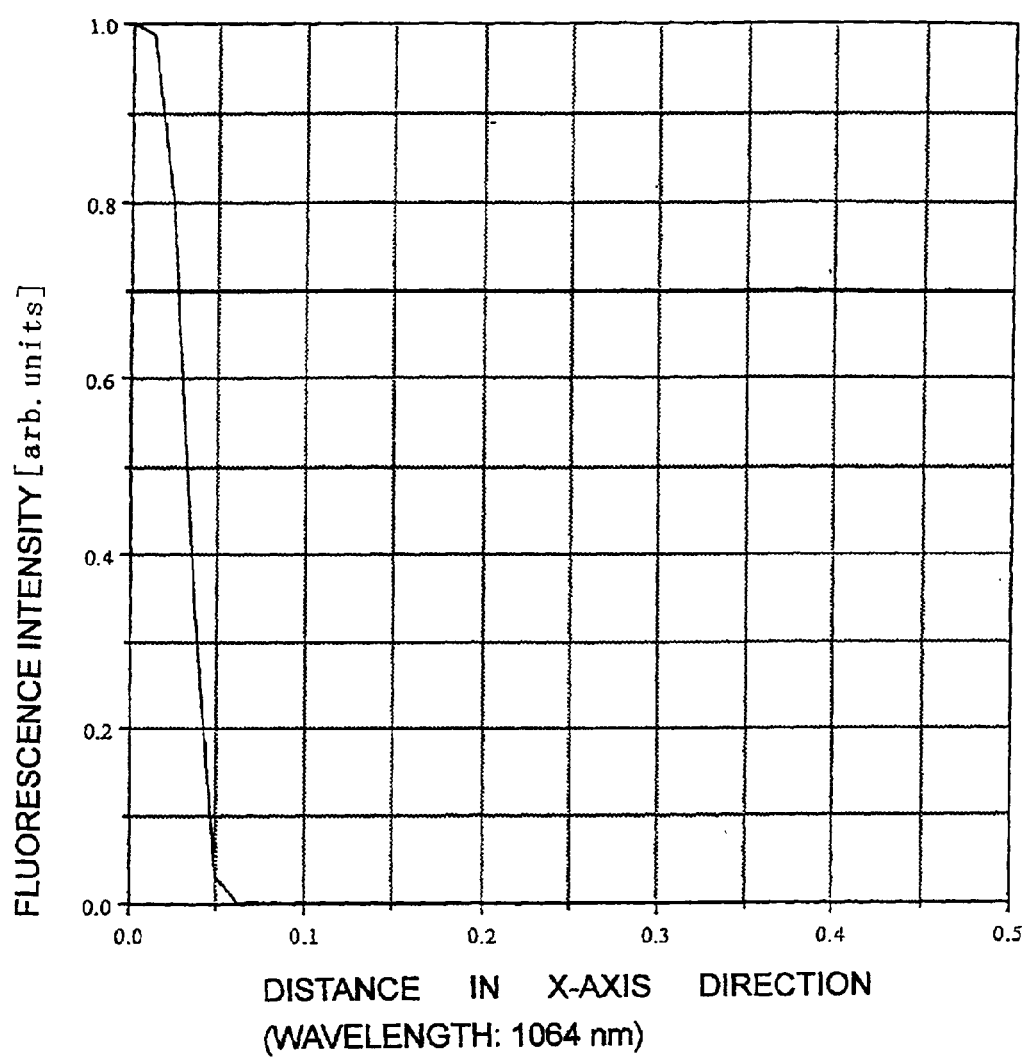
F I G. 4 2

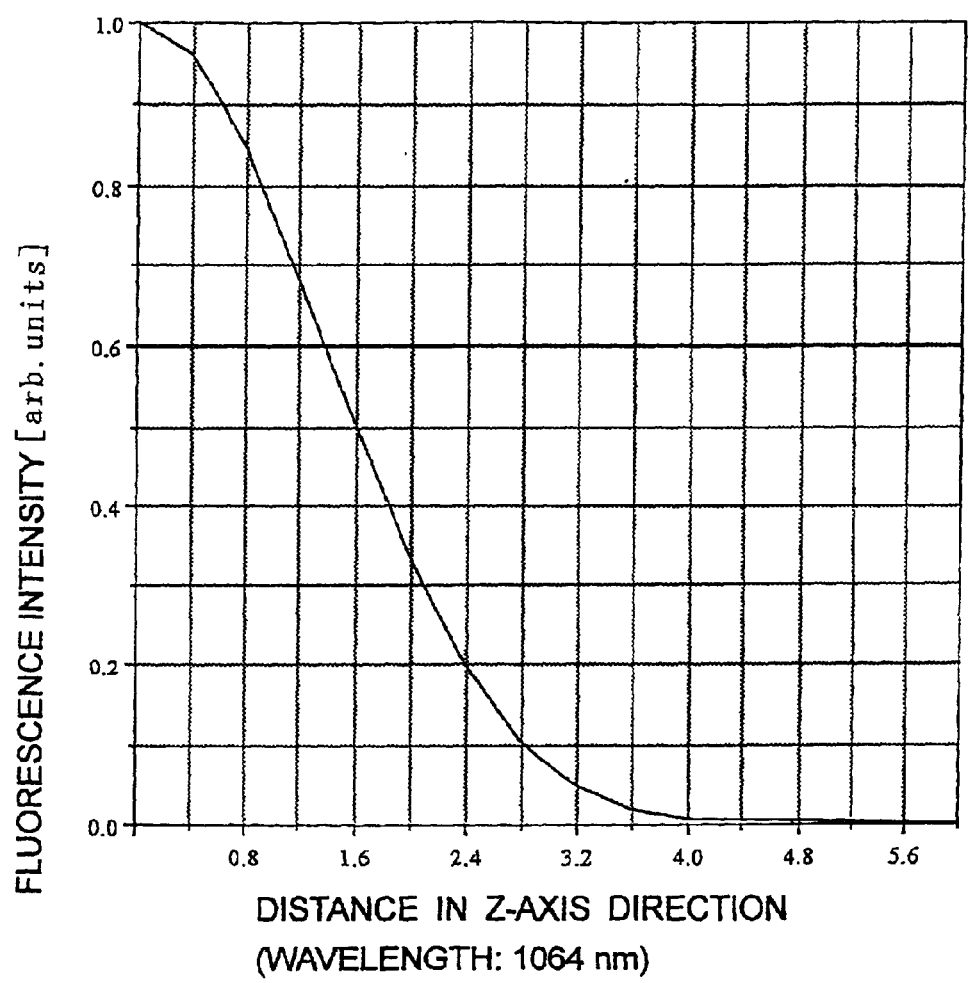
F I G. 4 3

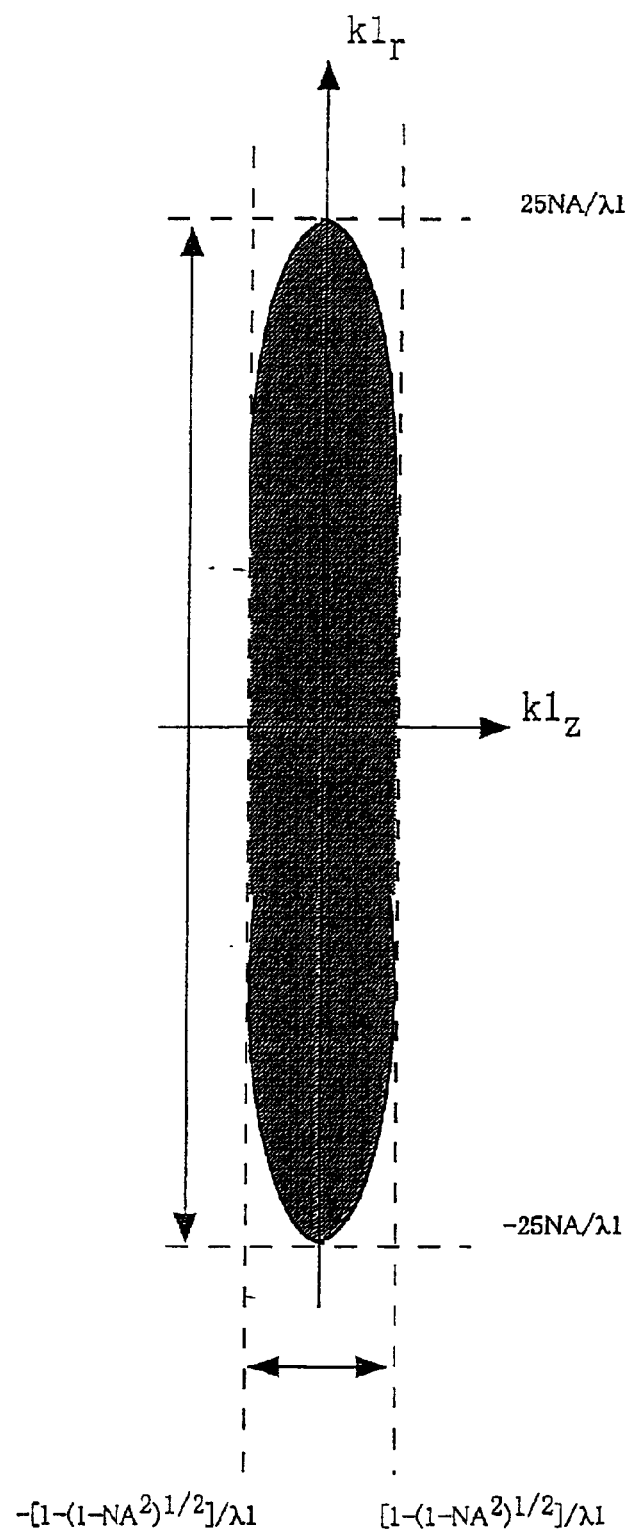
F I G. 4 4

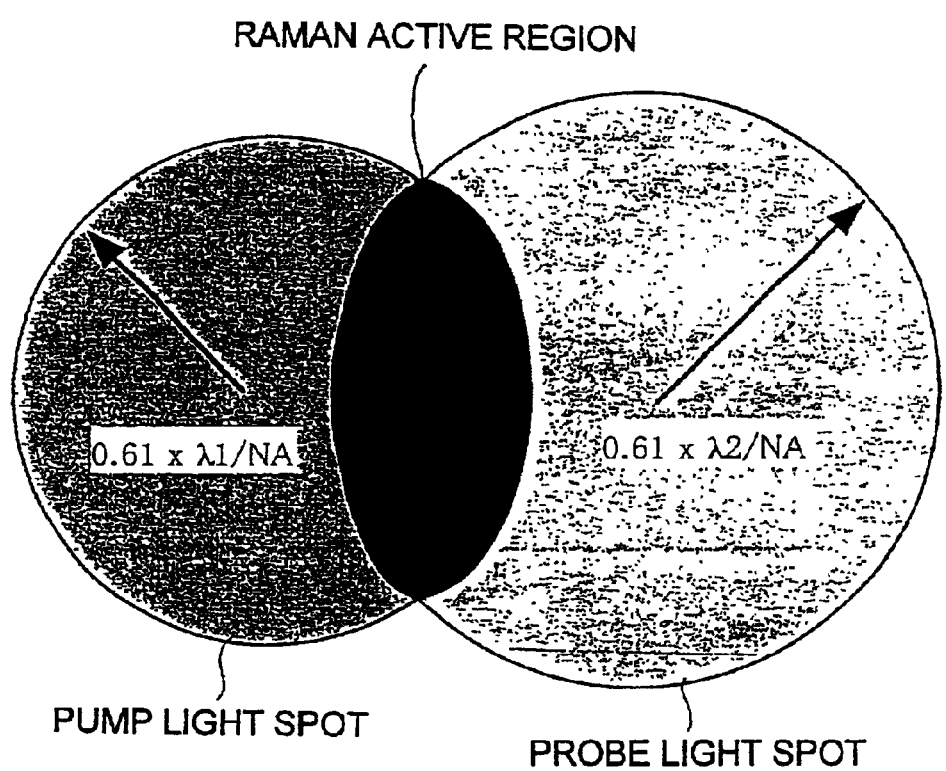
F I G. 4 9

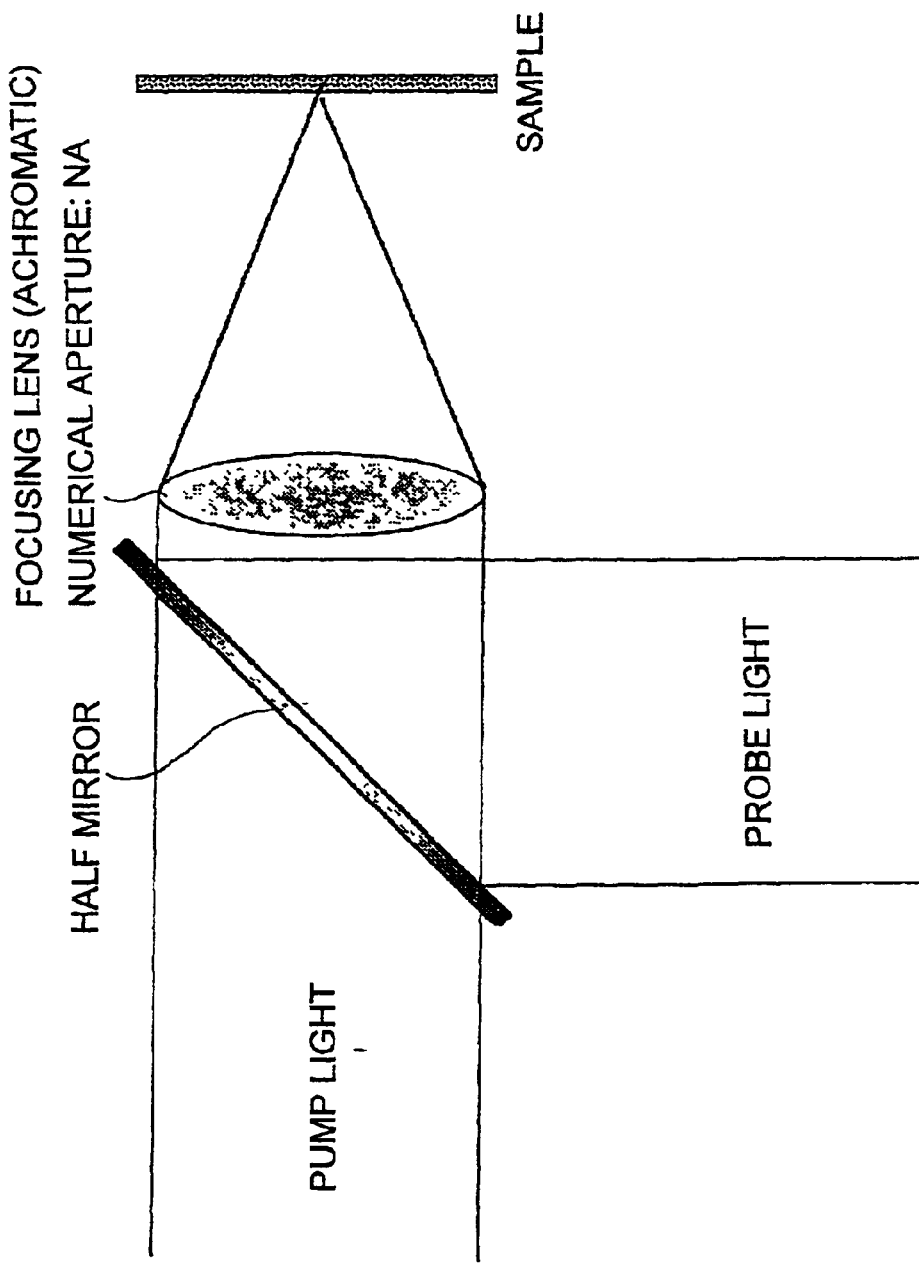
F I G. 5 0

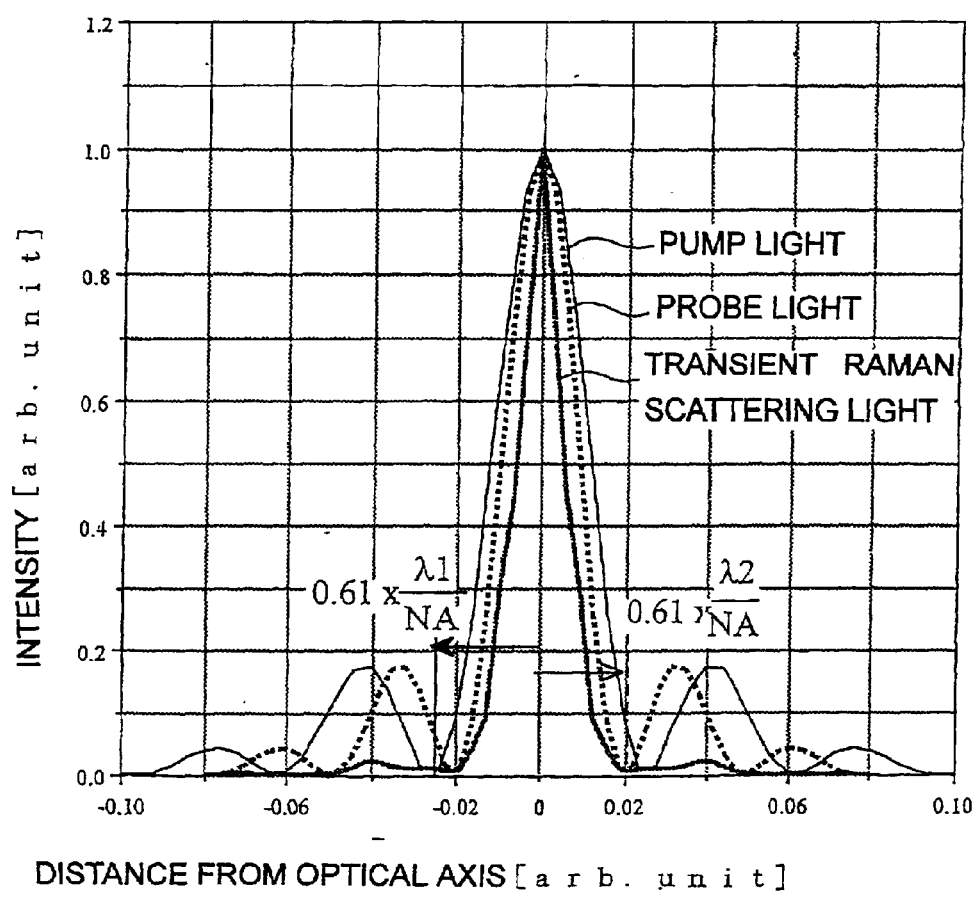
F I G. 5 1

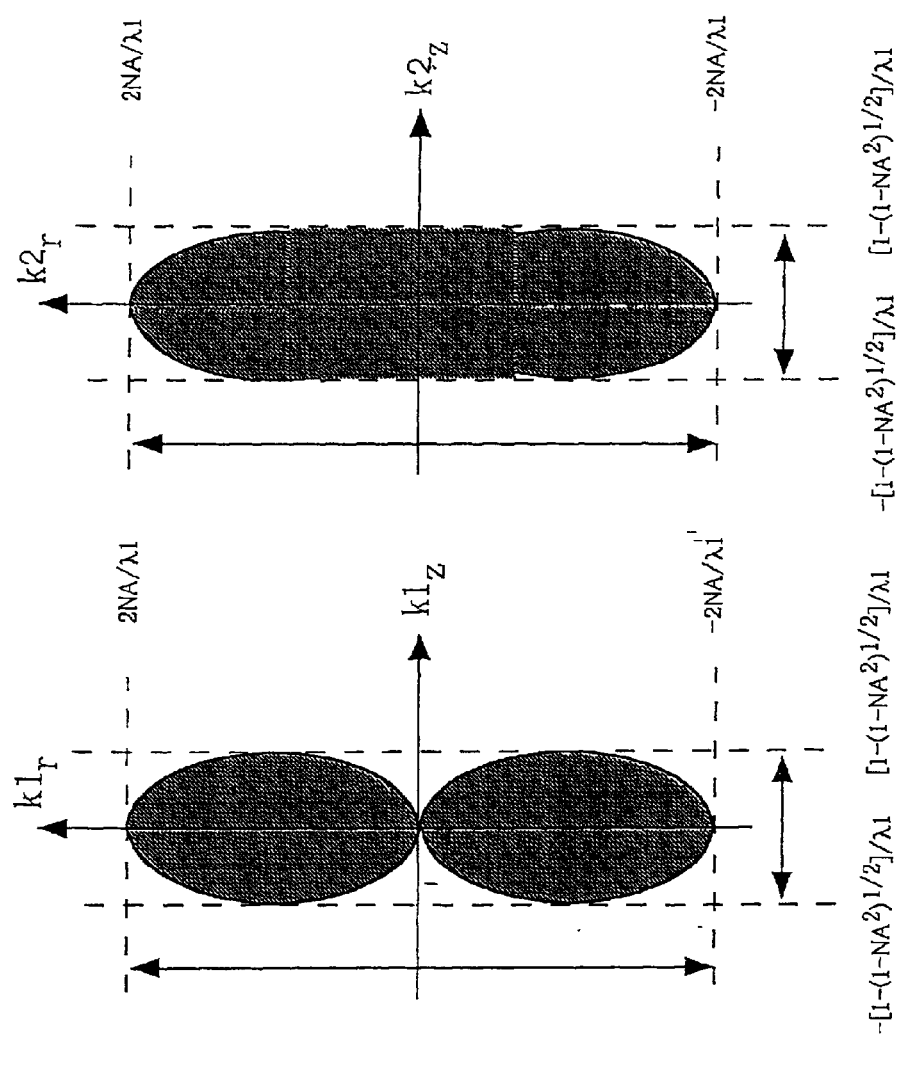
F I G. 5 2

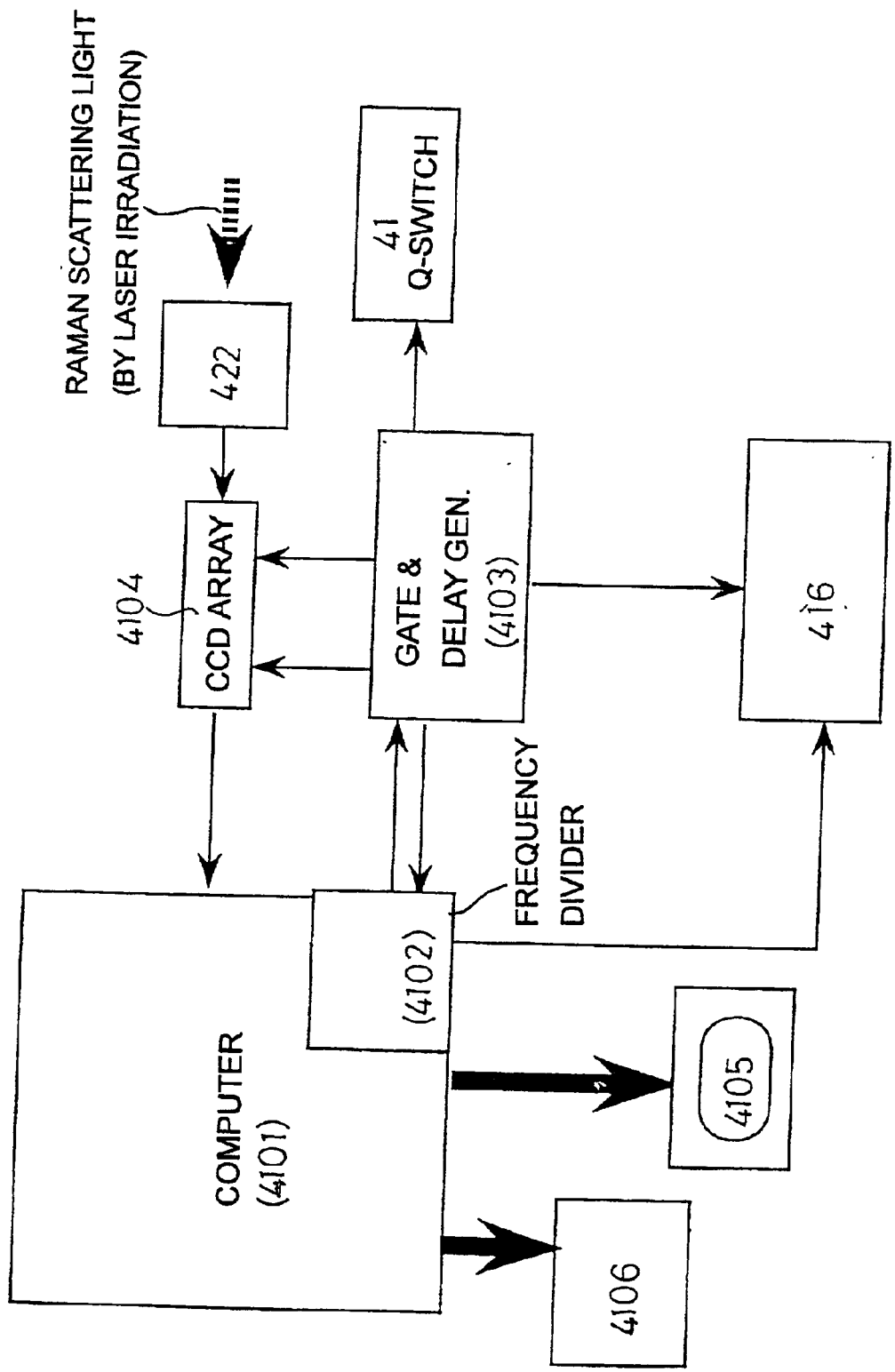
F I G. 54

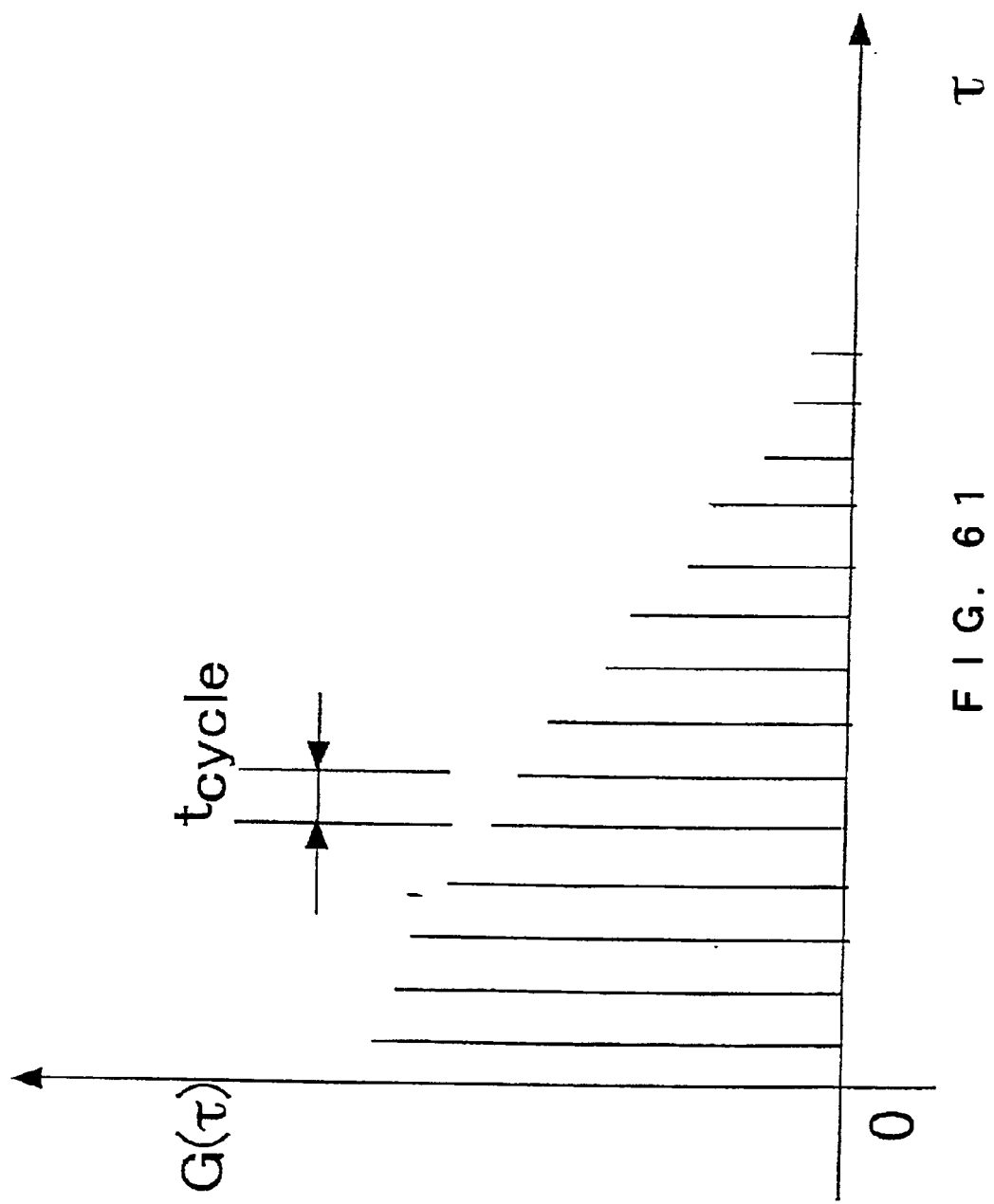

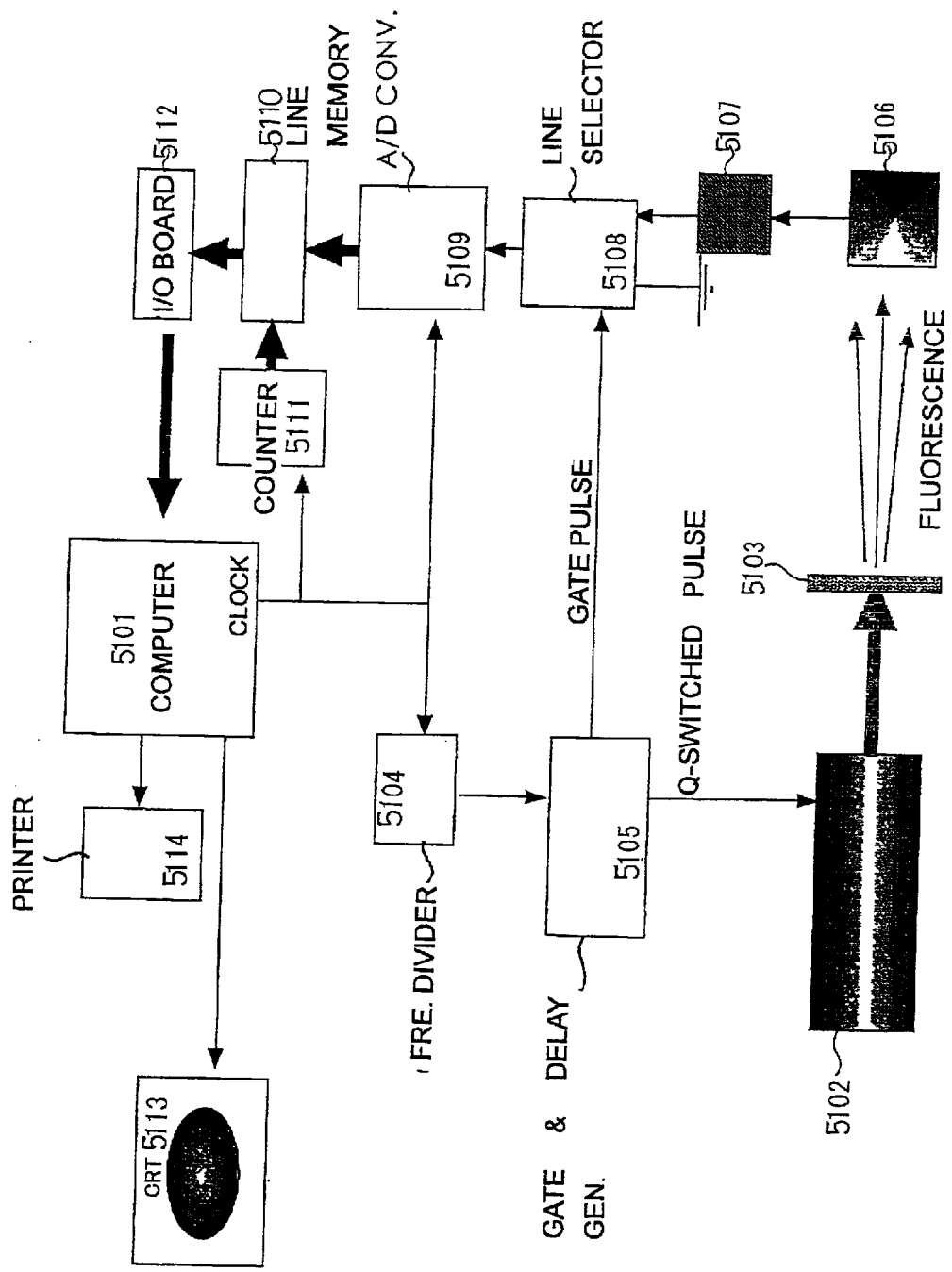
F I G. 6 2

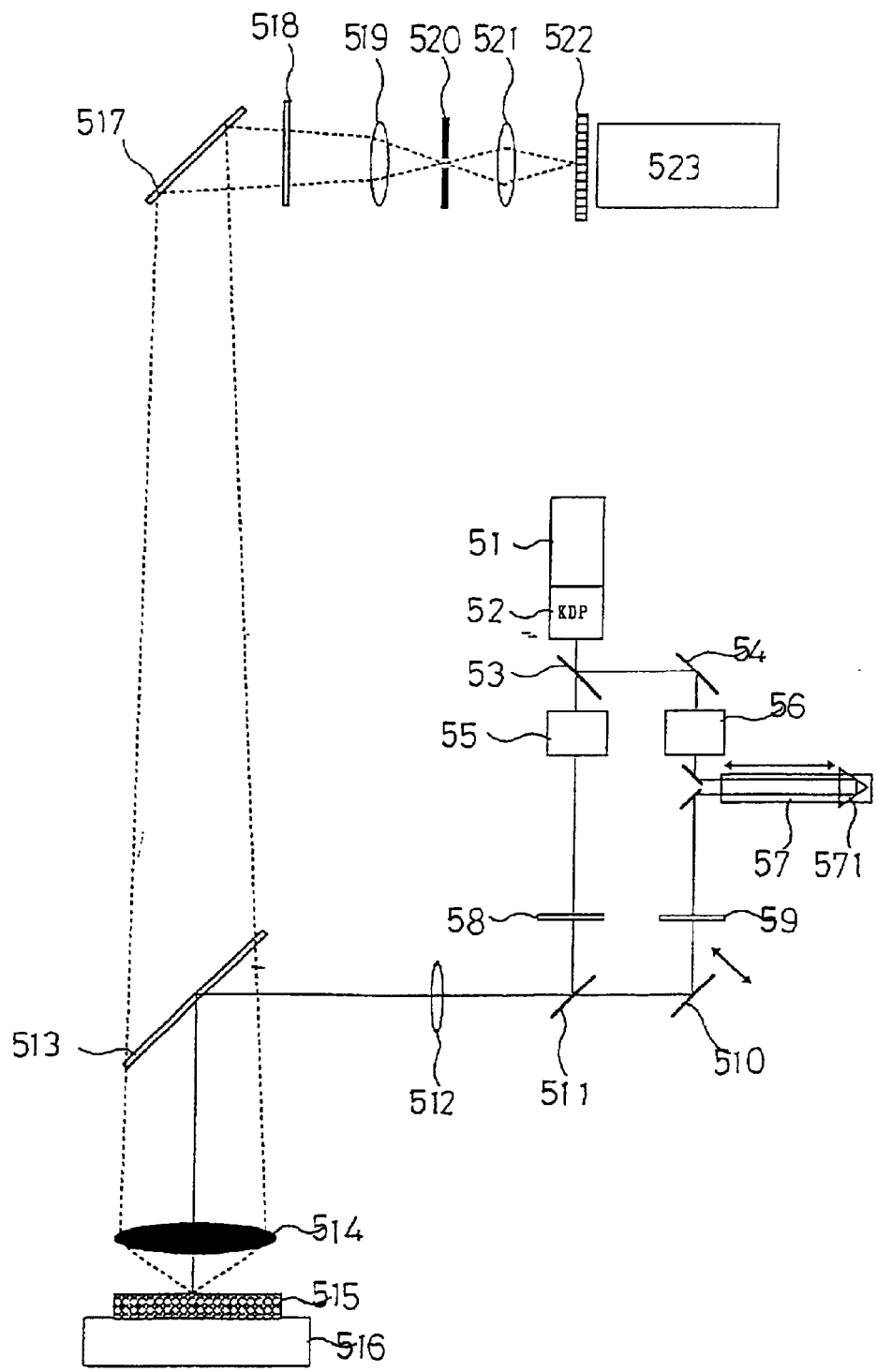
F I G. 64

US 6,844,963 B2

DOUBLE-RESONANCE-ABSORPTION MICROSCOPE

BACKGROUND OF THE INVENTION

1. Field of the Invention

The present invention relates to a double-resonance-absorption microscope that achieves super-resolution by using a double-resonance absorption process.

2. Description of the Related Art

In recent years, there have been developed various types of optical microscopes with high performances and multiple functions, along with the developments in the peripheral technologies including laser and electronic graphics technologies. As one of these optical microscopes, there has been proposed, by the inventor of the present invention, a microscope capable of contrast control of an image and chemical analysis of a sample by the use of a double resonance absorption process caused by irradiating the sample with plural wavelengths of light. This is hereinafter referred to as a double-resonance-absorption microscope (see Japanese patent application No. 329165/1994).

This double-resonance-absorption microscope can, by using the double resonance absorption process, select a specific kind of molecule and observe absorption and fluorescence caused by a specific optical transition. The principle is described below. Sample molecules forming a sample in a ground state (state $S_0$ of FIG. 1) have electrons in a valence electron orbit. These electrons in the valence orbit are first excited to a first electronic excited state (abbreviated state $S_1$ in FIG. 1) by light, such as a laser beam, of a resonance wavelength $\lambda_1$, and are subsequently excited to a second electronic excited state or a higher excited state (abbreviated state $S_2$ in FIG. 3) by light of a resonance wavelength $\lambda_2$. Then, the molecules in this excited state return to the ground state while emitting a fluorescence or a phosphorescence as illustrated in FIG. 4. An absorption image or a luminous image is observed by using the absorption process of FIG. 2 or the emission of the fluorescence or phosphorescence illustrated in FIG. 4.

In the excitation process to state $S_1$, the number of molecules in state $S_1$ in a unit volume increases as the intensity of the irradiating light increases. Since a linear absorption coefficient is given as the product of an absorption cross-section per molecule and the number of molecules per unit volume in the excitation process to state $S_2$, the linear absorption coefficient for the resonance wavelength $\lambda_2$ subsequently irradiated depends on the intensity of the light of the resonance wavelength $\lambda_1$ first irradiated. Accordingly, the linear absorption coefficient for the resonance wavelength $\lambda_2$ (hereinafter often simply referred to as the wavelength $\lambda_2$) can be controlled with the intensity of the light of the resonance wavelength $\lambda_1$ (hereinafter often simply referred to as the wavelength $\lambda_1$). This indicates that, when irradiating a sample with two wavelengths $\lambda_1$ and $\lambda_2$ of light and observing a transmission image obtained by the wavelength $\lambda_2$, contrast of the transmission image can be completely controlled with the light of the wavelength $\lambda_1$. Further, when the excited molecules deexcitate from state $S_2$ by emitting fluorescence of phosphorescence, its luminous intensity is proportional to the number of molecules in state $S_2$. Therefore, the image contrast can be controlled where the instrument is used as a fluorescence microscope.

Furthermore, the double-resonance-absorption microscope enables chemical analysis, as well as contrast control. Since the outermost valance orbit in FIG. 1 has an energy level intrinsic to each individual sample molecule, the wavelength $\lambda_1$ differs among each individual sample molecule. Also, the wavelength $\lambda_2$ is also intrinsic to each individual sample molecule. The prior art microscope which performs its irradiation and observation with a single wavelength can observe an absorption image or a fluorescence image of a specific molecule to a certain extent. However, it cannot accurately identify the chemical composition of a sample because, in general, the ranges of absorption wavelengths of some molecules overlap with each other. In contrast, the double-resonance-absorption microscope can limit absorbing or emitting molecules by the two wavelengths of $\lambda_1$ and $\lambda_2$ and thus identify the chemical composition of the sample more precisely than the prior art instrument.

Moreover, when the valance electron is to be excited, only light having a certain electric-field vector with respect to the molecular axis is intensively absorbed. Thus, if an absorption image or fluorescence image is obtained while determining the polarization directions of the wavelengths $\lambda_1$ and $\lambda_2$, the orientation directions can also be identified for the same molecule.

There has also been proposed, by the inventor of the present invention, another double-resonance-absorption microscope of a high spatial resolution exceeding the diffraction limit by using the double resonance absorption process. In the double resonance absorption process, there exist some molecules which emit extremely weak fluorescence from state $S_2$ as in FIG. 5. The molecules having such optical properties experience a unique phenomenon as described below.

FIG. 6 is a conceptual diagram of a double resonance absorption process similarly to FIG. 5. The x-axis is set along the horizontal axis of FIG. 6 to express the spread of spatial distance. In FIG. 6, a spatial area $A_1$ is irradiated with both wavelengths $\lambda_1$ and $\lambda_2$ of light, while a spatial area $A_0$ is irradiated with only the wavelength $\lambda_1$ of light. These spatial areas $A_1$ and $A_2$ are referred to as the fluorescence inhibited area and the fluorescence area, respectively.

In the spatial area $A_0$, a great number of molecules in state $S_1$ are generated by the excitation with the wavelength $\lambda_1$, and fluorescence emitted with a wavelength $\lambda_3$ can be observed. In the spatial area $A_1$, however, the molecules in state $S_1$ are instantly excited to the higher state $S_2$ by irradiation with the wavelength $\lambda_2$ and thus disappear. As a result, the fluorescence is completely inhibited in the spatial area $A_1$ because the fluorescence of the wavelength $\lambda_3$ will not be emitted at all and because the fluorescence from molecules in state $S_2$ does not exist intrinsically. Consequently, the fluorescence is emitted only from the spatial area $A_0$. Such a phenomenon has been observed with some kinds of molecules.

Accordingly, in the prior art scanning laser microscope or the like, the size of a microbeam that is created on an observed sample by focusing laser light is determined by the diffraction limit that depends on the numerical aperture of the focusing lens and on the wavelength. It cannot be theoretically expected, therefore, that higher spatial resolution will be obtained. In the phenomenon illustrated in FIG. 6, light of wavelength $\lambda_1$ and light of wavelength $\lambda_2$ are made to overlap with each other spatially and thus fluorescence region is restricted with illumination of light of wavelength $\lambda_2$. Therefore, if we take notice of a region irradiated with light of wavelength $\lambda_1$, the fluorescence region is narrower than the size of the beam that is determined by the numerical aperture of the focusing lens and by the wavelength. This substantially improves the spatial resolution. The present inventor's double-resonance-absorption microscope (see: Japanese patent application No. 302232/1996) uses this principle to achieve a microscope having super-resolution exceeding the diffraction limit.

In an attempt to further enhance the super-resolution of the double-resonance-absorption microscope, the present inventor has already made a proposal for adjusting the sample to make full use of the functions and for timing at which light of wavelength $\lambda_1$ and light of wavelength $\lambda_2$ are directed to the sample (see Japanese patent application No. 255444/1997). In particular, the sample is stained with staining molecules, which have at least three quantum states $S_0$, $S_1$, and $S_2$ including the ground state. Furthermore, when these molecules are deexciting from a higher quantum state excluding state $S_1$ to the ground state, a thermal relaxation process is more prevalent than a relaxation process due to fluorescence. These molecules are hereinafter referred to as the fluorescence labeler molecules. In a sample, such fluorescence labeler molecules and biological molecules biologically stained are chemically bonded. This sample is irradiated with light of wavelength $\lambda_1$ to promote the fluorescence labeler molecules to state $S_1$. Immediately thereafter, the sample is irradiated with light of wavelength $\lambda_2$ to excite the fluorescence labeler molecules to a still higher quantum level. Consequently, fluorescence from state $S_1$ can be effectively suppressed. At this time, the aforementioned artificial spatial suppression of the fluorescence region is performed. In this way, a further improvement of the spatial resolution can be accomplished.

The optical properties of the above-described fluorescence labeler molecules can be explained from a quantum-chemical point of view as follows. Generally, molecules are bonded by a σ bond or π bond of atoms constituting the molecules. In other words, molecular orbits have σ-molecular orbits or π-molecular orbits. Electrons existing in these molecular orbits play a key role in bonding together atoms. Among them, electrons in σ-molecular orbits strongly bond atoms and determine the intermolecular distances within each molecule (i.e., the skeleton of the molecule). On the other hand, electrons in π-molecular orbits contribute little to bonding of atoms. Rather, they are bound to the whole molecule with a quite weak force.

Where electrons existing in σ-molecular orbits are excited with light, interatomic spaces in a molecule often vary greatly, resulting in a large structural change including dissociation of the molecule. As a result, the kinetic energy of the atoms or the energy given to the molecule by the light to cause the structural change is almost fully changed into thermal energy. Therefore, excitation energy is not consumed in the form of light, i.e., fluorescence. Since a molecular structural change takes place quite quickly (e.g., in a time shorter than picosecond), if fluorescence occurs during the process, the life of the fluorescent light is quite short on the other hand, where electrons in π-molecular orbits are excited, the molecular structure itself is hardly varied. The electrons stay in higher-order discrete quantum levels for a long time. They release fluorescent light for orders of nanoseconds and deexcite.

In quantum chemistry, having a π-molecular orbit is equivalent to having a double bond for a molecule. It is necessary that a fluorescence labeler molecule having a rich amount of double bonds be selected. It has been confirmed that among molecules having double bonds, six-membered ring molecules such as benzene and belladine show quite weak fluorescence from state $S_2$ (e.g., M. Fujii et. al., Chem. Phys. Lett. 171 (1990) 341). Therefore, if molecules including six-membered rings such as benzene and belladine are selected as fluorescence labeler molecules, the life of fluorescence from molecules in state $S_1$ is prolonged. In addition, fluorescence from molecules can be easily suppressed by exciting them from state $S_1$ to state $S_2$ by light illumination. Hence, it is possible to make effective use of the super-resolution of the aforementioned double-resonance absorption microscope.

That is, if a sample is stained with these fluorescence labeler molecules and an observation is made, a fluorescence image with high spatial resolution can be obtained. Additionally, only a desired chemical structure of a biological sample can be stained by adjusting the chemical groups on side chains of the fluorescence labeler molecules. In consequence, even detailed chemical compositions of the sample can be analyzed.

Generally, a double-resonance-absorption process takes place only when two wavelengths of light, state of polarization, and other factors satisfy certain conditions. Therefore, use of this process makes it possible to know the molecular structure quite accurately. In particular, the direction of polarization of light has a strong correlation with the direction of orientation of the molecules. A strong double-resonance-absorption process occurs when the directions of polarization of two wavelengths of light have certain angles with respect to the direction of orientation of the molecules. Accordingly, the degree of extinction of fluorescence is varied by illuminating the sample with the two wavelengths of light and rotating their directions of polarization. Hence, information about the spatial orientation of a structure to be observed can be obtained by observing the manner in which the extinction varies. This can also be made possible by adjusting the two wavelengths of light.

Another method as proposed in Japanese patent application No. 255444/1997 improves the S/N of the resulting fluorescence image and suppresses the fluorescence more effectively by appropriately adjusting the timing at which the wavelengths $\lambda_1$ and $\lambda_2$ of light are illuminated.

In addition, the present inventor has proposed a method of improving the S/N and suppression of fluorescence further by more ingeniously devising the timing at which the wavelengths $\lambda_1$ and $\lambda_2$ of light are illuminated (see Japanese patent application No. 97924/1998).

The region irradiated with the light of wavelength $\lambda_1$ overlaps a part of the region irradiated with the light of wavelength $\lambda_2$ as mentioned previously. This can be accomplished by shaping the light of wavelength $\lambda_2$ into a hollow beam (i.e., having a central portion (around the axis) of zero intensity and having an intensity distribution symmetrical with respect to the axis), bringing this hollow beam into registry with a part of the light of wavelength $\lambda_1$, and focusing the light onto a sample. FIG. 7 is a conceptual diagram illustrating this overlap and the fluorescence suppression caused thereby. The light of wavelength $\lambda_2$ is shaped into a hollow beam by a phase plate as shown in FIG. 8. The light of wavelength $\lambda_2$ in the form of a hollow beam and light of wavelength $\lambda_1$ are made to overlap with each other. This suppresses fluorescence other than in a region close to the optical axis where the intensity of light of wavelength $\lambda_2$ is zero. Only fluorescence is observed which arises from the fluorescence labeler molecules (or sample molecules) existing in a region narrower than the spread of the light of wavelength $\lambda_1$. As a result, super-resolution is developed.

The phase plate of FIG. 8 gives a phase difference of π to the light of wavelength $\lambda_2$ with respect to the optical axis.

The light of wavelength $\lambda_2$ is passed through this phase plate, inverting the phase of the light of wavelength $\lambda_2$ in the region on and close to the optical axis. As a consequence, the electric field strength in the region close to the optical axis is brought to zero. Thus, the light of wavelength $\lambda_2$, which assumes the form of a hollow beam, can be obtained.

While the double-resonance-absorption microscope developed thus far by the present inventor exhibits excellent super-resolution and analyzing capability (which provide great usefulness) and technical superiority, the actual situation is that this instrument still has points to be improved as described below. Light for exciting sample molecules (i.e., molecules constituting a sample) from state $S_0$ to $S_1$ is hereinafter referred to as "pump light". Light for exciting molecules in state $S_1$ to state $S_2$ is referred to as "erase light". Erase light assuming the form of a hollow beam is referred to as "hollow erase light". Excitation from state $S_0$ to state $S_1$ is abbreviated as "excitation $S_0 \rightarrow S_1$". Excitation from state $S_1$ to state $S_2$ is abbreviated as "excitation $S_1 \rightarrow S_2$". Where a sample is stained with fluorescence labeler molecules to realize super-resolution more effectively, the sample molecules are none other than the fluorescence labeler molecules.

[I] Ideal Hollow Erase Light

First, in order to realize super-resolution by a double-resonance-absorption microscope as expected theoretically by suppression of a fluorescence region due to partial overlap between regions irradiated with pump light and erase light, respectively, it is necessary that the hollow erase light assume the anticipated form of a hollow beam. Disturbance of this shape of the hollow beam, i.e., disturbance of the intensity distribution, leads to deterioration of the microscope image.

Lasers are often used as light sources for erase light. In order to shape erase light from a light source into the expected hollow beam, it is absolutely necessary that the beam profile of the laser light be regulated. That is, the intensity distribution of the beam must be symmetrical with respect to the optical axis. However, the beam profile of adyelaser, for example, is close to a triangle. Furthermore, the intensity distribution it not uniform. Therefore, it may be difficult to obtain the expected hollow beam. Consequently, the beam profile focused onto a sample shows a disturbed beam pattern. This causes a deterioration of the resolution or image quality of the microscope.

Furthermore, it has been proposed to obtain hollow erase light via a zonal aperture. However, if this aperture is utilized, it is difficult to perform alignment or focusing. Along adjusting time and a very large amount of labor are required until a good image is obtained. Moreover, skillfulness for this is necessary. These are unfavorable in practical applications.

Additionally, a first-order Bessel beam having an ideal beam profile as hollow erase light has been proposed. As shown in FIG. 9, if the first-order Bessel beam is caused to make one revolution around the optical axis, the phase varies by $2\pi$. Theoretically, two points that are symmetrical with respect to the optical axis are shifted in phase with respect to each other by $\pi$. Therefore, on the axis, the electric fields completely cancel out, and the strength of the resultant field is zero. In practice, however, the phase plane of the laser light is not completely uniform within the plane of the beam. As it goes away from the center of the beam, the phase plane becomes more disturbed. Therefore, when a first-order Bessel beam is created, cancellation of the electric fields becomes incomplete due to the disturbance of the phase plane. In the resulting first-order Bessel beam, the intensity at the center of the beam is not exactly zero. It cannot be said that this hollow erase light is ideal for a double-resonance-absorption microscope.

Accordingly, there is a demand for a technique capable of generating both super-resolution and ideal hollow erase light.

[II] Operability and Maintainability of Light Source

Secondly, the double-resonance-absorption microscope is, of course, required to have good operability and maintainability in the same way as other microscopes. The above-described double-resonance-absorption microscope uses a wavelength variable laser such as a dye laser or an optical parametric oscillator (OPO) as a light source and so this technique can be applied to resonance conditions of various fluorescence labeler molecules. However, conventional dye lasers suffer from drops in the amount of light due to deterioration of dyes. Also, frequent and cumbersome operations for replacing the dye are necessary. Therefore, the dye lasers are not favorable from a practical point of view. The OPO is convenient but is a quite accurate optical system. Therefore, humidity and temperature must be strictly controlled. Furthermore, the used nonlinear optical crystal has a short life and is expensive. Since the whole system is also expensive, a heavy burden is imposed on the user in servicing the light source. Accordingly, there is a demand for a light source that has excellent operability and maintainability.

[III] Mixing of Excitation Light into Detection Signal

Thirdly, depending on the molecules to be excited, the wavelength range of fluorescence from the molecules maybe close to or overlap with the wavelengths of erase light and pump light for exciting the molecules. Therefore, when the resulting fluorescence signal is detected, the excitation light forms background light. This may make it difficult to extract the fluorescence signal to be measured. Especially, for the erase light, it is necessary to excite the molecules from state $S_1$ to state $S_2$ and so the intensity is relatively high. Its effects need to be taken into consideration. For example, in the above-cited technique (Japanese patent application No. 97924/1998), where a sample is stained with fluorescence labeler molecules, if rhodamine 6G is used as the fluorescence labeler molecules, the fluorescence region extends from a wavelength of about 530 nm to a wavelength of 650 nm as shown in FIG. 10. The wavelength of the pump light for rhodamine 6G is 532 nm, while the wavelength of the erase light is 599 nm. Therefore, the fluorescence region overlaps with the exciting wavelengths. Consequently, the S/N of the obtained fluorescence image is not good. Accordingly, there is a demand for a technique for suppressing mixing of the excitation light into the detected signal, thus achieving high S/N.

[IX] 3D Spatial Resolution

Fourthly, attempts have been made to improve the performance of microscopes in recent years. In this connection, realizing sufficient depth resolution in the direction of the optical axis, i.e., 3D (three-dimensional) spatial resolution is a great subject. However, the double-resonance-absorption microscope has no depth resolution in the direction of the optical axis, similar to other conventional optical microscopes. As mentioned previously, where the region irradiated with pump light is made to overlap with the region irradiated with erase light, the spatial resolution is improved only in two dimensions. In peripheral regions of the pump light beam with which the erase light overlaps, fluorescence is suppressed. However, on the optical axis in the hollow portion of the erase light, fluorescence is not suppressed at all, but rather molecules on the optical axis emit light. That is, in theory, there is no depth resolution in the direction of the optical axis. To have depth resolution, pinholes may be placed over the whole surface of the detector and at the confocal position. Unfortunately, this may present practical problems. That is, alignment of the focusing optical system including the pinholes is made complex. Furthermore, the number of photons of fluorescence reaching the detector is reduced. Therefore, if a microscope equipped with an uncomplex focusing optical system and having depth resolution, in addition to 2D (two-dimensional) resolution, can be designed, then a microscope having unprecedented high performance can be accomplished. Accordingly, there is a demand for a technique capable of realizing excellent 3D spatial resolution.

[X] Fluorescence Correlation Method

Fifthly, a fluorescence correlation method capable of making fluorescence analysis at a single molecular level has been known. Where a fluorescence analysis is performed by the prior art fluorescence correlation method using a double-resonance-absorption microscope, some problems remain to be solved. That is, where a pulsed light source such as a pulsed laser is used as a pulsed light source, it is quite difficult to precisely measure a fluorescence correlation function only depending on a fluorescent phenomenon. This problem will be described in further detail below. Accordingly, there is a demand for a novel fluorescence correlation method capable of precisely measuring a fluorescence correlation function relying only on a fluorescent phenomenon, even if a pulsed light source is used in a double-resonance-absorption microscope.

SUMMARY OF THE INVENTION

In view of the foregoing circumstances, the present invention has been made.

It is an object of the invention to provide a novel double-resonance-absorption microscope capable of generating a hollow erase light beam that is ideal for achieving super-resolution.

It is another object of the invention to provide a novel double-resonance-absorption microscope equipped with a light source having excellent operability and maintainability.

It is a further object of the invention to provide a novel double-resonance-absorption microscope capable of suppressing mixing of excitation light into a fluorescence signal thereby to achieve a higher S/N ratio.

It is still another object of the invention to provide double-resonance-absorption microscope having excellent three-dimensional spatial resolution.

It is a still further object of the invention to provide a novel fluorescence correlation method which can be used advantageously in a double-resonance-absorption microscope as well as in other systems using a pulsed light source and which can precisely measure fluorescence correlation functions relying only on fluorescence.

BRIEF DESCRIPTION OF THE DRAWINGS

The foregoing and other objects, features and advantages of the present invention will be better understood from the following detailed description, taken in conjunction with the accompanying drawings, in which:

FIG. 1 is a diagram illustrating the electronic arrangement of sample molecules in a ground state;

FIG. 4 is a diagram illustrating the electronic arrangement of deexcited sample molecules;

FIG. 6 is a conceptual diagram spatially illustrating an example of a double-resonance-absorption process;

FIG. 10 is a diagram illustrating the absorption characteristics (indicated by the solid line) and fluorescence characteristics (indicated by the dotted fine) of rhodamine 6G;

FIG. 12 is a diagram illustrating the principle of formation of erase light having a good beam profile using a spatial filter;

FIG. 19 is a schematic view of a phase plate used as a phase modulator;

FIG. 23 is a diagram showing a pulse stretcher optical system;

FIG. 31 is a schematic diagram of a further solid-state dye laser in accordance with the invention;

FIG. 32 is a conceptual diagram of a non-resonance-two-photon excitation process;

FIG. 35(a) is a conceptual diagram of a spatial resolution in a one-photon excitation process;

FIG. 35(b) is a conceptual diagram of a spatial resolution in a non-resonance, two-photon excitation process;

FIG. 37 is a diagram illustrating one example of timing at which irradiation and measurement are performed by a time division measurement method;

FIG. 39 is a diagram of fluorescence intensity distributions taken along the x-axis within a focal plane where a one-photon excitation process (indicated by the dotted line) and a non-resonance two-photon excitation process (indicated by the solid line) are used;

FIG. 40 is a diagram of fluorescence intensity distributions taken along the Z-axis in a system in which the origin is taken at a focal point where a one-photon excitation process (indicated by the dotted line) and a non-resonance two-photon excitation process (indicated by the solid line) are used;

FIG. 42 is a diagram showing the fluorescence intensity distribution taken in the X-axis direction within a focal plan where a non-resonance two-photon excitation process is used;

FIG. 43 is a diagram showing the fluorescence intensity distribution taken in the Z-axis direction where a non-resonance two-photon excitation process is used;

FIG. 44 is a conceptual diagram illustrating spatial resolution where a non-resonance two-photon excitation process is used;

FIG. 49 is a conceptual diagram illustrating the manner in which a region irradiated with pump light overlaps with a region irradiated with probe light;

FIG. 50 is a schematic diagram of optical systems for irradiating pump light and probe light;

FIG. 51 is a diagram of examples of intensity profile of pump light, probe light, and transient Raman scattering light;

FIG. 52(a) is a diagram illustrating resolution during a normal one-photon excitation process;

FIG. 52(b) is a diagram illustrating resolution during a transient Raman scattering process;

FIG. 54 is a schematic block diagram of one example of electrical system for controlling the double-resonance-absorption microscope shown in FIG. 53;

FIG. 61 is a further diagram illustrating the principle of the fluorescence correlation method in accordance with the present invention;

FIG. 62 is a schematic block diagram of a fluorescence correlation measurement system for achieving the fluorescence correlation method in accordance with the invention;

FIG. 64 is a schematic diagram of a double-resonance-absorption microscope.

DETAILED DESCRIPTION OF THE INVENTION

[I. a] Novel Double-Resonance-Absorption Microscope Capable of Generating a Hollow Erase Light Beam that Is Ideal for Achieving Super-resolution The present invention provides a double-resonance-absorption microscope having a pump light source for producing pump light having a wavelength of $\lambda_1$ for exciting molecules of a sample from a ground state to a first electronic excited state, an erase light source for producing erases light having a wavelength of $\lambda_2$ for exciting the sample molecules in the first electronic excited state to a second or higher electronic excited state, and an overlapping component for causing a region irradiated with the pump light to overlap with a region irradiated with the erase light. The pump light and erase light are directed to the sample via the overlapping component to partially suppress a region that emits light when the sample molecules in the first electronic excited state deexcite to the ground state. To produce super-resolution more effectively, the following spatial filter is used. For this purpose, the erase light is shaped into a hollow beam by an improved method.

Figure 11:
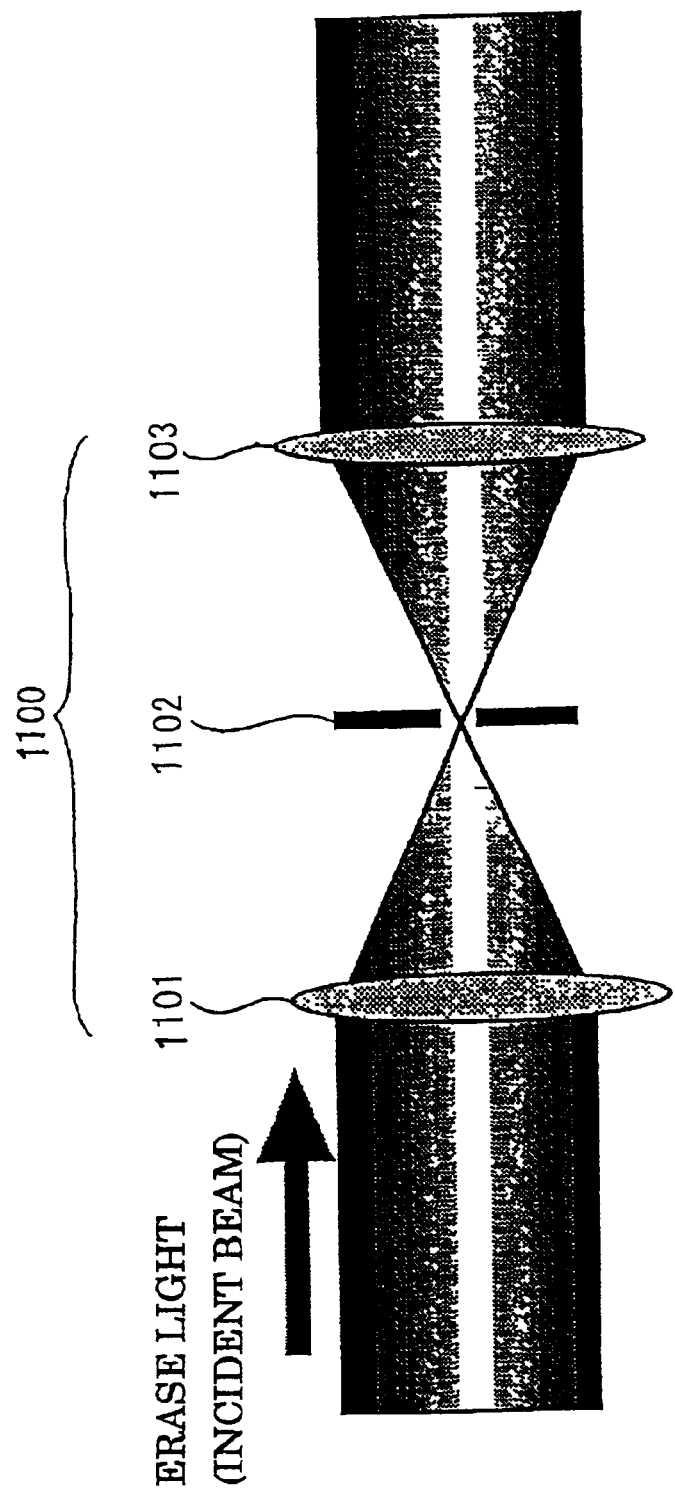
FIG. 11 is a conceptual diagram of a spatial filter used in a double-resonance-absorption microscope in accordance with the invention.

FIG. 11 is a conceptual diagram illustrating one example of a spatial filter 1100. This filter 1100 has a condenser lens 1101, a collimator lens 1103, and a pinhole 1102 formed between the lenses. Incident erase light is focused at the pinhole 1102 by the condenser lens 1101. Only the erase light that passes through the pinhole 1102 is collimated by the collimator lens 1103. In this geometry, laser light having disturbed wavefront cannot pass through the pinhole 1102. As a result, only laser light that is uniform in wavefront can pass through the pinhole 1102.

This principle is described by referring to FIG. 12, where an incident beam having a radius of h is directed to a pinhole which has a radius of a and is located at the focal plane of a lens having a focal distance of f.

We first discuss a wavefront arising from a point light source at a lens position (or a pupil position) $\xi_1$. Let $1_{1u}$ be the optical path length from the point $\xi_1$ to a fringe $Z_u$ of the pinhole that is closest to the point $\xi_1$. This optical path length is given by $$1_{1u} = n\sqrt{(h-a)^2 + f^2} \quad (1)$$

where n is the index of refraction of the optical path. Let $1_{1d}$ be the optical path length from the point $\xi_1$ to a fringe $Z_d$ of the pinhole that is most remote from the point $\xi_1$. This optical path length is similarly given by $$1_{1d} = n\sqrt{(h+a)^2 + f^2} \quad (2)$$

Therefore, the optical path difference between them is given by $$\Delta_1 = 1_{1d} - 1_{1u} = n\sqrt{(h+a)^2 + f^2} - n\sqrt{(h-a)^2 + f^2} \quad (3)$$

We expand this Eq. (3) into a Taylor series and take infinitesimal values up to 1. Thus, $$\Delta_1 \cong \frac{2nha}{f} \quad (4)$$

This $\Delta 1$ indicates the maximum deviation of the wavefront when light coming out of the point $\xi_1$ passes through the pinhole. At this time, the phase difference $\delta_1$ is given by $$\delta_1 \cong \frac{4\pi nha}{f\lambda} \quad (5)$$

where $\lambda$ is the wavelength of the light. This phase difference is a wavefront aberration and means that light producing a phase difference exceeding the phase difference given by Eq. (5) cannot pass through the pinhole.

The optical path length, $1_{0u}$, from a point $\xi_0$ on the optical axis to the fringe $Z_u$ is given by $$1_{0u} = n\sqrt{a^2 + f^2} \quad (6)$$

In this case, the maximum phase difference is the optical path difference with light passing on the optical axis.

Therefore, by performing a similar calculation, the phase difference $\delta_0$ is given by $$\delta_0 \cong \frac{\pi n a^2}{f\lambda} \quad (7)$$

In particular, where a laser beam as shown in FIG. 12 passes through a pinhole, the maximum phase difference that each light component emitted at each pupil plane produces assumes a value from $\delta_1$ to $\delta_0$. Consequently, if the whole beam passes through the pinhole, the beam passes through the pinhole with a phase delay of less than $\delta_1$. Therefore, even if the wavefront of the laser beam is disturbed, only laser light having phase differences of less than $\delta_1$ can be passed by providing the spatial filter 1100 shown in FIG. 11.

Figure 2:
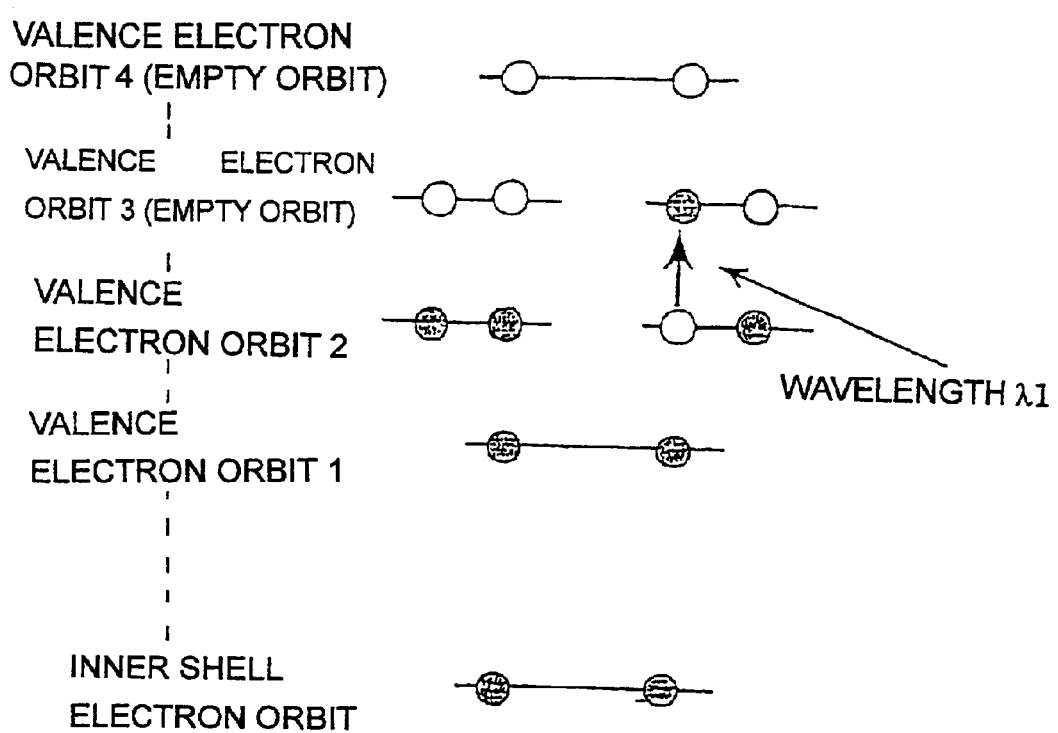
FIG. 2 is a diagram illustrating the electronic arrangement of sample molecules excited to state $S_1$.
Figure 3:
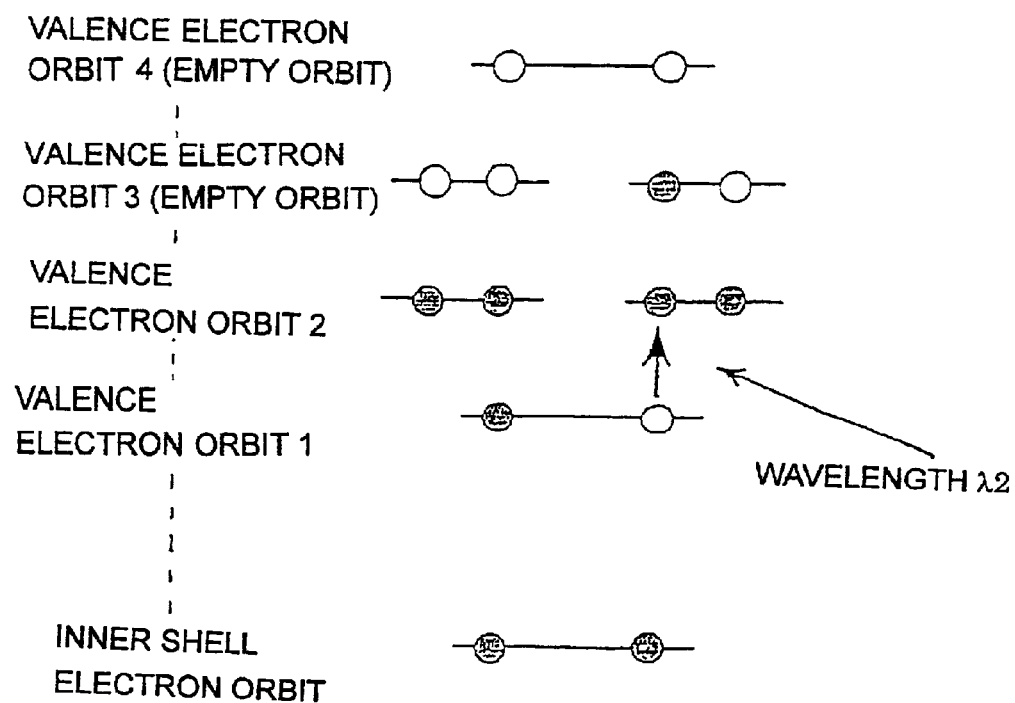
FIG. 3 is a diagram illustrating the electronic arrangement of sample molecules excited to state $S_2$.
Figure 5:
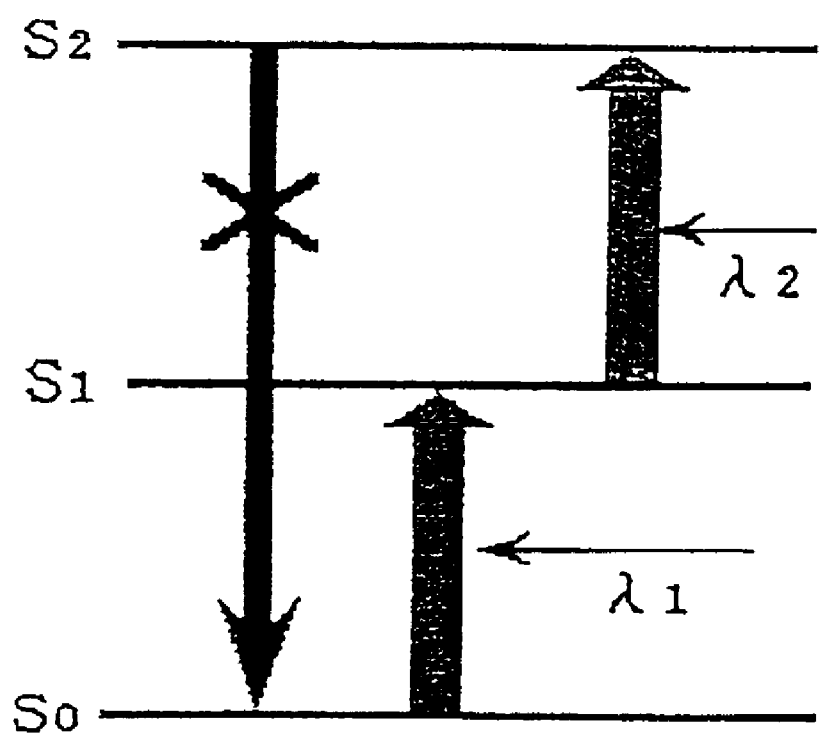
FIG. 5 is a conceptual diagram illustrating an example of a double-resonance-absorption process.
Figure 7:
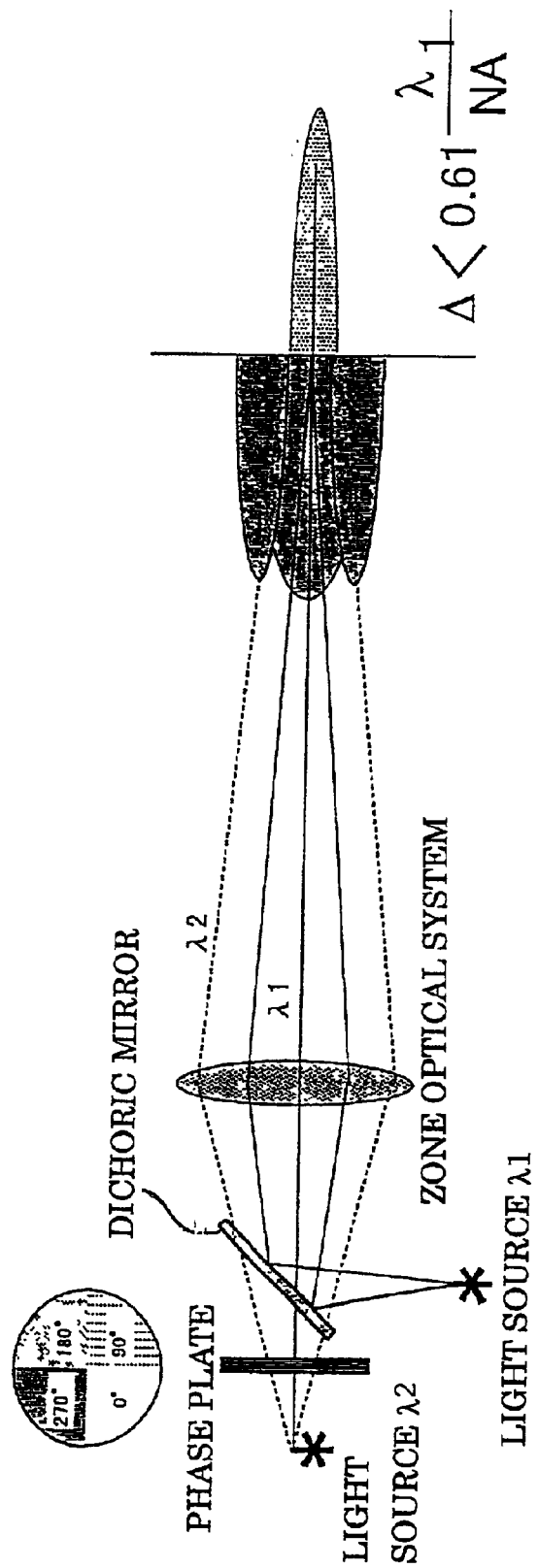
FIG. 7 is a conceptual diagram illustrating partial overlap of regions irradiated with pump light and erase light, respectively, as well as fluorescence suppression effected thereby.
Figure 8:
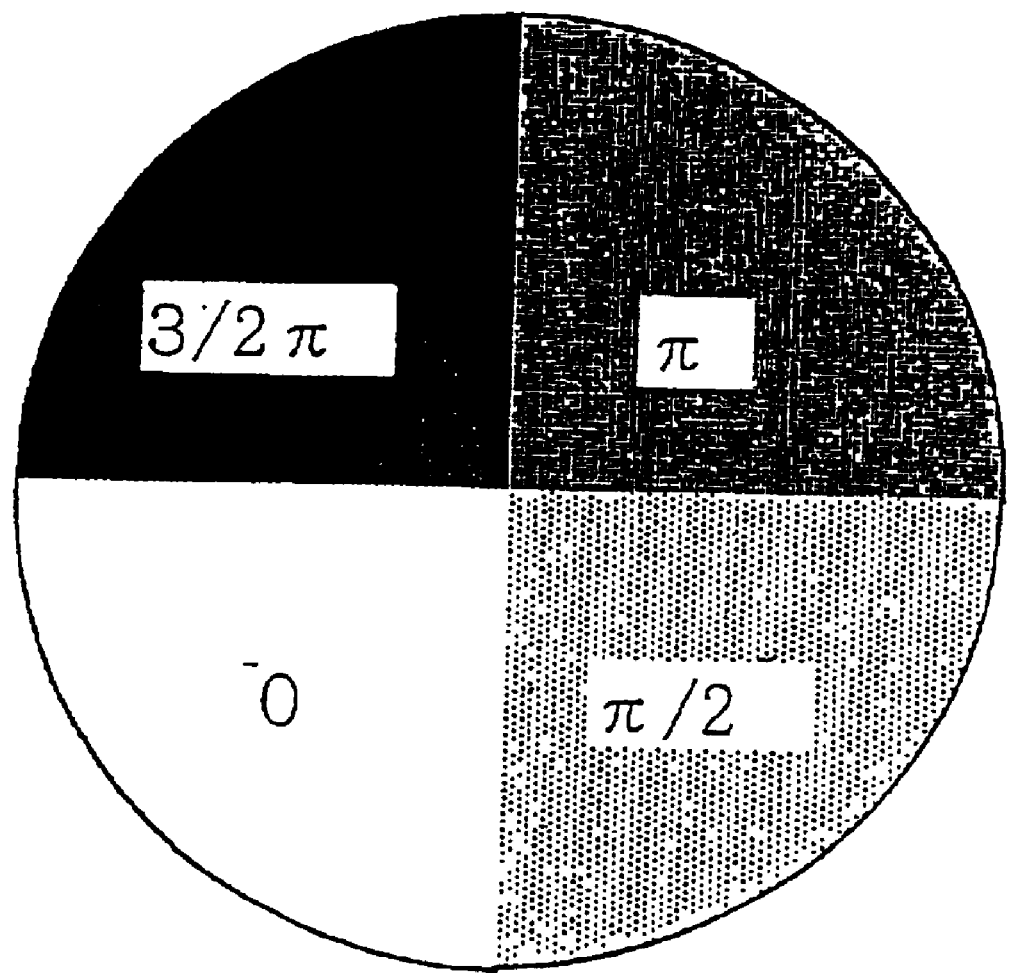
FIG. 8 is a diagram illustrating a phase plate used to make an erase light beam hollow.

This is described in connection with a case in which a hollow erase light beam is formed in a double-resonance-absorption microscope. Where a first-order Bessel beam whose electric field strength is zero in the vicinity of the optical axis is formed using the phase plate shown in FIG. 8, the electric field strengths will not cancel out on the optical axis and thus a good hollow beam shape is not obtained unless the phase difference of at least erase light hitting the phase plate is $\pi/2$ at positions symmetrical with respect to the optical axis. However, if the spatial filter 1100 of FIG. 11 is placed in the optical path of erase light having a wavelength of $\lambda_2$, the phase difference of the erase light can be set to less than $\delta_1$. In particular, if a phase plate satisfying the following condition is used, the electric field strengths associated with phase differences of the erase light are opposite at positions symmetrical with respect to the optical axis, and the field strengths weaken on the optical axis:

$$\frac{\pi}{2} > \frac{4\pi na}{f\lambda_2} \quad (8)$$

That is, a hollow erase light beam having a minimum necessary beam profile capable of realizing super-resolution can be generated. To create a condition for the pinhole 1102 forming the spatial filter 1100, we have $$a \leq \frac{f\lambda_2}{8nh} \quad (9)$$

where a is the radius of the pinhole, $\lambda_2$ is the wavelength of erase light, f is the focal distance of a condenser lens, n is the index of refraction of the optical path of the erase light, and h is the radius of the beam of the erase light. Eq. (9) is a condition for giving the size of the pinhole 1102. Rewriting Eq. (9) using the effective numerical aperture NA limited by the beam radius of the erase light, i.e., the pupil plane, gives rise to $$a \leq \frac{\lambda_2}{8nNA} \quad (10)$$

where a is the radius of the pinhole, $\lambda_2$ is the wavelength of erase light, n is the index of refraction of the optical path of the erase light, and NA is the effective numerical aperture of the condenser lens limited by the pupil plane.

Therefore, it is desired to use the pinhole 1102 satisfying the condition given by Eq. (9) or (10) as the spatial filter 1100 in the double-resonance-absorption microscope in accordance with the present invention. Only erase light having a beam profile with phase difference less than $\delta_1$ can be extracted by passing the light through this spatial filter 1100. Using this erase light, a hollow erase light beam suitable for generation of super-resolution can be created via a phase plate.

Eqs. (9) and (10) are conditions for the pinhole 1102. Numerical values such as the focal distance f of the condenser lens and the numerical aperture NA are used and so it can be said that these are conditions for the pinhole 1102 and for the condenser lens 1101 or conditions for the spatial filter 1100 itself.

EXAMPLE 1

Figure 13:
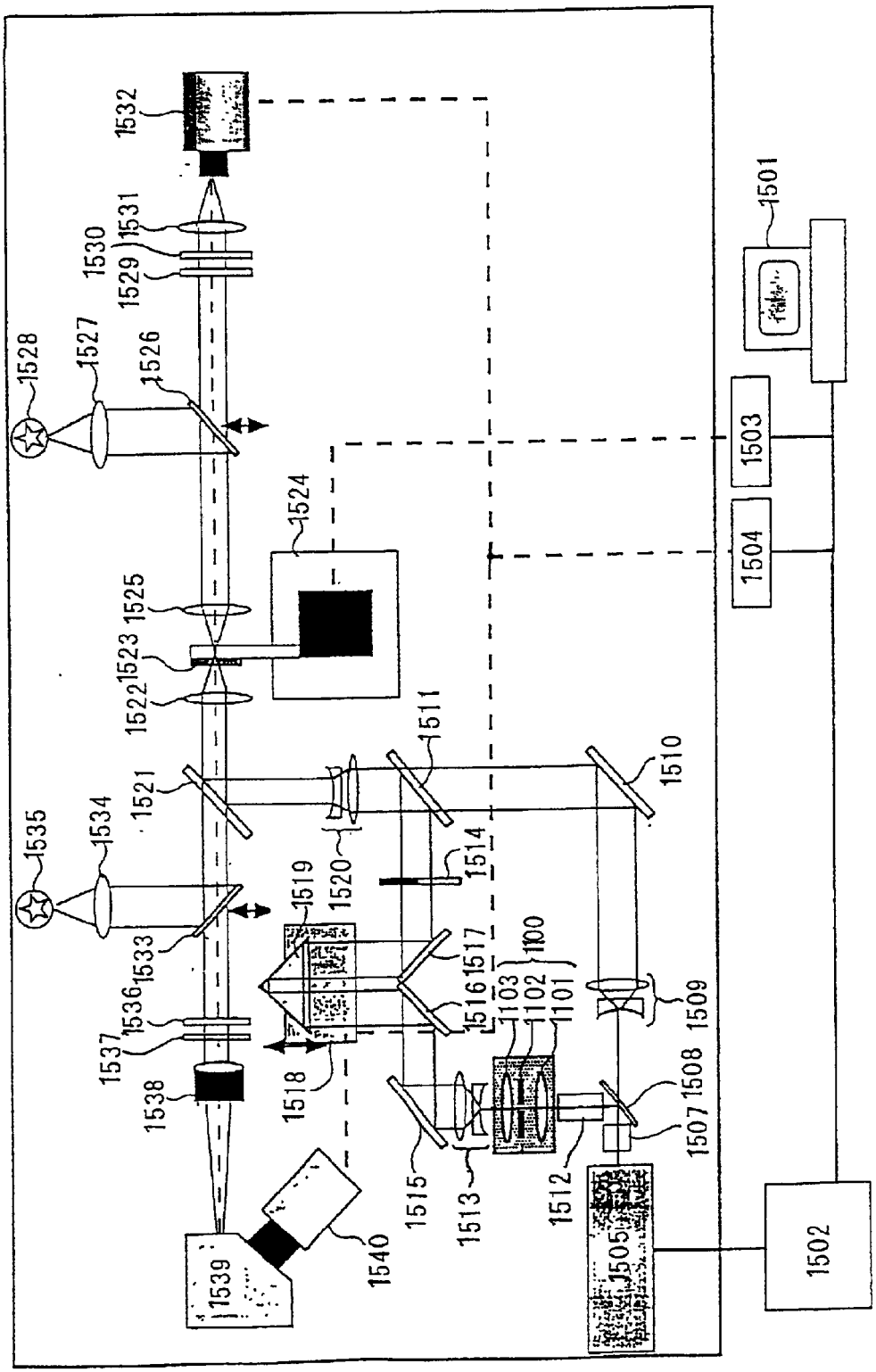
FIG. 13 is a schematic view of a laser scanning fluorescence microscope system using a double-resonance-absorption microscope, the microscope system forming one embodiment of the invention.

FIG. 13 is a schematic diagram of one example of the double-resonance-absorption microscope in accordance with the present invention. The illustrated double-resonance-absorption microscope forms a laser-scanning fluorescence microscope, and is a system for focusing pump light and erase light into spots, detecting fluorescence while scanning a sample 1523 and the spots relative to each other, and imaging the fluorescence signal using a computer 1501.

The whole system is controlled by the computer 1501, which controls the timing of lasing of an Nd:YAG laser 1505 that is a fundamental light source via a laser controller 1502. At the same time, the computer controls movement of a sample stage 1524 via a sample stage controller 1503 in synchronism with the timing of lasing of the laser to scan the sample 1523 in two dimensions. Concurrently, the fluorescence signal from the sample 1523 is taken from an ICCD camera 1540 via a camera controller 1504 in synchronism with the lasing of the laser.

In the present embodiment, it is assumed that the sample 1523 has been stained with fluorescence labeler molecules and that the fluorescence labeler molecules are rhodamine-based molecules. FIG. 10 shows spectral data about rhodamine 6G that is one kind of rhodamine-based molecule. As can be seen from this diagram, an absorption band corresponding to excitation $S_0 \rightarrow S_1$ exists near 530 nm and that excitation $S_1 \rightarrow S_2$ and a fluorescence band are present around 600 nm. Accordingly, fluorescent wavelengths other than 599 nm are made extinct by a double-resonance-absorption process and a stimulated emission process, which in turn are caused by excitation $S_0 \rightarrow S_1$ with pump light having a wavelength $\lambda_1$ of 532 mn and excitation $S_1 \rightarrow S_2$ with erase light having a wavelength $\lambda_2$ of 599 nm.

The light having the wavelength of 532 nm can be created by modulating the fundamental wave having a wavelength of 1064 nm from the Nd:YAG laser 1505 into its second-harmonic wave by a wavelength modulator 1507 consisting of a BBO crystal, KTP crystal, or the like. The light having the wavelength of 599 nm can be created by converting a wavelength of 532 nm to a wavelength 599 nm by a Raman shifter 1512 as made of $Ba(NO_3)_2$. The light with wavelength 532 nm from the wavelength modulator 1507 is split by a half mirror 1508. The transmitted light is enlarged into collimated light of appropriate size by a telescope 1509 and used as pump light. On the other hand, the reflected light is modulated into light having a wavelength of 599 nm by the Raman shifter 1512 and used as erase light.

Generally, an Nd:YAG laser 1505 has a resonator consisting of a gaussian mirror and, therefore, the wavefront is relatively uniform around the center, i.e., in the vicinity of the optical axis of the beam. However, the wavefront is disturbed at peripheral portions. The peripheral portions produce phase differences with the central portion. When one attempts to form a first-order Bessel beam, i.e., a hollow erase light beam, by making use of the whole diameter of the laser beam, a hollow beam suitable for realization of super-resolution cannot be obtained because of distortion of the wavefront, i.e., distortion of the phase plane.

In the present embodiment, therefore, the aforementioned spatial filter 1100 is placed in the optical path of the erase light behind the Raman shifter 1512. The light is passed through the spatial filter 1100. Thus, only erase light of a beam profile whose wavefront disturbance is suppressed to $\lambda_2/4$ or below can be extracted. Specifically, the radius of the erase light beam produced from the Raman shifter 1512 is set to 2 mm. The light beam is focused at the pinhole 1102 by the condenser lens 1101 having a focal distance f of 50 cm. In this case, the index of refraction n of the erase light in the optical path, i.e., the index of refraction n of air, is assumed to be 1.0. The radius a of the pinhole 1102 is found to be 38 $\mu$m using Eq. (9). Erase light passed through the pinhole 1102 is returned to a beam diameter of 2 mm by the collimator lens 1103 having the same focal distance f as that of the condenser lens 1101.

A perfect first-order Bessel beam can be created from erase light having a good beam profile obtained in this way. Specifically, erase light emerging from the spatial filter 1100 is enlarged into collimated light of appropriate size by a telescope 1513 and then formed into a first-order Bessel beam by a phase plate 1514.

Figure 14:
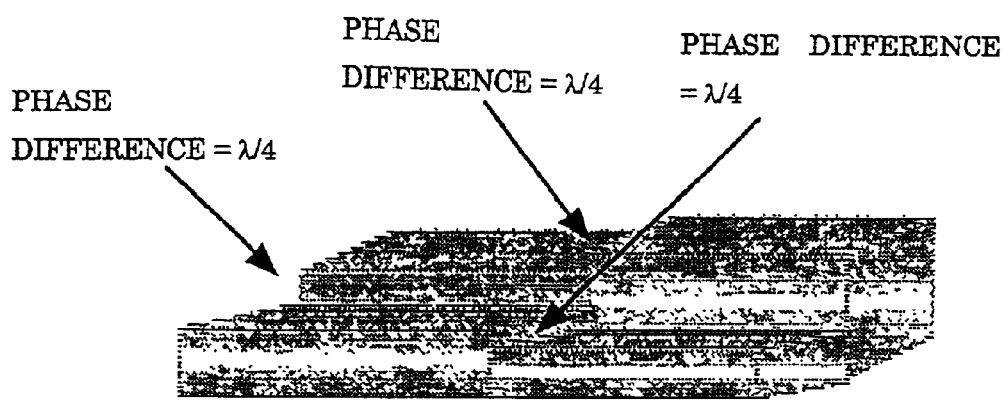
FIG. 14 is a schematic diagram showing one example of a phase plate fabricated by etching a glass substrate.

In the present embodiment, the wavelength $\lambda_2$ of the erase light is 599 nm and so the phase plate 1514 is fabricated by etching a glass substrate as shown in FIG. 14. Since the index of refraction of glass is 1.46 (at wavelength 599 nm), a quarter wavelength of the erase light corresponds to the thickness of 325.5 nm of the glass substrate. Accordingly, as shown in FIG. 14, the face of the phase plate 1514 is divided into four regions. The thickness is set so that the mutually adjacent regions produce a phase difference of a quarter wavelength, and then the glass is etched. Consequently, the erase light can be shaped into an ideal hollow beam. That is, the erase light is passed through the phase plate 1514 in such a way that the optical axis of the light is coincident with the center of the phase plate 1514. As a result, those portions of the erase light which pass through two opposite central portions of the phase plate 1514 are opposite in phase to each other. Therefore, the electric field intensity in the regions close to the optical axis is zero. As a consequence, erase light having a hollow beam profile that is ideal for developing super-resolution by fluorescence suppression can be obtained. The erase light shaped into a hollow beam in this way is a first-order Bessel beam.

Instead of fabricating the phase plate 1514 by etching, it may also be fabricated by depositing a thin film of magnesium fluoride or the like that gives a phase difference onto a substrate. Obviously, the order in which the Raman shifter 1512, the telescope 1513, and the phase plate 1514 are placed may be changed as long as an ideal erase light beam is obtained.

The pump light beam and the hollow erase light beam are reflected by reflective mirrors 1510 and 1515, respectively, and made to enter a beam combiner 1511, where both beams are made coaxial. Of course, both light beams are made equal in size by the telescopes 1509 and 1513. The sizes of the pump light and erase light that are made coaxial are adjusted to be equal to the diameter of a condenser objective lens 1522 by a beam reducer 1520 that is a kind of telescope optical system such that both light beams are accepted by the full aperture of the condenser objective lens 1522. The beams are focused onto a surface of a sample 1523 by the condenser objective lens 1522.

In the present embodiment, to adjust the time at which the pump light and the erase light arrive at the surface of the sample, the optical path length of the erase light can be adjusted. In particular, a delay optical system consisting of a translational motion stage 1518 and a prism 1519 carried on it is mounted on the side of a reflecting optical path formed by a reflecting mirror 1516. Erase light from the telescope 1513 is passed into the prism 1519 of the delay optical system via the reflecting mirrors 1515 and 1516. At this time, the translational motion stage 1518 is made to move a distance equal to the delay distance of the erase light relative to the pump light. In this way, the distance that the erase light travels in its path bent by the prism 1519 is adjusted. The delay distance is 30 cm where the arrival time difference is 1 nsec. This delay distance can be measured by a micrometer, for example. The results of the measurement may be reflected in the distance traveled by the translational motion stage 1518. In this way, the irradiation time of the pump light completely overlaps that of the erase light. Hence, illumination optimal for suppression of fluorescence is enabled. Where two independent lasers (e.g., two Nd:YAG pulsed lasers) are used as the light sources of the pump light and the erase light, for example, the times at which the pump light and the erase light arrive at the sample 1523 can also be adjusted by electrically controlling Q-switching signals for the light sources, respectively.

Where the pump light and the erase light are made to hit the sample 1523 in this way, an illuminated region in which both light beams overlap forms a fluorescence-suppressed region $A_1$, because the hollow erase light overlaps a part of the region irradiated with the pump light. The region that is irradiated with the central hollow portion of the hollow erase light and thus irradiated only with the pump light forms a fluorescence region $A_0$ (see FIG. 6). Rhodamine-based molecules fluoresce only from this fluorescence region $A_0$ that is an observed region.

Figure 15:
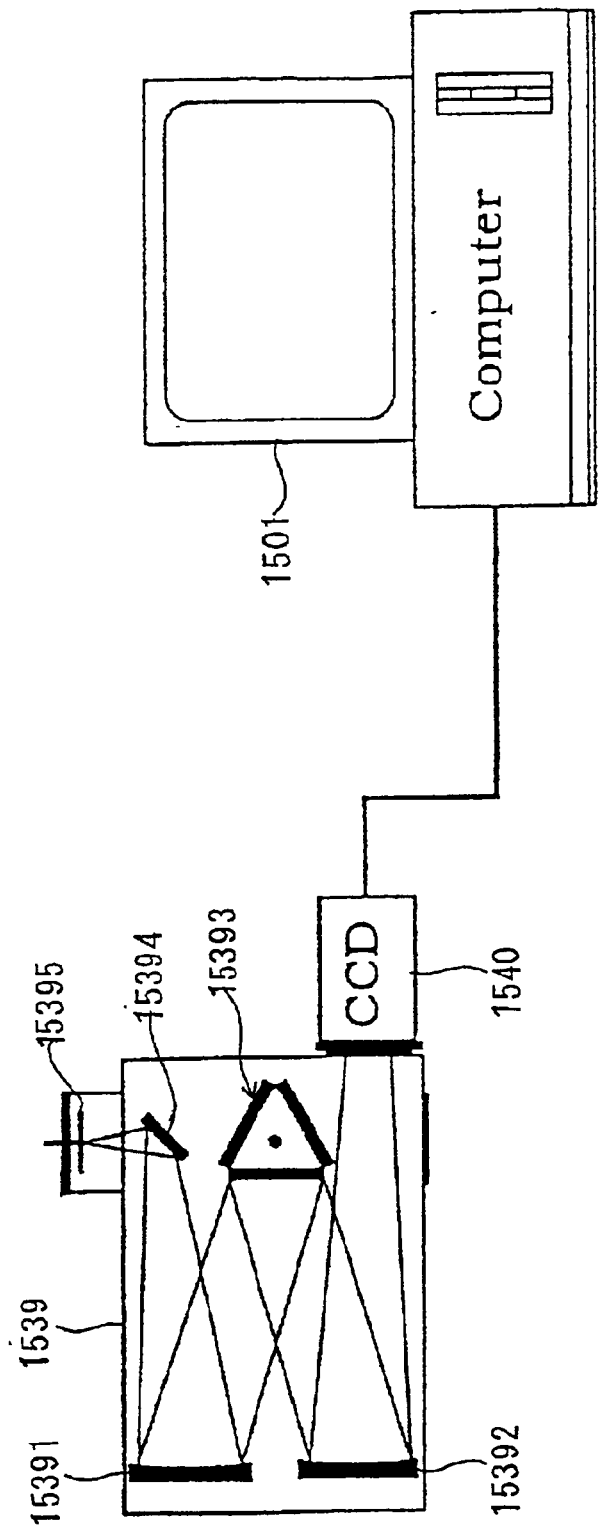
FIG. 15 is a schematic diagram showing the internal structure of a spectroscope used in the microscope system shown in FIG. 13.

The emitted fluorescent light again passes through the condenser objective lens 1522 and enters a spectroscope 1539 via an eyepiece lens 1538. As shown in FIG. 15, the spectroscope 1539 includes a collimator spherical mirror 15391, a focusing spherical mirror 15392, and a mechanically switchable diffraction grating 15393 as its fundamental optical components. Fluorescent light passed through an incident slit 15395 is directed to the collimator spherical mirror 15391 by a reflecting mirror 15394. The light is focused onto the diffraction grating 15393 by the collimator spherical mirror 15391. The fluorescent light that is wavelength-resolved on the diffraction grating 15393 is focused onto the CCD elements of the ICCD camera 1540 by the focusing spherical mirror 15392.

A signal obtained by the ICCD camera 1540 at this time is a fluorescence spectrum per shot of the laser. The sample stage 1524 is moved in two dimensions in synchronism with a shot of the laser. The resulting fluorescence spectra are accumulated and imaged by the computer 1501, whereby a two-dimensional fluorescence image of the sample 1523 can be created. If the pump light and the erase light are mixed into the fluorescence signal, the signal of the wavelength components of the pump light and the erase light are removed during the image creation process by the computer 1501. The image is created using only the genuine fluorescence wavelength component. Thus, a fluorescence image with sufficient super-resolution and high S/N can be derived.

To improve the super-resolution further, a notch filter 1536 for cutting the pump light wavelength and a notch filter 1537 for cutting the erase light wavelength maybe inserted before the spectroscope 1539. In FIG. 13, they are inserted before the eyepiece lens 1538 at the entrance of the spectroscope 1539. In this manner, the pump light and the erase light can be separated from the fluorescence signal before entering the spectroscope 1539. Only the genuine fluorescence component can be subjected to spectral analysis. Hence, the purity of the fluorescence signal can be enhanced. Super-resolution can be developed more effectively. Of course, if necessary, a bandpass filter and a sharp cut filter may be inserted in addition to the notch filters 1536 and 1537 to cut unwanted wavelength components other than the fluorescence from the fluorescence labeler molecules.

If the incident slit 15395 of the spectroscope 1539 opened, and if the zeroth-order light from the diffraction grating 15393 is focused onto the CCD elements of the ICCD camera 1540, then a fluorescence image from the surface of the sample 1523 is directly obtained. Especially, in this case, insertion of the aforementioned notch filters 1536, 1537, and a bandpass filter or a sharp cut filter is desirable, because the S/N can be improved.

A sample-moving mechanism in accordance with the present invention is next described. The sample stage 1524 that is controlled by a computer as mentioned previously can move in five dimensions, i.e., in the directions of X, Y, Z, $\phi$, and $\theta$.

First, an inch worm stage mechanism that is one kind of piezoelectric device is preferably used for movement in the Z-direction (i.e., the direction of the optical axis). The absolute position can be monitored by a rotary encoder.

Generally, where light is condensed by an objective lens having a large numerical aperture, the depth of focus becomes very shallow. This makes it very difficult to search for the focal point. For example, where light is focused by a lens having a numerical aperture of NA, the spread d of the focused beam at a point at a distance of $\delta z$ from the focus is given by $$d = \delta z \cdot NA \tag{11}$$

Assuming that the distance $\delta z$ is 600 nm, the spread d is about 400 nm, which is comparable to a size obtained where the pump light is focused to the limit of diffraction. This means that the position needs to be controlled at an accuracy of less than 1 $\mu$m. An inch worm stage using one kind of piezoelectric device permits submicrometer position control and so the inch worm stage is adapted for a double-resonance-absorption microscope in accordance with the present invention. Furthermore, the observed region can be quickly found if the sample 1523 is replaced, because the absolute position is being monitored.

Figure 16:
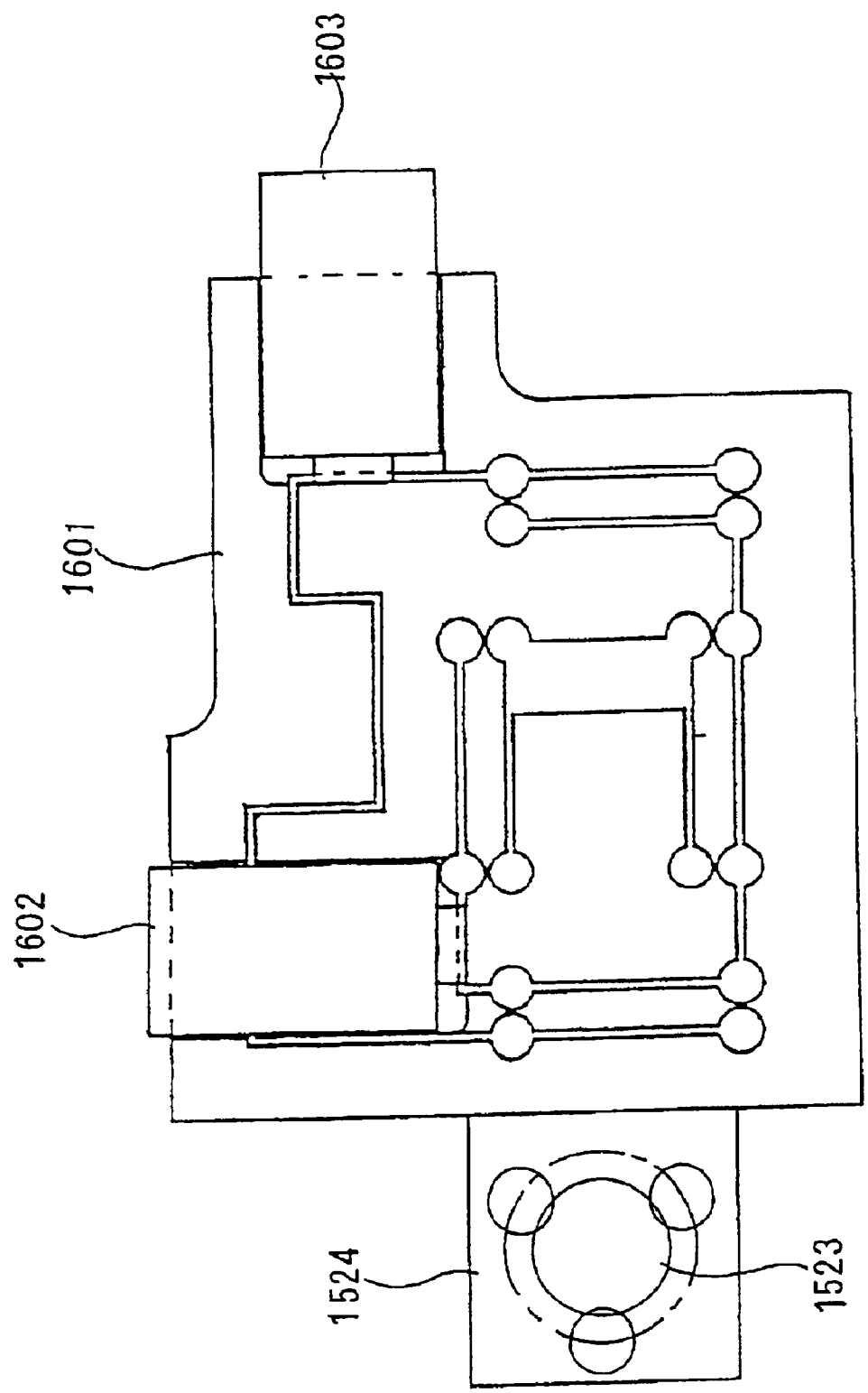
FIG. 16 is a schematic diagram showing an XY-translational mechanism for translating the sample stage of the microscope system shown in FIG. 13 in two dimensions.

FIG. 16 shows one example of a two-dimensional motion mechanism for moving the sample stage 1524 in the X- and Y-axis directions. This illustrated two-dimensional motion mechanism comprises a leaf spring 1601 and two laminar piezoelectric elements 1602, 1603. The piezoelectric elements 1602 and 1603 drive the leaf spring 1601. One laminar piezoelectric element 1602 moves the sample stage 1524 in the X-axis direction, while the other laminar piezoelectric element 1603 moves the stage 1524 in the Y-axis direction. In this way, the sample stage 1524 is moved in two dimensions within the plane perpendicular to the optical axis.

Figure 17:
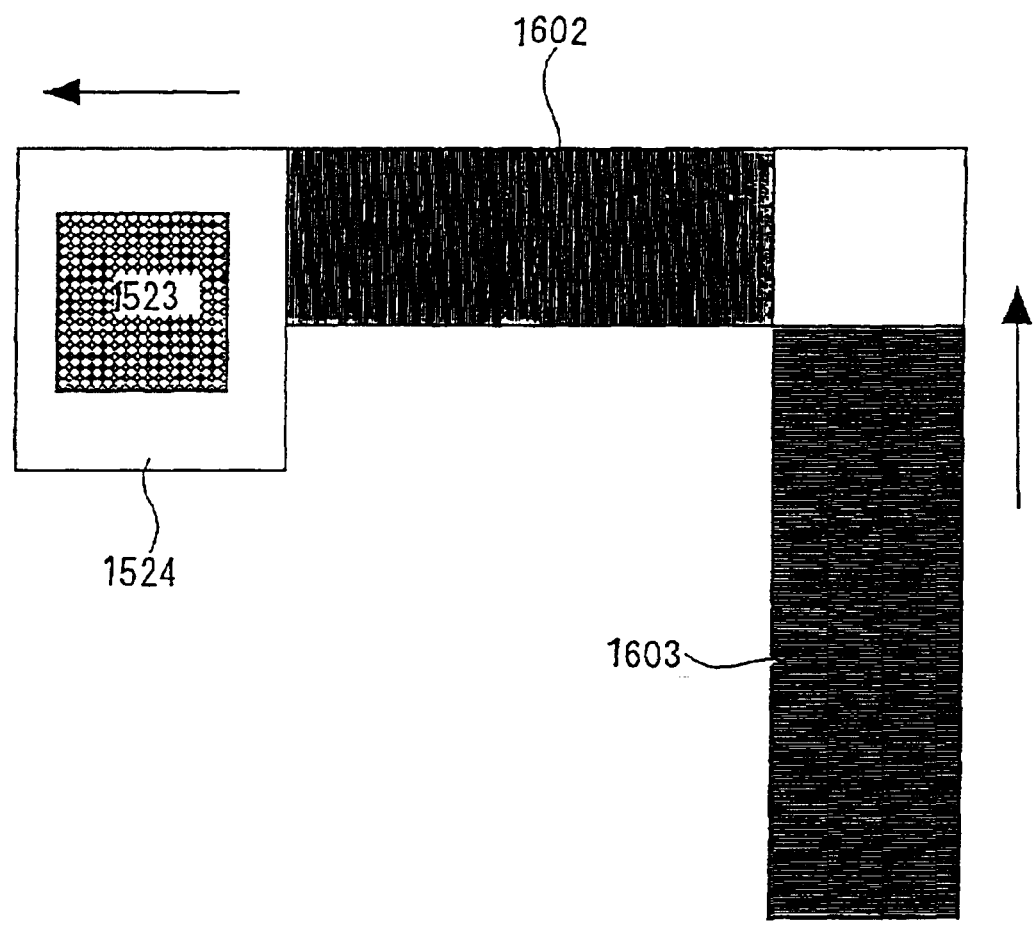
FIG. 17 is a schematic diagram showing another XY-translational mechanism for translating the sample stage in two dimensions.

As shown in FIG. 17, a moving mechanism comprising the sample stage 1524 on which laminar piezoelectric elements 1602 and 1603 are directly mounted may also be used. Note that the mechanism using the leaf spring 1601 as shown in FIG. 16 can more effectively prevent deterioration of the image quality due to distortion of the scanned surface.

The sample stage 1524 is equipped with driver mechanisms for movement in the θ and φ directions. These are added such that the optical axes of the pump light and of the erase light cross the surface of the sample 1523 accurately perpendicularly.

The sample stage 1524 relying on the five-dimensional movement mechanism constructed as described thus far is based on mechanical scan relative to the sample 1523. The laser beam itself may also be scanned by mounting a swinging galvano mirror, for example, in the path.

One example of adjustment of the optical axes of the pump light and erase light is described. A reference sample used to adjust the optical axis is prepared by dispersing rhodamine B in a thin film that is transparent to both pump light and erase light. Both pump light and erase light produce excitation $S_0 \rightarrow S_1$ at a high probability in rhodamine B and, therefore, a sufficient amount of fluorescent light can be observed. The thin film of this reference sample can be prepared, for example, by dispersing rhodamine B in PMMA in a solution state and spin-coating it on a slide glass to a thickness of several micrometers.

Procedures for the optical axis adjustment are effected as follows. The pump light and the erase light are simultaneously directed to the aforementioned reference sample. The position of the focal point is moved by adjusting the tilt of the reflecting mirror 1510 in the optical path of the pump light or the tilt of the reflecting mirror 1515 in the optical path of the erase light to bring the focal point of the pump light into agreement with the focal point of the erase light while observing the emitted fluorescent light by the computer 1501 via the ICCD camera 1540. When the focal points of the pump light and the erase light are coincident with each other, the emission area is minimal and the emission intensity is maximal. Therefore, the optical axes of the pump light and the erase light are aligned by adjusting the optical axis so as to produce such a fluorescence image.

In FIG. 13, a half mirror 1533, a lens 1534 for illuminating light, and an illuminating light source 1535 are optical components used to adjust the optical axes.

Referring still to FIG. 13, another microscope optical system for optical axis adjustment may be mounted behind the sample 1523. Also shown in FIG. 13 are a lens 1525 for transmitted light, a half mirror 1526, a lens 1527 for illuminating light, an illuminating light source 1528, a notch filter 1529 for cutting the pump light, another notch filter 1530 for cutting the erase light, an eyepiece lens 1531, and an ICCD camera 1532. These components form the microscope optical system for adjusting the optical axes.

The whole system described above is controlled in the manner described below. The microscope system in accordance with the present embodiment is equipped with an electrical control unit having a camera controller 1504 for controlling the ICCD camera 1540, a sample stage controller 1503 for controlling the sample stage 1524, and a laser controller 1502 for controlling the Nd:YAG laser 1505. Where the above-described microscope optical system for the optical axes is also mounted, the camera controller 1504 also controls the ICCD camera 1532. All of these controllers are under control of the computer 1501.

With respect to the ICCD camera 1540, a gate pulse that determines the time for which a fluorescence signal is detected is produced, and the obtained fluorescence signal is sent to the computer 1501. With respect to the sample stage 1524, the piezoelectric elements 1602 and 1603. (see FIGS. 16 and 17) are moved in steps. With respect to the Nd:YAG laser 1505, the Q-switching signal is controlled. A cycle of sequence of processing for the system consists of the following operations:

1. Lasing of Nd:YAG laser
2. Gate pulse generation for the ICCD camera
3. Acceptance of data
4. Stepwise movement of the piezoelectric elements This cycle is repeated a number of times corresponding to the number of pixels of the gained image. A fluorescence spectrum made up of individual pixels from the ICCD camera 1540 is accepted as numerical data into the computer 1501. After gaining the data about all the pixels, the wavelength components of the pump light and erase light mixed as background signals are removed by numeral processing. A value obtained by integrating other wavelength components is taken as an image signal about one pixel. The image data obtained in this way is sent to an external output device such as a CRT or a printer and stored in a storage device as in a HDD or FDD.

As described thus far, the present invention can offer a novel double-resonance-absorption microscope which is capable of generating a hollow erase light beam ideal for providing super-resolution and which can accomplish super-resolution more reliably.

[I.b] Another novel Double-Resonance-Absorption Microscope capable of generating a hollow erase light beam ideal for providing super-resolution is described below.

The present invention provides a double-resonance-absorption microscope having a pump light source for producing pump light having a wavelength of $\lambda_1$ for exciting molecules of a sample from a ground state to a first electronic excited state, an erase light source for producing erase light having a wavelength of $\lambda_2$ for exciting the sample molecules in the first electronic excited state to a second or higher electronic excited state, and an overlapping component for causing a region irradiated with the pump light to overlap with a region irradiated with said erase light. The pump light and erase light are directed to the sample via the overlapping component to partially suppress a region that emits light when the sample molecules in the first electronic excited state deexcite to the ground state. The manner in which the hollow beam is formed is improved. In addition, to produce super-resolution more effectively, detection of fluorescence signal and irradiation of pump light and erase light are improved. Furthermore, where a double-resonance-absorption microscope is used as a laser-scanning microscope by the use of lasers as the pump light source and the erase light source, respectively, laser scanning is improved.

[I.b-1] Generation of a Hollow Beam, [I.b-2] Detection of a Fluorescence Signal, [I.b-3] Irradiation of Pump Light and Erase Light, and [I.b-4] Laser Scanning are described below in turn.

[I.b-1] Generation of A Hollow Beam

In a double-resonance-absorption microscope in accordance with the present invention, the erase light necessary to provide super-resolution is shaped into a hollow beam by removing disturbance of the phase of the erase light source. Otherwise, the beam profile of the erase light would be distorted. This can be accomplished by using a coherent light source as the erase light source and suppressing disturbance of the phase of coherent light acting as erase light from the coherent light to less than $\lambda_2/2$.

According to the diffraction theory of optics, the intensity profile I (x, y, z) where collimated laser light is focused by a stigmatic optical system is given by $$I(x, y, z) = \left| \int_N \int_A e^{-im\phi} e^{-i\frac{2\pi}{\lambda} V(x,y,z,\xi,\zeta,\eta)} d\xi d\zeta \right|^2 \quad (12)$$

-continued where $$V(x, y, z, \xi, \zeta, \eta) = \sqrt{(x-\xi)^2 + (y-\zeta)^2 + (z-\eta)^2} - \sqrt{x^2 + y^2 + (z-f)^2}$$

where f is the focal distance of the optical system, λ is the wavelength of focused light, a point (x, y, z) is an observed point, (ξ, ζ, η) is a variable of integration, the. integrated region is equal to the whole of the pupil plane of the optical system, and φ is an angle taken about the optical axis on the pupil plane.

Figure 9:
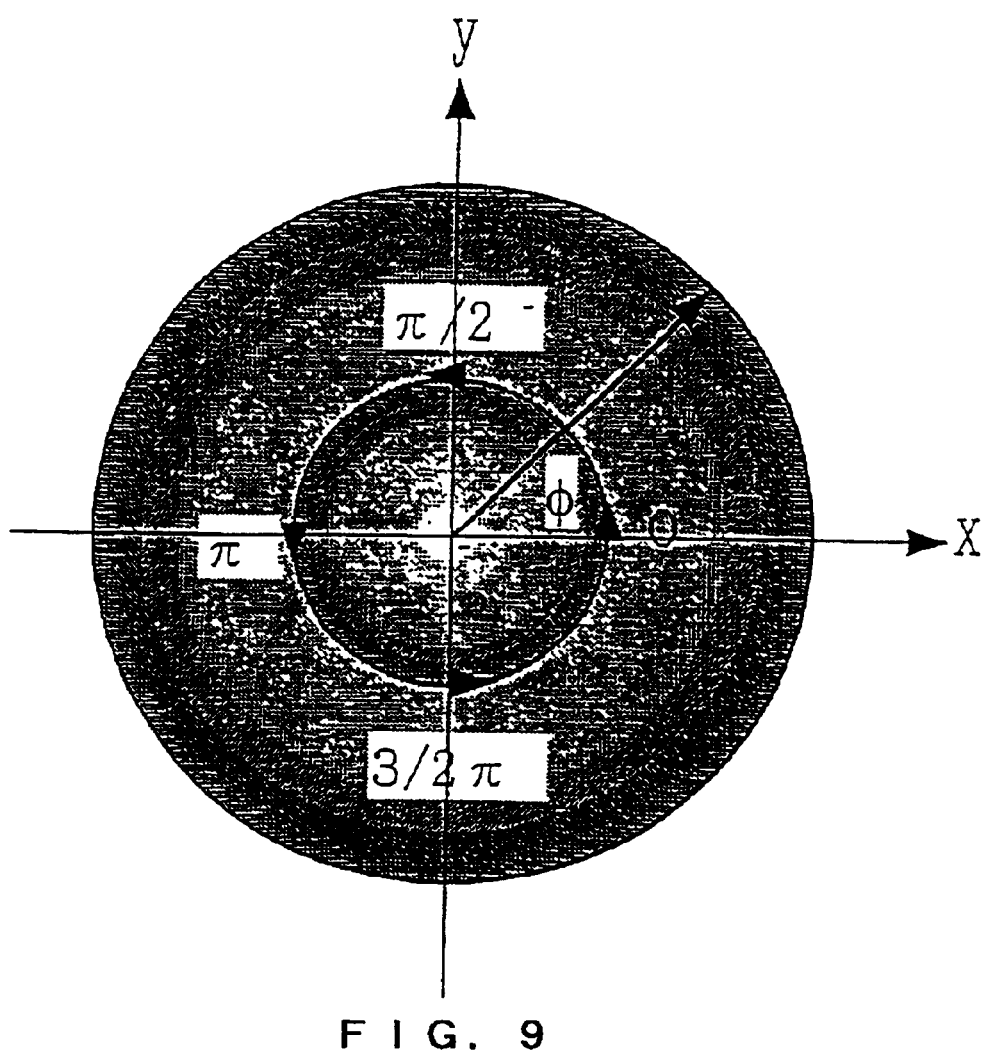
FIG. 9 is a conceptual diagram illustrating the phase distribution in a cross section of a first-order Bessel beam whose origin is located on the optical axis.

If the boundary condition that the pupil plane is symmetrical with respect to the axis holds, and m=1 is inserted into Eq. (12), then the intensity profile of focused first-order Bessel beam is obtained. If m=0 is inserted, then the intensity profile of an ordinary laser beam is obtained. As illustrated in FIG. 9, for the first-order Bessel beam, if one revolution is made about the optical axis, the phase varies by 2π. Theoretically, at two points that are symmetrical with respect to the optical axis, their phases are shifted by 2π with respect to each other. Therefore, the electric fields cancel out each other completely. Hence, the resultant electric field strength is zero. However, where the actual wavefront of the laser beam is not uniform, the fields do not cancel out completely, and electric field strength components appear on the optical axis. Therefore, if the wavefront of the laser beam is not uniform, it cannot be said that even the first-order Bessel beam is erase light ideal for a double-resonance-absorption microscope. Especially, where wavefront disturbance is so large that the phase difference between points symmetrical with respect to the optical axis is greater than λ/2, there is the possibility that the electric field strengths are identical in sign. This makes it difficult to form an ideal hollow beam.

Therefore, in order to form a hollow erase light beam adapted for creation of super-resolution, it is necessary to suppress the wavefront disturbance within the plane of the laser beam to λ/2 or less. In other words, distortion of the beamprof ile can be eliminated by using a coherent light source such as a laser and suppressing the wavefront disturbance within the plane of the laser beam to $\lambda_2/2$ or less. Consequently, a hollow erase light beam optimal for realization of super-resolution can be obtained.

To suppress the wavefront disturbance within the plane of the laser beam to $\lambda_2/2$ or less, regions in which the disturbance of phase wavefront in coherent light is greater than $\lambda_2/2$ are eliminated, and only the other regions are extracted. The beam of the extracted regions is used as erase light. This extraction of certain regions can be accomplished by placing a beam region-limiting means having a slit of adjustable width or an adjustable aperture in the optical path of the erase light. That is, only the required regions of the erase light are extracted by adjusting the width of the slit or the diameter of the aperture, it being noted that the light passes through the slit or the aperture. The adjusted range is determined by the used coherent light source.

Where a laser having a resonator using a gaussian mirror is used as a coherent light source, for example, only the central portion of the laser beam is used by cutting peripheral portions of the laser beam, because the optical characteristics of the gaussian mirror are such that the phase wavefront of the laser beam is quite uniform around the central portion, i.e., in the vicinity of the optical axis, but the phase waveform is disturbed to a greater extent in going away from the center. As a consequence, coherent light in which the phase disturbance within the plane of the beam is suppressed to $\lambda_2/2$ or less is accomplished. This can be used as erase light having a good beam profile.

Figure 18:
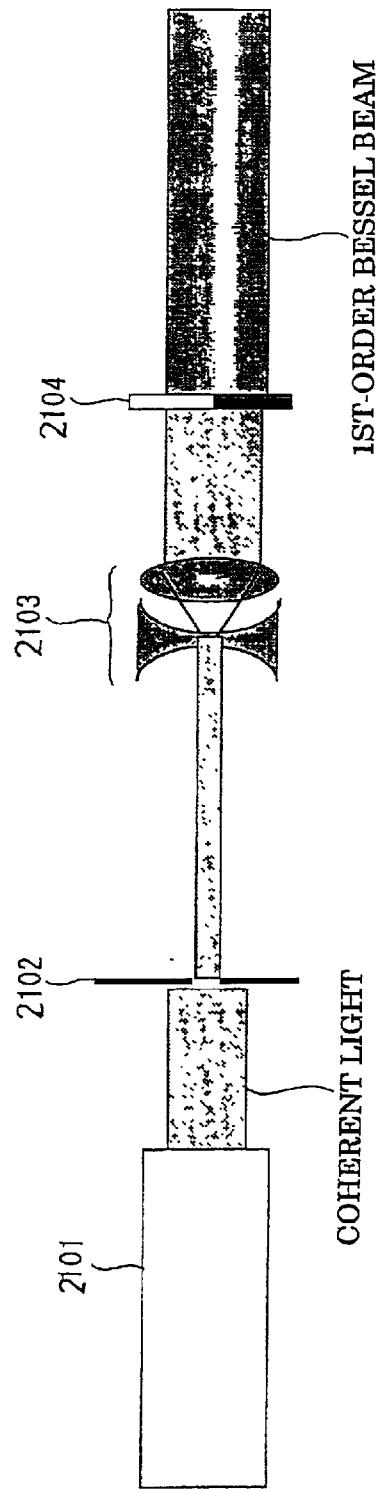
FIG. 18 is a schematic diagram illustrating an example of a method of shaping an erase light beam into a hollow beam (first-order Bessel beam)

FIG. 18 is a schematic diagram of one example of an optical system for accomplishing the aforementioned erase light. In the example of FIG. 18, a beam region-restricting means 2102 such as an iris diaphragm or a pinhole plate is placed on the exit side of a coherent light source 2101. Only regions in which the phase disturbance is less than a $\lambda_2/2$ are extracted from the erase light by adjusting the diameter of the iris diaphragm or pinhole plate.

Referring still to FIG. 18, a beam diameter-enlarging optical element 2103 and a phase modulator 2104 are placed in the optical path of the erase light. In this geometry, the erase light passed through the beam region-limiting means 2102 is enlarged in beam diameter by the beam diameter-enlarging optical element 2103. In addition, the phase plate is modulated by the phase modulator 2104.

More specifically, a telescope can be used as the beam diameter-enlarging optical element 2103. On the other hand, the phase modulator 2104 gives a spatial phase distribution within the cross section of the beam of the erase light. One example of this phase modulator 2104 gives a phase difference of π to the erase light about the optical axis. That is, the phases of coherent light at points that are symmetrical with respect to the optical axis are shifted in phase by π with respect to each other. In this case, the phase modulator 2104 can be a phase plate as shown in FIG. 19. The face of the illustrated phase plate is circumferentially divided into four equal regions that are shifted in phase by π/2 with respect to each other. This simplifies a structure acting to shift phase by 2π if rotated once about the optical axis. The erase light whose diameter is increased to a size appropriate for this phase plate by the beam diameter-enlarging optical element 2103 (such as a telescope) passes through the phase plate. As a result, the beam becomes a first-order Bessel beam. As mentioned previously, this first-order Bessel beam is created from erase light having a good beam profile, i.e., whose phase disturbance within the plane of the beam is suppressed to $\lambda_2/2$ or less by the beam region-restricting means 2102. Consequently, this is optimal as hollow erase light for accomplishing super-resolution in a double-resonance-absorption microscope.

This phase modulator 2104 can be a parallel substrate that is optically flat for the erase light, for example. Preferably, this substrate is transparent. An optical thin film having a thickness distribution that gives a phase difference of π to the erase light about the optical axis is coated on the substrate. The phase modulator may also be a similar parallel substrate etched to give a phase difference of n to the erase light about the optical axis. The phase plate of FIG. 19 is so constructed that an optical thin film having such a thickness distribution that the thickness differs among regions is coated or the substrate is etched.

Figure 20:
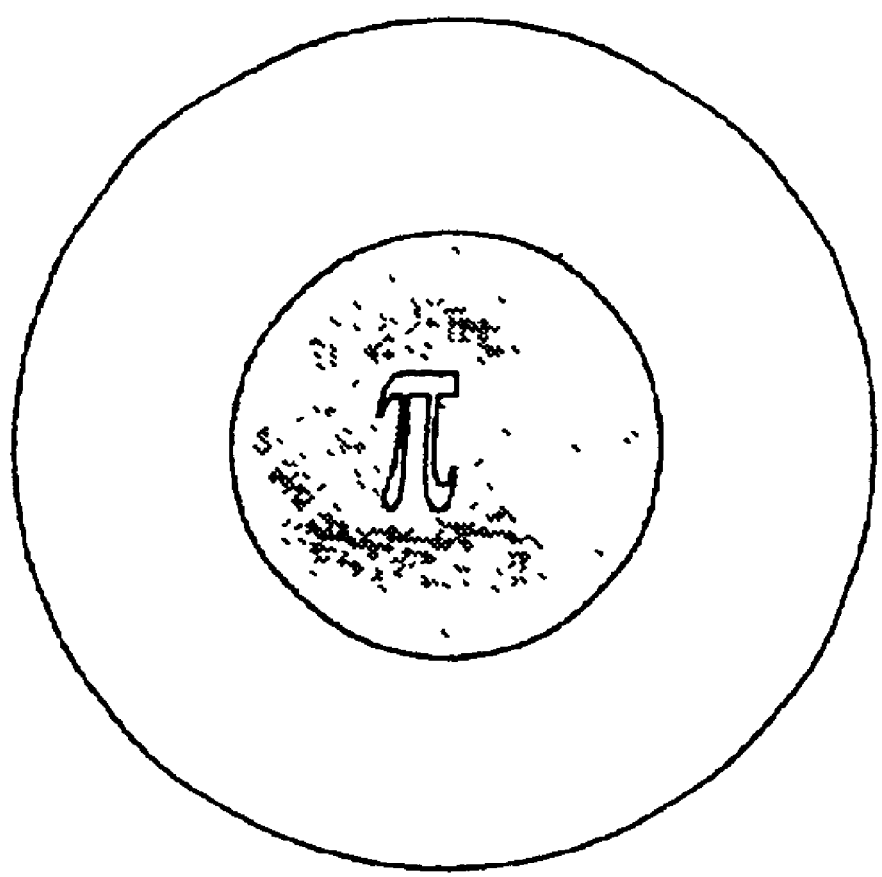
FIG. 20 is a schematic view of another phase plate used as a phase modulator.

The aforementioned phase modulator 2104 can be constructed in a different manner. For example, the phase modulator 2104 for giving a spatially coaxial phase distribution to the erase light passed through the beam region-limiting means 2102 within the cross section can also be employed. As shown in FIG. 20, a phase modulator 2104 consisting of a circular inner region and an annular outer region may also be used. This modulator gives a spatial phase distribution producing a phase difference of π. Also, in this case, erase light in the form of a hollow beam optimal for a double-resonance-absorption microscope can be accomplished. That is, the circular inner region and the annular outer region are opposite in phase and, therefore, if this beam is focused by a lens, the electric fields are canceled out in the center. As a result, a good hollow beam can be created. For this purpose, it is necessary to adjust the ratio of the area of the inner circle to the area of the annular outer portion.

In this case, the phase modulator 2104 can be a parallel substrate that is optically flat for the erase light. An optical thin film having a thickness distribution that gives a spatially coaxial distribution within the plane of the cross section of the beam to the erase light is coated on the substrate. Preferably, this substrate is transparent. The phase. modulator may also be a similar parallel substrate on which an optical thin film having a thickness distribution is coated. This thickness distribution can give a spatial phase distribution having a phase difference of it between a circular region and an outer annular region. For instance, this can be a phase plate. Furthermore, the phase modulator can be a similar parallel substrate capable of giving a spatially coaxial phase distribution within the plane of the cross section to the erase light. In addition, the phase modulator can be a similar parallel substrate etched to give such a spatial phase distribution that a phase difference of $\pi$ is created between a circular region and an outer annular region. For example, this can be a phase plate.

[I.b-2] Detection of Fluorescence Signal

In a double-resonance-absorption microscope in accordance with this invention, erase light having a very good hollow beam profile as described above is made to overlap with the pump light to thereby partially suppress the fluorescence region. This gives rise to super-resolution. In this case, however, the fluorescence region that is an observed region is restricted to a very narrow range of less than tens of nanometers, for example. The number of fluorescent molecules diffused in this infinitesimal, observed region is extremely small. The result is that the intensity of the emitted fluorescence is low. For this reason, a high-sensitivity fluorescence detection technique is necessary. Also, depending on sample molecules or fluorescencelabeler molecules, the wavelength of the pump light or the wavelength of the erase light may overlap the fluorescence band. Stray light from the pump light or erase light may be mixed in the fluorescence signal. Therefore, to obtain a microscope image with high S/N, a technique for separating unwanted light from the fluorescence signal is necessary.

Figure 21:
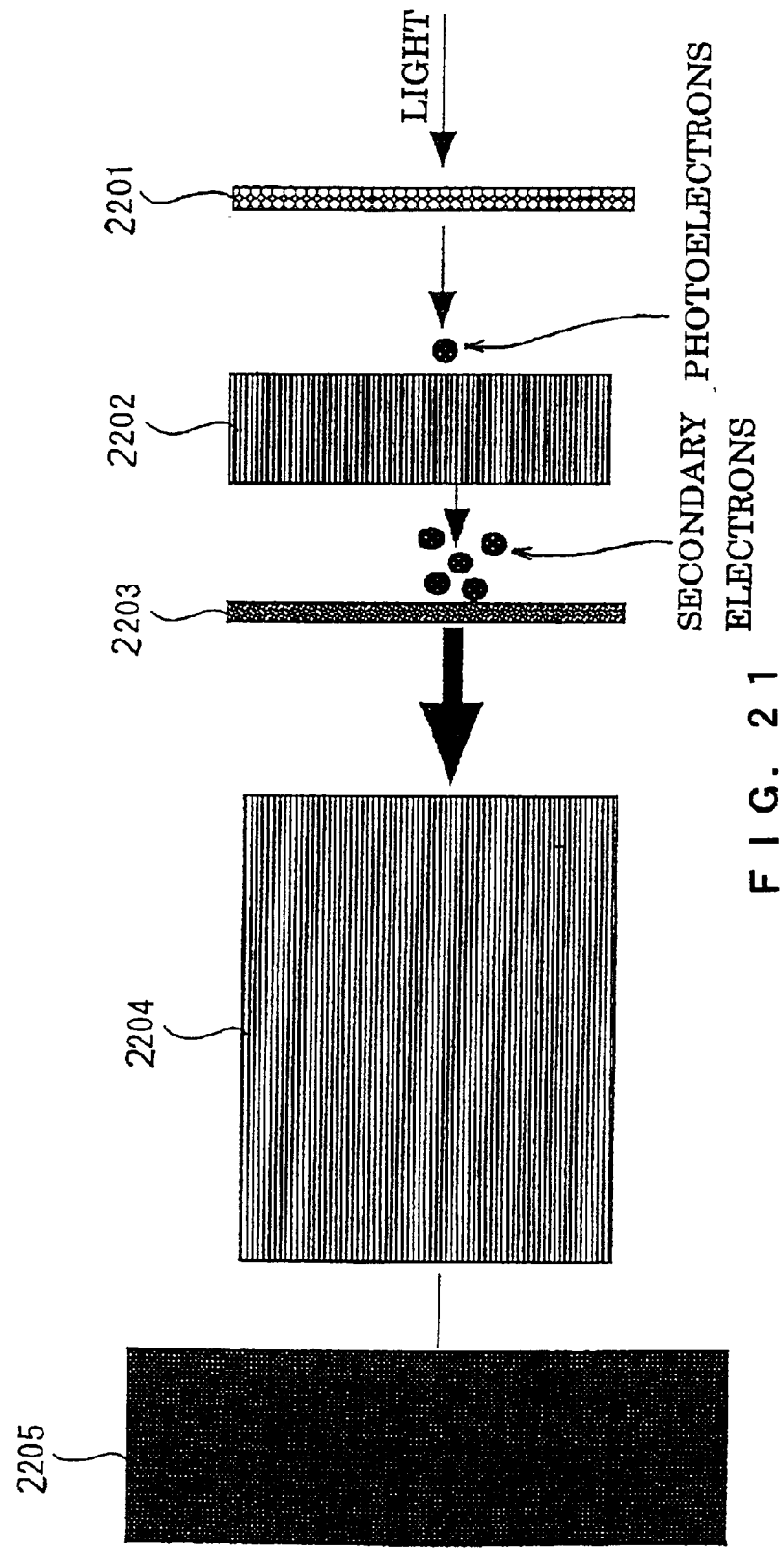
FIG. 21 is a schematic view of an ICCD camera.

Accordingly, the double-resonance-absorption microscope in accordance with this invention preferably uses a fluorescence-detecting means that permits high-sensitivity detection and high S/N and which is adapted for the double-resonance-absorption microscope. FIG. 21 shows one example of this fluorescence-detecting means. This illustrated fluorescence means has a photoelectric converter surface 2201, a microchannel plate 2202, a phosphor screen 2203, an optical fiber coupler 2204, and a CCD detector 2205, and forms an ICCD (I charge-coupled device) camera.

When light (photon) hits the photoelectric converter surface 2201, this surface emits photoelectrons from its back surface according to the number of incident photons at a high efficiency (light to electron conversion). The released photoelectrons are attracted to the microchannel plate 2202 by an electric field. The microchannel plate 2202 is fabricated by binding together fibers of tens of micrometers, and assumes the form of a flat plate. A high voltage is applied across both end surfaces of each fiber. When photoelectrons hit the surfaces of the fibers, secondary electrons are released. Whenever each secondary electron collides within the plane of the fiber, further secondary electrons are produced. Therefore, a quite large number of secondary electrons are emitted from the exit of the microchannel plate. These secondary electrons bombard the phosphor screen 2203, emitting fluorescent light (electron to light conversion). At this time, each incident photon is augmented to a huge amount of photons. Augmented photons from the phosphor screen 2203 are guided to the CCD detector 2205 by the optical fiber coupler 2204, and are detected as a two-dimensional image.

Such an ICCD camera can detect even a single incident photon and hence can achieve quite high sensitivity fluorescence detection. Consequently, the ICCD camera is useful in the double-resonance-absorption microscope under severe fluorescence generation conditions as described above. The fundamental structure of the ICCD camera acting as this fluorescence-detecting means is shown in FIG. 21. Obviously, it may also include a lens system such as a relay lens or a focusing system.

On the other hand, to attain high S/N, a spectral element such as a spectral filter or a wavelength-dispersing element such as a diffraction grating is placed in the optical path of the fluorescence ahead of the ICCD camera. The spectral filter can be a notch filter, bandpass filter, sharp cut filter, or the like for cutting the pump light, the erase light, and fluorescence from other than the sample molecules. The fluorescence-detecting means consisting of the spectral element or the wavelength-dispersing element and the ICCD camera is used to wavelength-separate the fluorescence signal from at least one of the pump light and erase light. Only required fluorescence intensity can be precisely measured. Where a diffraction grating is used, an emission spectrum can be directly obtained after every shot of the laser. Therefore, unwanted wavelengths of light can be removed by processing the data with software in a computer or the like.

Of course, the use of the fluorescence-detecting means consisting of a combination of the above-described ICCD camera and the spectral element or wavelength-dispersing element is not essential. Unwanted wavelengths of light can be removed, for example, by placing only a spectral element or a wavelength-dispersing element ahead of a normal fluorescence detector.

A slit or pinhole maybe placed in the optical path extending from the sample surface to the fluorescence-detecting means. In this case, it is especially desirable to place it immediately before the photoelectric converter surface 2201.

In addition, an embodiment is also possible in which there is provided a means for controlling the times for which voltages are applied to the photoelectric converter surface 2201, the microchannel plate 2202, the phosphor screen 2203, and the electrode of the CCD detector 2205. In this case, the times for which the voltages are applied can be controlled by on/off switches, for example. Preferably, the switching response time is shorter than the fluorescence time of the sample molecules or fluorescence labeler molecules. Furthermore, the times for which the voltages are applied are preferably longer than the fluorescence time of the sample molecules or fluorescence labeler molecules.

[I.b-3.a] Irradiation of Pump Light and Erase Light: Adjustment of Pulse Width and Irradiation Timing In the double-resonance-absorption microscope in accordance with the present invention, if dye lasers are used as the pump light source and as the. erase light source, respectively, the pulse width of the wavelength-converted erase light is generally somewhat narrower than the pulse width of the pump light. If any adjustment of the optical path or the like is not made, pulses of the pump light and the pulses of the erase light will arrive on the sample surface at different instants of time. Accordingly, with respect to a region not necessary for observation, the fluorescence may not be suppressed sufficiently because the irradiation time of the erase light is short, and because overlap of the irradiation times of the pump light and erase light is not complete.

Figure 22:
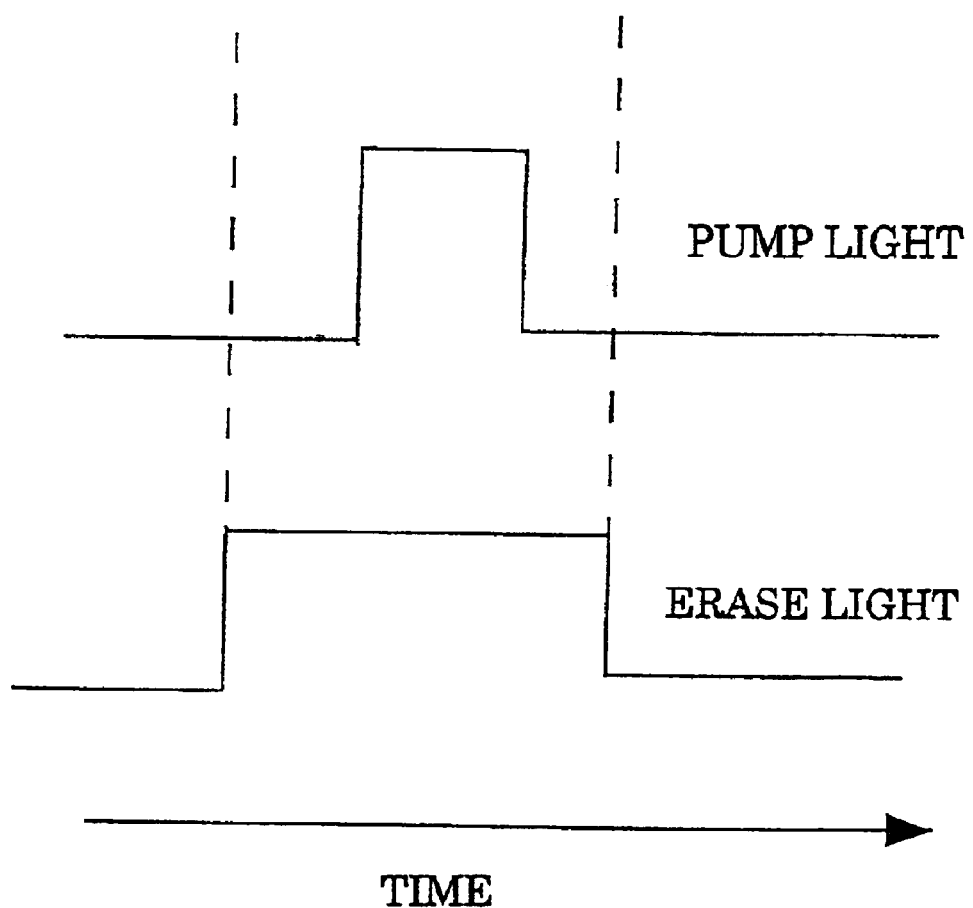
FIG. 22 is a view showing the manner in which pump light and erase light are irradiated.

Therefore, in a preferred embodiment of the invention, to suppress fluorescence more effectively in a double-resonance-absorption microscope in accordance with the present invention, the pulse widths of the pump light and the erase light are set as illustrated in FIG. 22.

In particular, the pulse width of the erase light is set greater than that of the pump light. In addition, the irradiation time of the pump light is made to exactly overlap that of the erase light. In this way, the region irradiated with the erase light is made to overlap a part of the region irradiated with the pump light. In the overlapping region, sample molecules in state $S_1$ can be reliably excited to state $S_2$. Hence, the fluorescence can be more effectively suppressed.

A specific example of a method of setting these factors is described. FIG. 23 shows one example of a pulse width-adjusting means for adjusting the pulse width of erase light such that the pulse width of the erase light becomes greater than the pulse width of the pump light. The pulse width-adjusting means shown in FIG. 23 forms a pulse stretcher optical system having a half mirror 2301 for splitting light and plural prisms 2302. These prisms 2302 form a reflective optical system that constitutes a loop optical path including the half mirror 2301. In this geometry, incident light is first split into first transmitted light and first reflected light by the half mirror 2301. The optical path of the first reflected light is varied by each prism 2302 and returned to the half mirror 2301, and then split into second transmitted light and second reflected light. The second reflected light passes in the same optical path as taken by the first transmitted light. The second transmitted light passes through each prism 2302 and travels through the same loop optical path and is split into third transmitted light and third reflected light by the half mirror 2301. In this way, the division of light by the half mirror 2301 and formation of a loop due to the prism 2302 are repeated. Therefore, pulses delayed by amounts corresponding to the loop optical path are produced in succession bypassing the erase light into the pulse stretcher optical system. As a result, the time duration of the pulse exiting from the loop optical path widens equivalently. In consequence, erase light having a pulse duration longer than that of the pump light can be easily created.

The complete overlap between the irradiation time of the erase light having the increased pulse width and the irradiation time of the pump light is made possible by adjusting the times at which both light beams arrive at the sample. This adjustment can be realized by adjusting the optical path difference between the pump light and the erase light. That is, light travels about 30 cm in air in 1 nsec. If a difference is given to the optical paths of the pump light and the erase light at this ratio, then the times at which these two pulse beams arrive at the sample surface can be adjusted at will. For example, a delay optical system consisting of a translational motion stage and a prism, a mirror, or the like carried on the stage can be used as the irradiation timing-adjusting means relying on the optical path adjustment. In this geometry, the times at which both beams of light reach the sample can be adjusted by adjusting the optical path distance of the incident light passing through the prism or mirror.

Where the pump light and the erase light are generated from two independent pulsed lasers (e.g., two Nd:YAG pulsed lasers), the Q-switching signals for both pulsed lasers are electrically adjusted. That is, the times at which both light beams arrive at the sample can also be adjusted by shifting the instants at which the Q-switching signals are produced, respectively, with respect to each other. For example, the Q-switching can be controlled by producing two trigger pulses with a time difference using a pulse generator and supplying the pulses to the pulsed lasers, respectively.

[I.b-3.b] Irradiation of Pump Light and Erase Light: Adjustment of Optical Axis

In the double-resonance-absorption microscope in accordance with the present invention, it is desired to align the optical axis of the pump light with the optical axis of the erase light to produce sufficient super-resolution. This optical axis alignment is made possible by preparing a reference sample and observing a fluorescence image of the reference sample before actual observation of the sample.

Specifically, the reference sample, is prepared as follows. Molecules capable of fluorescing either by irradiation with pump light or irradiation with erase light are uniformly applied to a substrate that is transparent to both pump light and erase light. This reference sample is irradiated with the pump light and erase light simultaneously. The area and the brightness of the resulting fluorescence image are measured. If the pump light and erase light overlap exactly (i.e., if the optical axes of both light beams are aligned), the area is minimal and the brightness is maximal. Accordingly, a complete optical axis alignment can be accomplished by adjusting the optical axes to minimize the area of the fluorescence image and to maximize the brightness.

Where the means for taking the fluorescence image is the aforementioned ICCD camera, if the fluorescence image is excited with weak laser light and feeble, it can be observed. Therefore, if stray light from the pump light or from the erase light is mixed in the fluorescence image as background light, the measurements of the area and brightness are not affected seriously, because the light is feeble. Hence, accurate optical axis adjustment is permitted. If the effects of stray light are reduced further, a light-splitting element or wavelength-dispersing element may be placed in the optical path as mentioned previously.

[I.b-4] Laser Scanning

The double-resonance-absorption microscope in accordance with the present invention has very high spatial resolution. One side of an observed region corresponding to one pixel can be set to less than 100 nm. In other words, to produce such ultrahigh spatial resolution certainly, it is necessary to scan the sample with the pump light and erase light accurately where this double-resonance-absorption microscope is used as a laser scanning microscope. In the laser scanning microscope, the focal point and the sample are moved relative to each other within a plane. The fluorescence signal is measured at each point. The fluorescence signal is processed by information processing technology to produce a two-dimensional image.

Accordingly, in the double-resonance-absorption microscope in accordance with the present invention, to cope with the spatial resolution on the nanometer order, it is desired that the instrument be equipped with a mechanism for scanning the pump light and the erase light or moving the sample at nanometer-order accuracy. As a scanning mechanism for the pump light and erase light, a rocking mirror mechanism capable of fine scanning by rocking a mirror in the optical paths of the pump light and erase light can be used. As a mechanism for moving the sample, a sample stage mechanism capable of being moved in two dimensions by an electromagnetic motor or a piezoelectric device (also known as a piezoelectric vibrator) can be used. Of course, by aligning the optical axes of the pump light and erase light coaxially as described above, nanometer-order accurate movements and scanning are made more reliable.

EXAMPLE 2

Figure 24:
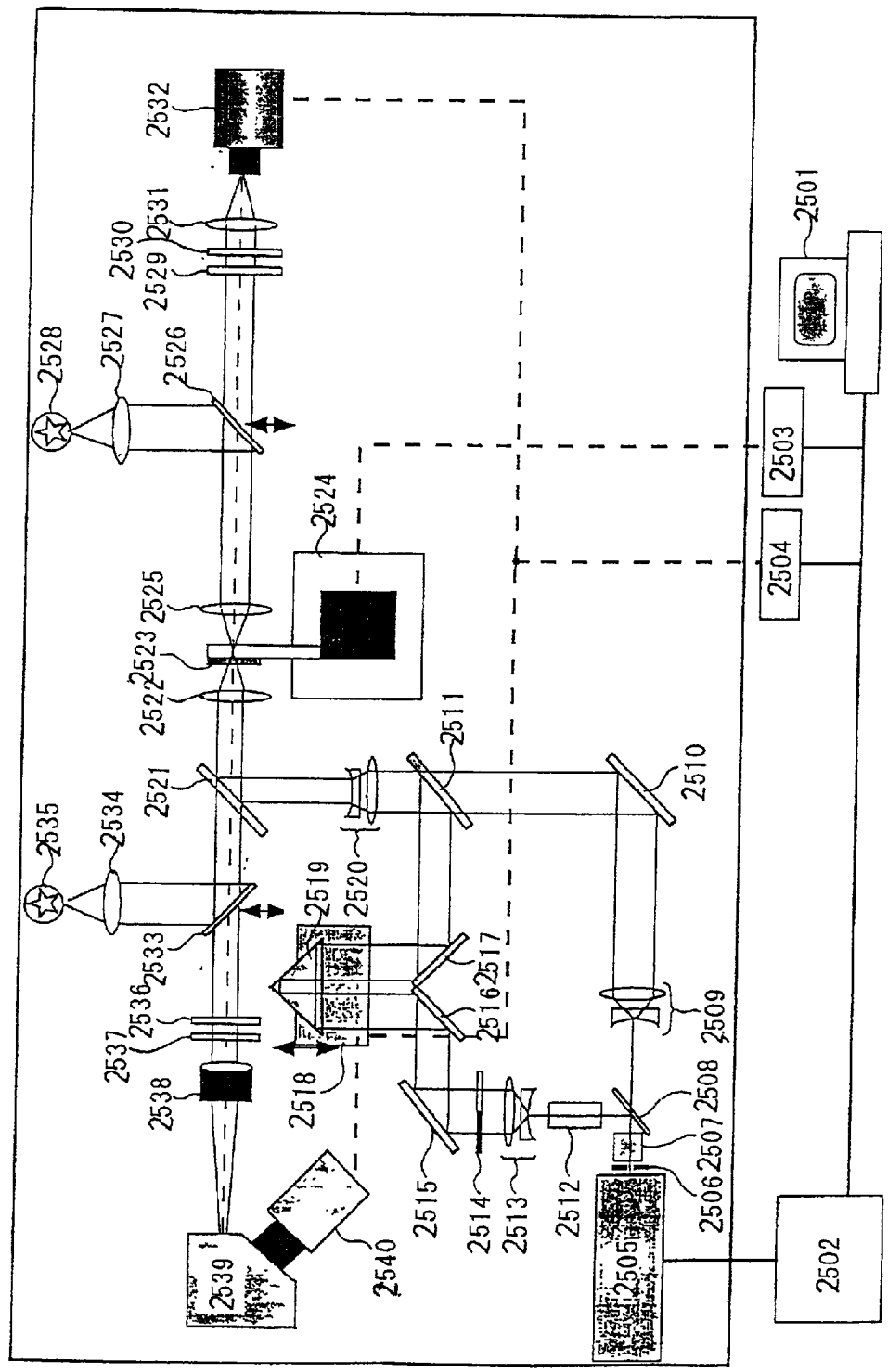
FIG. 24 is a schematic diagram of a laser scanning fluorescence microscope system using a double-resonance-absorption microscope in accordance with the invention.

FIG. 24 is a schematic diagram showing one example of the double-resonance-absorption microscope in accordance with the present invention. The illustrated microscope forms a laser scanning fluorescence microscope. Pump light and erase light are focused into spots. Fluorescence is detected while scanning a sample 2523 relative to the spots. The detected fluorescence signal is imaged using a computer 2501.

The whole system is controlled by the computer 2501, which controls the timing of lasing of an Nd:YAG laser 2505 that is a fundamental light source via a laser controller 2502. At the same time, the computer controls movement of a sample stage 2524 via a sample stage controller 2503 in synchronism with the timing of lasing of the laser to scan the sample 2523 in two dimensions. Concurrently, the fluorescence signal from the sample 2523 is taken from an ICCD camera 2540 via a camera controller 2504 in synchronism with the lasing of the laser.

In the present embodiment, it is assumed that the sample 2523 has been stained with fluorescence labeler molecules and that the fluorescence labeler molecules are rhodamine-based molecules. FIG. 10 shows spectral data about rhodamine 6G that is one kind of rhodamine-based molecules. As can be seen from this diagram, an absorption band corresponding to excitation $S_0 \rightarrow S_1$ exists near 530 nm and that excitation $S_1 \rightarrow S_2$ and a fluorescence band are present around 600 nm. Accordingly, fluorescence wavelengths other than 599 nm are made to disappear by a double-resonance-absorption process and a stimulated emission, which in turn are caused by excitation $S_0 \rightarrow S_1$ with pump light having a wavelength $\lambda_1$ of 532 nm and excitation $S_1 \rightarrow S_2$ with erase light having a wavelength $\lambda_2$ of 599 nm.

The light having the wavelength of 532 nm can be created by modulating the fundamental wave having a wavelength of 1064 nm from the Nd:YAG laser 2505 into its second-harmonic wave by a wavelength modulator 2507 consisting of a BBO crystal, KTP crystal, or the like. The light having the wavelength of 599 nm can be created by converting wavelength of 532 nm to wavelength 599 nm by a Raman shifter 2512 made of $Ba(NO_3)_2$. The light with wavelength 532 nm from the wavelength modulator 2507 is split by a half mirror 2508. The transmitted light is enlarged into collimated light of appropriate size by a telescope 2509 and used as pump light. On the other hand, the reflected light is modulated into light having a wavelength of 599 nm by the Raman shifter 2512 and used as erase light.

Generally, an Nd:YAG laser 2505 has a resonator consisting of a gaussian mirror and, therefore, the wavefront is relatively uniform around the center (i.e., in the vicinity of the optical axis of the beam). However, the wavefront is disturbed at peripheral portions. The peripheral portions produce phase differences with the central portion. Therefore, in order to obtain laser light having a good beam profile, the laser light from the Nd:YAG laser 2505 is passed through a pinhole plate 2506 to extract only a central portion around the optical axis. The extracted laser light is passed through the wavelength modulator 2507 or the Raman shifter 2512 as described above. In this way, good pump light and erase light whose wavefronts are uniform and optimal for a double-resonance-absorption microscope can be created.

Figure 25:
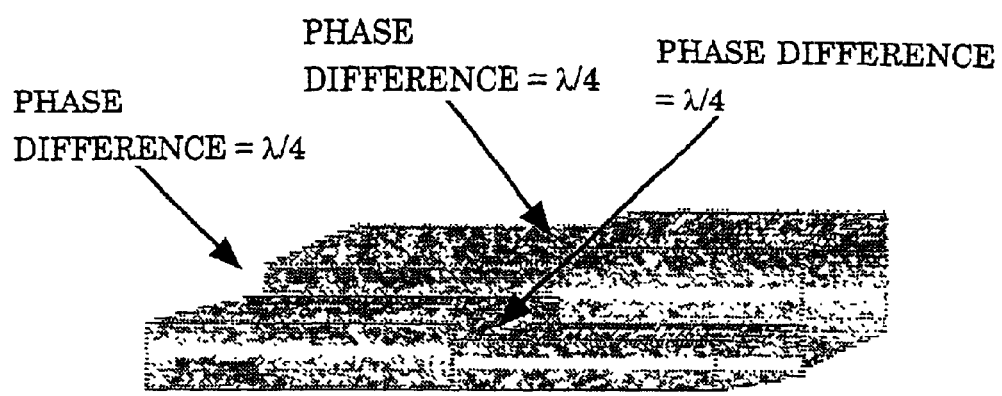
FIG. 25 is a schematic diagram showing another example of a phase plate fabricated by etching a glass substrate.

The erase light having such a good beam profile is enlarged into collimated light of appropriate size by the telescope 2513. Then, the light enters the phase plate 2514. In the present embodiment, the wavelength $\lambda_2$ of the erase light is 599 nm and so the phase plate 2514 is prepared by etching a glass substrate as shown in FIG. 25. Since the index of refraction of glass is 1.46 (at wavelength 599 nm), a quarter wavelength of the erase light corresponds to a thickness of 325.5 nm of the glass substrate. Accordingly, as shown in FIG. 25, the face of the phase plate 2514 is divided into four regions. The thickness is so set that the mutually adjacent regions produce a phase difference of a quarter wavelength, and then the glass is etched. Consequently, the erase light can be shaped into an ideal hollow beam. That is, the erase light is passed through the phase plate 2514 in such a way that the optical axis of the light is coincident with the center of the phase plate 2514. As a result, those portions of the erase light which pass through two opposite central portions of the phase plate 2514 are opposite in phase to each other. Therefore, the electric field intensities in the regions close to the optical axis are zero. As a consequence, erase light having a hollow beam profile that is ideal for developing super-resolution by fluorescence suppression can be obtained. The erase light shaped into a hollow beam in this way is a first-order Bessel beam.

Instead of fabricating the phase plate 2514 by etching, it may also be fabricated by depositing a thin film of magnesium fluoride or the like that gives a phase difference onto a substrate. Obviously, the order in which the pinhole plate 2506, the Raman shifter 2512, the telescope 2513, and the phase plate 2514 are arranged may be changed as long as an ideal erase light beam is obtained.

The pump light and the hollow erase light beam are reflected by reflective mirrors 2510 and 2515, respectively, and made to enter a beam combiner 2511, where both beams are made coaxial. Of course, both light beams are made equal in size by telescopes 2509 and 2513. The sizes of the pump light and erase light that are made coaxial are adjusted to be equal to the diameter of a condenser objective lens 2522 by a beam reducer 2520 that is a kind of telescope optical system such that both light beams are accepted by the full aperture of the objective lens 2522. The beams are focused onto a surface of a sample 2523 by the condenser objective lens 2522.

In the present embodiment, as already described in connection with FIG. 22, the pulse width of the erase light is set greater than that of the pump light. To realize irradiation settings for attaining complete overlap between the pump light irradiation time for the sample 2523 and the erase light irradiation time, a pulse stretcher optical system (not shown but having the structure shown in FIG. 23) acting as a pulse width-adjusting means for the erase light is interposed between reflecting mirrors 2515 and 2516. A delay optical system consisting of a translational motion stage 2518 and a prism 2519 carried on it are mounted as an irradiation timing-adjusting means on the side of the reflected light path formed by the reflecting mirror 2516.

In this geometry, the erase light whose pulse width is increased beyond that of the pump light by the pulse stretcher optical system as shown in FIG. 23 is then made to enter the prism 2519 of the delay optical system. At this time, the translational motion stage 2518 is made to move a distance equal to the delay distance of the erase light relative to the pump light to adjust the distance that the erase light travels in its optical path turned by the prism 2519. The delay distance is 30 cm where the arrival time distance is 1 nsec. This distance can be measured using a micrometer, for example. The results of the measurement may be reflected in the distance to be traveled by the translational motion stage 2518. In this way, irradiation optimal for suppression of fluorescence is permitted. That is, the pulse width of the erase light is set greater than that of the pump light. The irradiation time of the pump light exactly overlaps the irradiation time of the erase light.

Where the pump light and the erase light are made to hit the sample 2523 in this way, an illuminated region in which both light beams overlap forms a fluorescence-suppressed region $A_1$, because the hollow erase light overlaps a part of the region irradiated with the pump light. The region that is irradiated with the central hollow portion of the hollow erase light and thus illuminated only with the pump light forms a fluorescence region $A_0$ (see FIG. 6). Rhodamine-based molecules fluoresce only from this fluorescence region $A_0$ that is an observed region.

Figure 26:
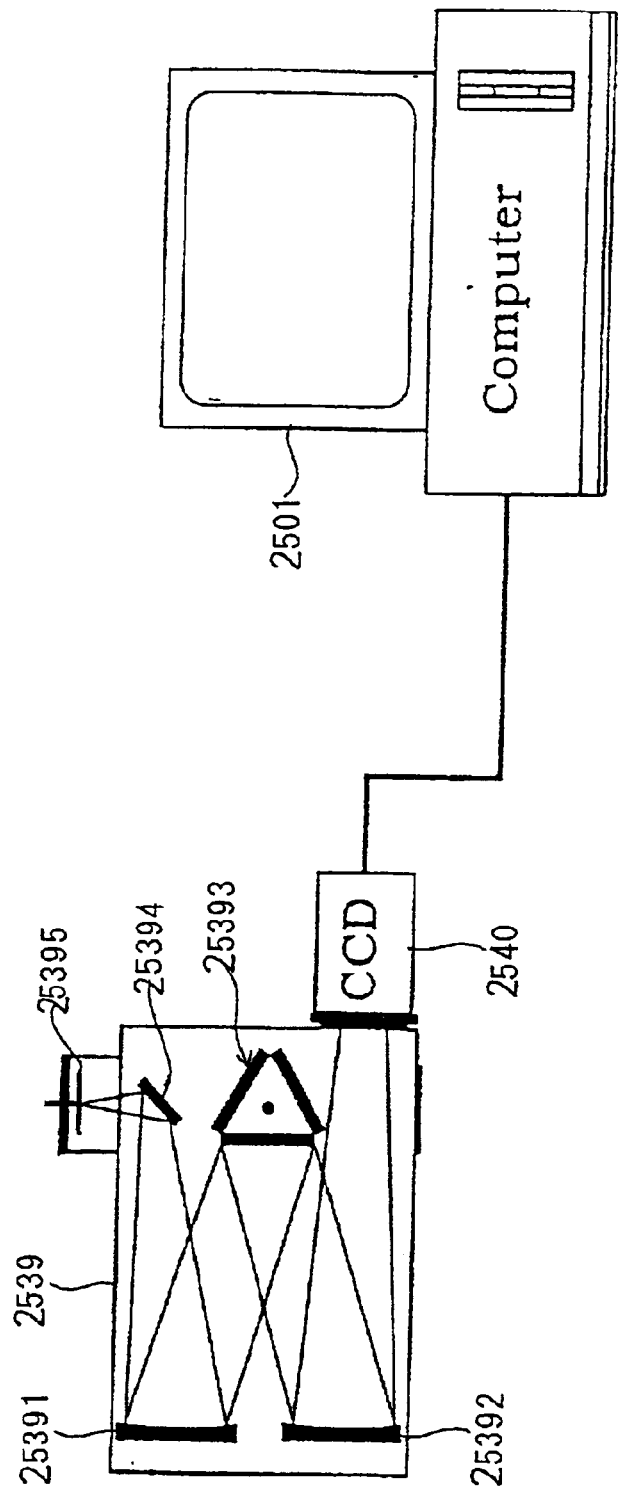
FIG. 26 is a schematic diagram showing the internal structure of a spectroscope used in the microscope system shown in FIG. 24.

The emitted fluorescent light again passes through the condenser objective lens 2522 and enters a spectroscope 2539 from an eyepiece lens 2538. As shown in FIG. 26, the spectroscope 2539 includes a collimator spherical mirror 25391, a focusing spherical mirror 25392, and a mechanically switchable diffraction grating 25393 as its fundamental optical components. Fluorescent light passed through an incident slit 25395 is directed to the collimator spherical mirror 25391 by a reflecting mirror 25394. The light is focused onto the diffraction grating 25393 by the collimator spherical mirror 25391. The fluorescent light that is wavelength-resolved on the diffraction grating 25393 is focused onto the CCD elements of an ICCD camera 2540 by the focusing spherical mirror 25392.

A signal obtained by the ICCD camera 2540 at this time is a fluorescence spectrum per shot of laser. The sample stage 2524 is moved in two dimensions in synchronism with a shot of the laser. The resulting fluorescence spectra are accumulated and imaged by the computer 2501, whereby a two-dimensional fluorescence image of the sample 2523 can be created. If the pump light and the erase light are mixed into the fluorescence signal, the signal of the wavelength components of the pump light and the erase light is removed during the image creation process by the computer 2501. The image is created using only the genuine fluorescence wavelength component. Thus, a fluorescence image with sufficient super-resolution and high S/N can be derived.

To improve the super-resolution further, a notch filter 2536 for cutting the pump light wavelength and another notch filter 2537 for cutting the erase light wavelength maybe inserted before the spectroscope 2539. In FIG. 24, they are inserted before the eyepiece lens 2538 at the entrance of the spectroscope 2539. In this manner, the pump light and the erase light can be separated from the fluorescence signal before entering the spectroscope 2539. Only the genuine fluorescence component can be subjected to spectral analysis. Hence, the purity of the fluorescence signal can be enhanced. Super-resolution can be developed more effectively. Of course, if necessary, a bandpass filter and a sharp cut filter may be inserted in addition to the notch filters 2536 and 2537 to cut unwanted wavelength components other than the fluorescence from the fluorescence labeler molecules.

If the incident slit 25395 of the spectroscope 2539 is opened to focus the zeroth-order light from the diffraction grating 25393 onto the CCD elements of the ICCD camera 2540, then a fluorescence image from the surface of the sample 2523 is directly obtained. Especially, in this case, to improve the S/N, the above-described notch filters 2536, 2537, a bandpass filter, or a sharp cut filter is preferably inserted.

A sample-moving mechanism in accordance with the present invention is next described. The sample stage 2524 that is controlled by a computer as mentioned previously can move in five dimensions, i.e., in the directions of X, Y, Z, φ, and θ.

First, an inch worm stage mechanism that is one kind of piezoelectric device is preferably used for movement in the Z-direction that is the direction of the optical axis. The absolute position can be monitored by a rotary encoder.

Generally, where light is condensed by an objective lens having a large numerical aperture, the depth of focus becomes very shallow. In addition, it is very difficult to search for the focal point. For example, where light is focused by a lens having a numerical aperture of NA, the spread d of the focused beam at a point at a distance of δz from the focus is given by $$d = \delta z \cdot NA \tag{13}$$

If δz is 600 nm, d is about 400 nm. This is comparable to a size obtained where the pump light is confined to the diffraction limit. Fundamentally, it means that the position is controlled at an accuracy of less than 1 μm. Therefore, the inch work stage using one kind of piezoelectric device is adapted for the double-resonance absorption microscope in accordance with the invention that produces super-resolution, because position control at submicron accuracy is possible. The observed region can be quickly found by monitoring the absolute position, even if the sample 2523 is exchanged.

Figure 27:
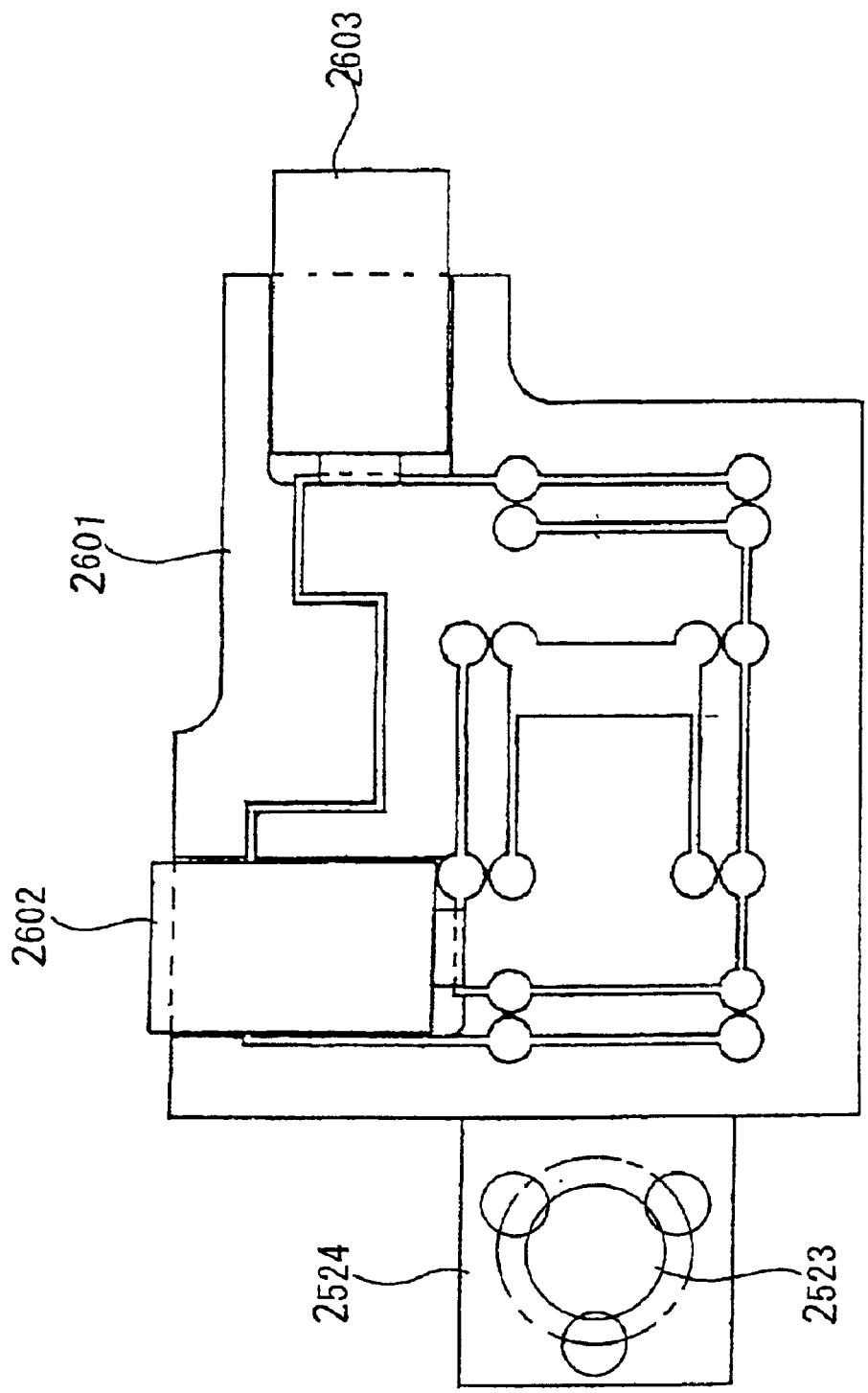
FIG. 27 is a schematic diagram showing an XY-translational mechanism for translating the sample stage in the microscope system shown in FIG. 24 in two dimensions.

FIG. 27 shows one example of a two-dimensional motion mechanism for moving the sample stage 2524 in the X- and Y-axis directions. This illustrated two-dimensional motion mechanism comprises a leaf spring 2601 and two laminar piezoelectric elements 2602, 2603. The piezoelectric elements 2602 and 2603 drive the leaf spring 2601. One laminar piezoelectric element 2602 moves the sample stage 2524 in the X-axis direction, while the other laminar piezoelectric element 2603 moves the stage 2524 in the Y-axis direction. In this way, the sample stage 2524 is moved in two dimensions within the plane perpendicular to the optical axis.

Figure 28:
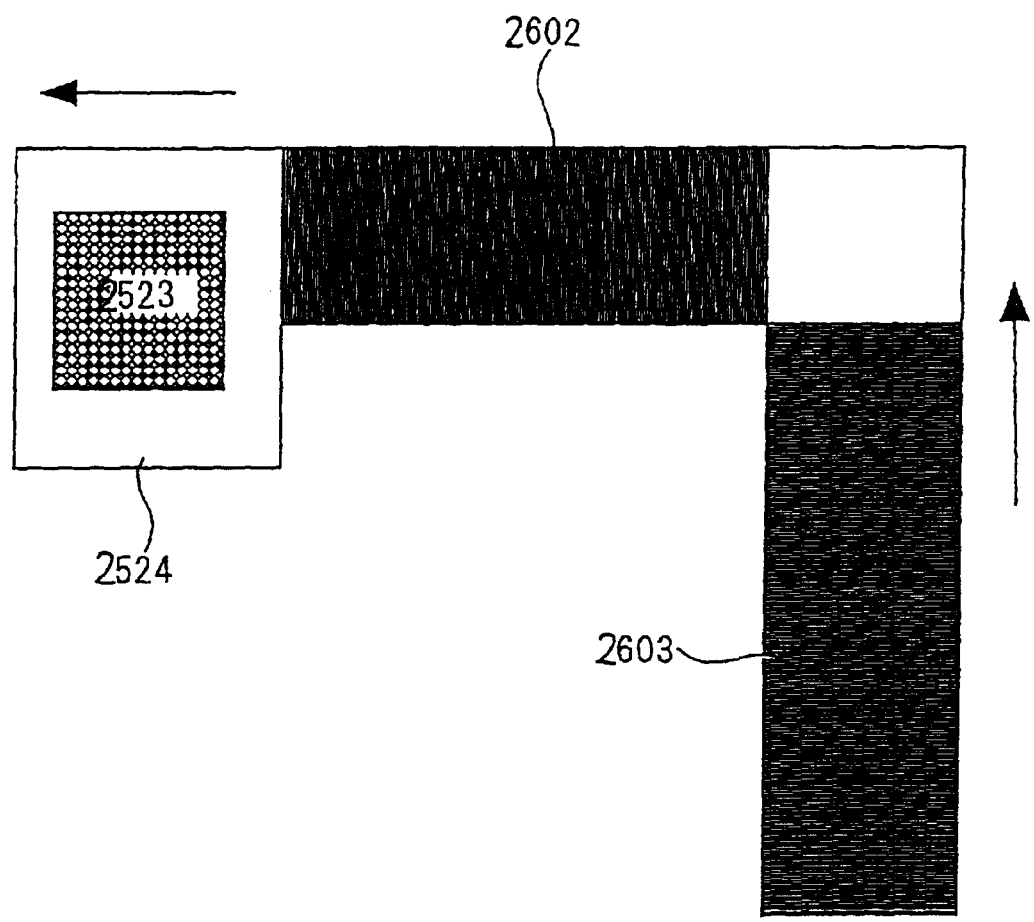
FIG. 28 is a schematic diagram showing a further XY-translational mechanism for translating the sample stage in two dimensions.

As shown in FIG. 28, a moving mechanism comprising the sample stage 2524, on which laminar piezoelectric elements 2602 and 2603 are directly mounted, may also be used. Note that the mechanism using the leaf spring 2601 as shown in FIG. 27 can more effectively prevent deterioration of the image quality due to distortion of the scanned surface.

The sample stage 2524 is equipped with driver mechanisms for movement in the θ and φ directions. These are added such that the optical axes of the pump light and of the erase light cross the surface of the sample 2523 accurately perpendicularly.

The sample stage 2524 relying on the five-dimensional movement mechanism constructed as described thus far is based on mechanical scan relative to the sample 2523. The laser beam itself may also be scanned by mounting a swinging galvano mirror, for example, in the path.

One example of adjustment of the optical axes of the pump light and erase light is described. A reference sample used to adjust the optical axis is prepared by dispersing rhodamine B in a thin film that is transparent to both pump light and erase light. Both pump light and erase light produce excitation $S_0 \rightarrow S_1$ a high probability in rhodamine B and, therefore, a sufficient amount of fluorescent light can be observed. The thin film of this reference sample can be prepared, for example, by dispersing rhodamine B in PMMA in a solution state and spin-coating it on a glass slide to a thickness of several micrometers.

Procedures for the optical axis adjustment are effected as follows. The pump light and the erase light are simultaneously directed to the aforementioned reference sample. The position of the focal point is moved by adjusting the tilt of the reflecting mirror 2510 in the optical path of the pump light or the tilt of the reflecting mirror 2515 in the optical path of the erase light to bring the focal point of the pump light into agreement with the focal point of the erase light while observing the emitted fluorescent light by the computer 2501 via the ICCD camera 2540. When the focal points of the pump light and the erase light are coincident with each other, the emission area is minimal and the emission intensity is maximal. Therefore, the optical axes of the pump light and the erase light are aligned by adjusting the optical system so as to produce such a fluorescence image.

In FIG. 24, a half mirror 2533, a lens 2534 for illuminating light, and an illuminating light source 2535 are optical components used to adjust the optical axes.

Referring still to FIG. 24, another microscope optical system for optical axis adjustment may be mounted behind the sample 2523. Also shown in FIG. 24 are a lens 2525 for transmitted light, a half mirror 2526, a lens 2527 for illuminating light, an illuminating light source 2528, a notch filter 2529 for cutting the pump light, another notch filter 2530 for cutting the erase light, an eyepiece lens 2531, and an ICCD camera 2532. These components form the microscope optical system for adjusting the optical axes.

The whole system described above is controlled in the manner described below. The microscope system in accordance with the present embodiment is equipped with an electrical control unit having a camera controller 2504 for controlling the ICCD camera 2540, a sample stage controller 2503 for controlling the sample stage 2524, and a laser controller 2502 for controlling the Nd:YAG laser 2505. Where the above-described microscope optical system for the optical axes is also mounted, the camera controller 2504 also controls the ICCD camera 2532. All of these controllers are under the control of the computer 2501.

With respect to the ICCD camera 2540, a gate pulse that determines the time for which a fluorescence signal is detected is produced, and the obtained fluorescence signal is sent to the computer 2501. With respect to the sample stage 2524, the piezoelectric elements 2602 and 2603 (see FIGS. 27 and 28) are moved in steps. With respect to the Nd:YAG laser 2505, the Q-switching signal is controlled. A cycle of sequence of processing for the system consists of operations:
1. Lasing of Nd:YAG laser
2. Gate pulse generation from the ICCD camera
3. Acceptance of data
4. Stepwise movement of the piezoelectric elements This cycle is repeated a number of times corresponding to the number of pixels of the gained image. Fluorescence spectra made up of individual pixels from the ICCD camera 2540 are accepted as numerical data into the computer 2501. After gaining the data about all the pixels, the wavelength components of the pump light and erase light mixed in as background signals are removed by numeral processing. A value obtained by integrating other wavelength components is taken as an image signal about one pixel. The image data obtained in this way is sent to an external output device such as a CRT or a printer and stored in a storage device such as in an HDD or FDD.

As described in detail thus far, the present invention can offer a novel double-resonance-absorption microscope which is capable of generating a hollow erase light beam ideal for providing super-resolution and which can accomplish super-resolution more effectively and reliably.

[II] Novel Dye Laser and Novel Double-Resonance-Absorption Microscope Using a light source having excellent operability and maintainability The present invention is also directed to a dye laser that can be useful as a light source in a microscope. Use of this novel dye laser accomplishes a novel double-resonance-absorption microscope having excellent functionality, operability, and maintainability associated with the light source.

The dye laser in accordance with the present invention is characterized in that it has a solid laser medium and a short pulsed laser for exciting the solid laser medium in which molecules having at least two quantum levels are dispersed as dyes. This is hereinafter referred to as the solid-state dye laser.

In this solid-state dye laser, the laser medium is a solid medium containing dye molecules and, therefore, is entirely different from liquid media of conventional dye lasers. Therefore, a cartridge-type solid-state dye laser medium capable of being replaced with one touch can be achieved. In this way, the medium can be replaced quite easily without changing other optics. The burden on the user, such as maintenance, can be alleviated.

A sol-gel method, for example, can be used to create the solid laser medium. The aforementioned dye molecules are dispersed in an inorganic or organic solution, and the solution is solidified by a sol-gel method. Since the created solid has a quite high damage threshold, inorganic glass, PMMA, and so on can be preferably used. The sol-gel method permits creation of various shapes of solid. Therefore, solid laser media in shapes appropriate for lasers can be readily accomplished. No restrictions are placed on the starting solution of the sol-gel method or on various conditions as long as a solid suitable for a laser medium such as inorganic glass or PMMA can be created.

Where a dye is dispersed using a medium consisting of a solid organic material typified by PMMA, the solid laser medium can be created by melting at high temperatures, as well as by a sol-gel method. In this case, a solid organic material such as PMMA is heated and melted, a dye is added to the molten material, and then the material is cooled. In this way, solid laser media can be fabricated easily and with excellent mass productivity.

Dye molecules containing double bonds or benzene rings can be used. Examples include:

2,2"-Dimethyl-p-terphenyl:
P-terphenyl(PTP):
3,3',2",3"-Tetramethyl-P-quaterphenyl:
2,2""-Dimethyl-P-quaterphenyl:
2-Methyl-5-t-butyl-p-quaterphenyl:
2-(4-Biphenylyl)-5-(4-t-butylphenyl)-1,3,4-oxiazol (BPBD-365):
2-(4-Biphenylyl)-phenyl-1,3,4-oxadiazol:
2,5,2""5,"""-Tetramethyl-p-quinquephenyl:
3,5,3"""5,"Ofl'-Tetra-t-butyl-p-quinquephenyl:
2,5-Diphenyloxazol:
2,5-Diphenylfuran:
PQP(p-Quanterphenyl:
2,5-Bis-(4-biphenylyl)-1,3,4-oxadiazol:
p-Quaterphenyl-4-4""-disulfonicacid Disodiumsalt:
p-Quaterphenyl-4-4""-disulfonicacid Dipotassiumsalt:
4,4""-Bis-(2-butyloctyloxy)-p-quanterphenyl:
3,5,3"""5,"""-Tetra-t-butyl-p-sexiphenyl:

2-(1-Naphthyl)-5-phenyloxazol:
2-(4-Biphenylyl)-6-phenylbenzoxazotetrasulfonicacid Potassium Salt:
2-(4-Biphenylyl)-6-phenylbenzoxazol-1,3:
4,4'-Diphenylstilbene:
[1,1'-Biphenyl]-4-sulfonic acid, 4,4''-1,2-ethene-diylbis-,dipotassium salt:
2,5-Bis-(4-biphenylyl)-oxazol:
2,2'-([1,1'-Biphenyl]-4,4'-diyldi-2,1-ethenediyl)-bis-benzenesulfonic acid Disodium Salt:
7-Amino-4-methylcarbostyryl:
1,4-Di[2-(5-phenyloxazoly)]benzene:
7-Hydroxy-4-methylcoumarin:
p-Bis(o-methylstyryl)-benzene:
Benzofuran,2,2'-[1,1'-biphenyl]-4,4'-diyl-bis-tetrasulfonic-acid:
7-Dimethylamino-4-methylquinolom-2:
7-Amino-4-methylcoumarin:
2-(p-Dimethylaminostyryl)-pyridylmethyl Iodide:
7-Diethylaminocoumarun:
7-Diethylamino-4-methylcoumarin:
2,3,5,6-1H,4H-Tetrahydro-8-methylginolizino-[9,9a,1-gh]-coumarin:
7-Diethylamino-4-trifluormethylcoumarin:
7-Dimethylamino-4-trifluormethylcoumarin:
7-Amino-4-trifluormethylcoumarin:
2,3,5,6-1H,4H-Tetrahydroquinolizino-[9,9a,1-gh]-coumarin:
7-Ethylamino-6-methyl-4-trifluormethylcoumarin:
7-Ethylamino-4-trifluormethylcoumarin:
2,3,5,6-1H,4H-Tetrahydro-9-carboethoxyquinolizino-[9,9a,1 gh]coumarin
2,3,5,6-1H,4H-Tetrahydro-9-(3-pyridyl)-quinolizino-[9,9a,1 gh]coumarin
3-(2'-N-Methylbenzimidazolyl)-7-n,n-diethylaminocoumarin:
2,3,5,6-1H,4H-Tetrahydro-9-acetylquinolizino-[9,9a,1-gh]-coumarin:
N-Methyl-4-trifluormethylpiperidino-[3,2-g]-coumarin:
2-(p-Dimethylaminostyryl)-benzothiazolylethyl Iodide:
3-(2'-Benzimidazolyl)-7-N,N-diethylaminocoumarin:
Brillantsulfaflavin:
3-(2'-Benzothiazolyl)-7-diethylaminocoumarin:
2,3,5,6-1H,4H-Tetrahydro-8-trifluormethylquinolizino-[9,9a,1-gh]coumarin:
3,3'-Diethyloxacarbocyanine Iodide:
3,3'-Dimethyl-9-ethylthiacarbocyanine Iodide:
Disodium Fluorescein (Uranin):
9-(o-Carboxyphenyl)-2,7-dichloro-6-hydroxy-3H-xanthen-3-on2,7-Dichlorofluorescien-Fluorescein 548:
Fluorol 555 (Fluorol 7GA):
o-(6-Amino-3-Amino-3H-xanthen-9-yl)-benzonicacid (Rhodamine 560)
BenzoicAcid,2-[6-(ethylamino)-3-(ethylamino)-2,7-dimethyl-3H-xanthen9-yl],perchlorate (Rhodamine 575):
Benzonic Acid,2-[6-(ethylamino)-3-(ethylamino)-2,7-dimethyl-3X-xanthen-9-yl]-ethylester,monohydrochloride (Rhodamine 590):
1,3'-Diethyl-4,2'-quinolyloxacarbocyanine Iodide:
1,1'-Diethyl-2,2'-carbocyanine Iodid:
2-[6-(diethylamino)-3-(diethylimino)-3H-xanthen-9-yl] benzonic acid (Rhodamine 610):
Ethanaminium,N-[(6-diethylamino)-9-(2,4-disulfophenyl)-3H-xanthen-3-ylidene]-N-ethylhydroxid,inner salt, sodium salt:
Malachit Green:
3,3'-Diethylthiacarbocyanine Iodide:
1,3'-Diethyl-4,2'-quinolylthiacarbocyanine Iodide:
8-(2-Carboxyphenyl)-2,3,5,6,11,12,14,15-octahydro-1H,4H,10H,13H-diquinolizino[9,9a,1-bc:9',9a',1-hi]xanthylium Perchlorate (Rhodamine 640):
4-Dicyanmethylene-2-methyl-6-(p-dimethylaminostyryl)-4H-pyran:
3,3'-Diethyloxadicarbocyanine Iodide:
8-(2,4-Disulfophenyl)-2,3,5,6,11,12,14,15-octahydro-1H,4H,1OH,13H-diquinolizino[9,9a,1-bc:9',1-hi]xanthene (Sulforhodamine 640):
5,9-Diaminobenzo[a]phenoxazonium Perchorate:
9-Diethylamino-5H-benzo(a)phenoxazin-5-one:
5-Amino-9-diethyimino(a)phenoxazonium Perchlorate:
3-Ethylamino-7-ethylimino-2,8-dimethylphenoxazin-5-ium Perchorate:
8-(Trifluoromethyl)-2,3,5,6,11,12,14,15-octahydro-1H,4H,10H,13H-diquinolizino[9,9a,1-bc:9',9a,1-hi]xanthylium Perchlorate:
1-Ethyl-2-(4-(p-Dimethylaminophenyl)-1,3-butadienyl)-pyridinium Perchlorate:
Carbazine 122:
9-Ethylamino-5-ethylimino-10-methyl-5H-benzo(a)phenoxazoniumPerchlorate:
3-Diethylamino-7-diethyliminophenoxazonium Perchlorate:
3-Diethylthiadicarbocyanine Iodide:
Oxazine 750:
1-Ethyl-4-(4-(p-Dimethylaminophenyl)-1,3-butadienyl)-pyridininum Perchlorate:
1,1',3,3,3',3'-Hexamethylindodicarbocyanine Iodide:
1,1'-Diethyl-4,4'-carbocyanine.Iodide:
2-(4-(p-Dimethylaminophenyl)-1,3-butadienyl)-1,3,3-trimethyl-3H-indolium Perchlorate:
2-(4-(p-Dimethylaminophenyl)-1,3-butadienyl)-3-ethylbenzothoazolium Perchlorate:
1,1'-Diethyl-2,2'-dicarbocyanine Iodide:
1-Ethyl-4-(4-(9-(2,3,6,7-tetrahydro-1H,5H-benzo(i,j)-chinolinozinium))-1,3-butadienyl)-pyridinium Perchlorate:
3,3'-DimethyloxatricarbocyanineIodide:
1-Ethyl-4-(p-Dimethylaminophenyl)-1,3-butadienyl)-quinolinium Perchlorate:
8-Cyano-2,3,5,6,11,12,14,15-octahydro-1H,4H,10H,13H-diquinolizino[9,9a,1-bc:9a',1-hi]xanthylium Perchlorate (Rhodanine800):
2-(6-(4-Dimethylaminophenyl)-2,4-neopentylene-1,3,5)-3-methylbenzothiazoliumPerchlorate:
1,1',3,3,3',3'-Hexamethylindotricarbocyanine Iodide:
IR125:
3,3'-Diethylthiatricarbocyanine Iodide:
IR144:
2-(6-(9-(2,3,6,7,-Tetrahydro-1H,5H-benzo(i,j)-chinolizinium))-2,4-neopentylene-1,3,5-hexatrienyl)-3-methyllbenzothiazolium Perchlorate:
3,3'-Diethyl-9,11-neopentylenethiatricarbocyanine Iodide:
1,1',3,3,3',3'-Hexamethyl-4,4',5,5'-dibenzo-2,2'-indotricarbocyanine Iodide:
3,3'-Diethyl-4,4',5,5'-dibenzothiatricarbocyanine Iodide:
1,2'-Diethyl-4,4'-dicarbocyanine Iodide:
IR140:
2-(8-(4-p-Dimethyhlaminophenyl)-2,4-neopentylene-1,3,5,7-octatetraenyl)-3-methylbenzothiazolium Perchlorate:

IR132:
2-(8-(9-(2,3,6,7-Tetrahydro-1H,5H-benzo(i,j)
chinolizinium))-2,4-neopentylene-1,3,5,7-octatetraenyl)-
3-methylbenzothiazolium Perchlorate:
IR26:
IR 5

On the other hand, this solid-state dye laser uses short pulsed laser pumping and so it is quite advantageous in realizing super-resolution if the dye laser is used as a pump light source and as an erase light source in a double-resonance-absorption microscope. In particular, to accomplish fluorescence suppression in a double-resonance-absorption microscope, the pulse widths of the pump light and erase light need to be quite short, because many sample molecules (especially, fluorescence labeler molecules) are quite short, or on the nanometer order. Accordingly, where the above-described solid-state dye laser is used, pulsed pump light and erase light with nanometer-order pulses (e.g., shorter than 10 nsec, or even shorter than 1 nsec) shorter than the fluorescence lifetime of the sample molecules (e. g., fluorescence labeler molecules) can be generated by short pulsed laser pumping. Fluorescence can be suppressed effectively.

Furthermore, if the dye molecules of the solid-state dye laser are excited with an ultrashort pulse width on the nanometer order, the laser oscillation efficiency can be enhanced, because the dye molecules do not stay in triplet levels that do not contribute to laser oscillation.

Figure 29:
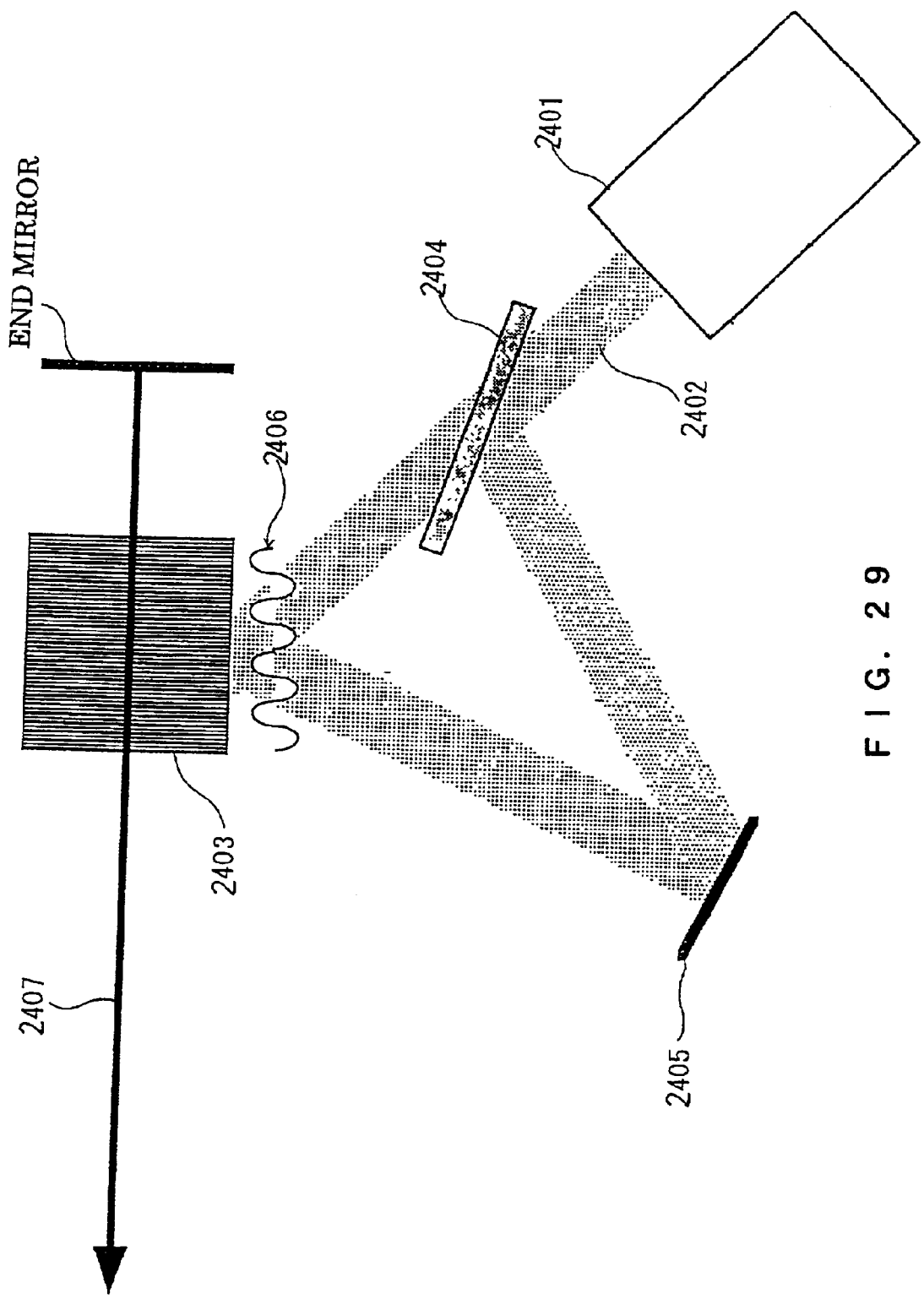
FIG. 29 is a schematic diagram of a solid-state dye laser in accordance with the invention.

Additionally, this solid-state dye laser enables easy wavelength conversion, unlike the prior art liquid dye laser. For example, as shown in FIG. 29, a short pulsed laser 2401 emits dye-pumped light 2402 having a periodic light intensity distribution. If this light 2402 is made to hit one surface of a solid-state laser medium 2403 from two different directions via a half mirror 2404 and via a reflecting mirror 2405, an interference pattern 2406 on the wavelength order of the dye-pumped light 2402 is created. In this structure, an inverted distribution having a periodic structure is formed within the solid-state laser medium 2403. Laser light 2407 is generated in a direction parallel to the surface irradiated with the dye-pumped light 2402 at a wavelength matched to the period. Since the interval between the fringes of the interference pattern is varied by varying the direction of irradiation of the dye-pumped light 2402, the wavelength of the laser light 2407 can be varied. That is, pump light having a wavelength of $\lambda_1$ and erase light having a wavelength of $\lambda_2$ matching the sample molecules (or fluorescence labeler molecules) can be generated simply by varying the direction of irradiation of the dye excitation light 2402. Additionally, both the pump light source and the erase light source can be realized with only one solid-state dye laser by using the laser light from the short pulsed laser 2401 as pump light having a wavelength of $\lambda_1$ and using the laser light from the solid laser medium 2403 as erase light having a wavelength of $\lambda_2$.

The instrument may be so constructed that the laser oscillation wavelength is controlled using an optical grating. Furthermore, a mechanism for scanning the wavelength by controlling the spatial positions of the excitation light and a prism may be added.

As described thus far, the solid-state medium laser in accordance with the present invention has excellent functionality, maintainability, and economy. Where this laser is used as both light sources in a double-resonance-absorption microscope, the serviceability and economy of the microscope system are enhanced. In addition, super-resolution can be accomplished more reliably and easily. In this way, this laser is quite useful for the double-resonance absorption microscope of course, this laser can also be used in fluorescence microscopes and the like other than double-resonance-absorption microscopes.

EXAMPLE 3

Figure 30:
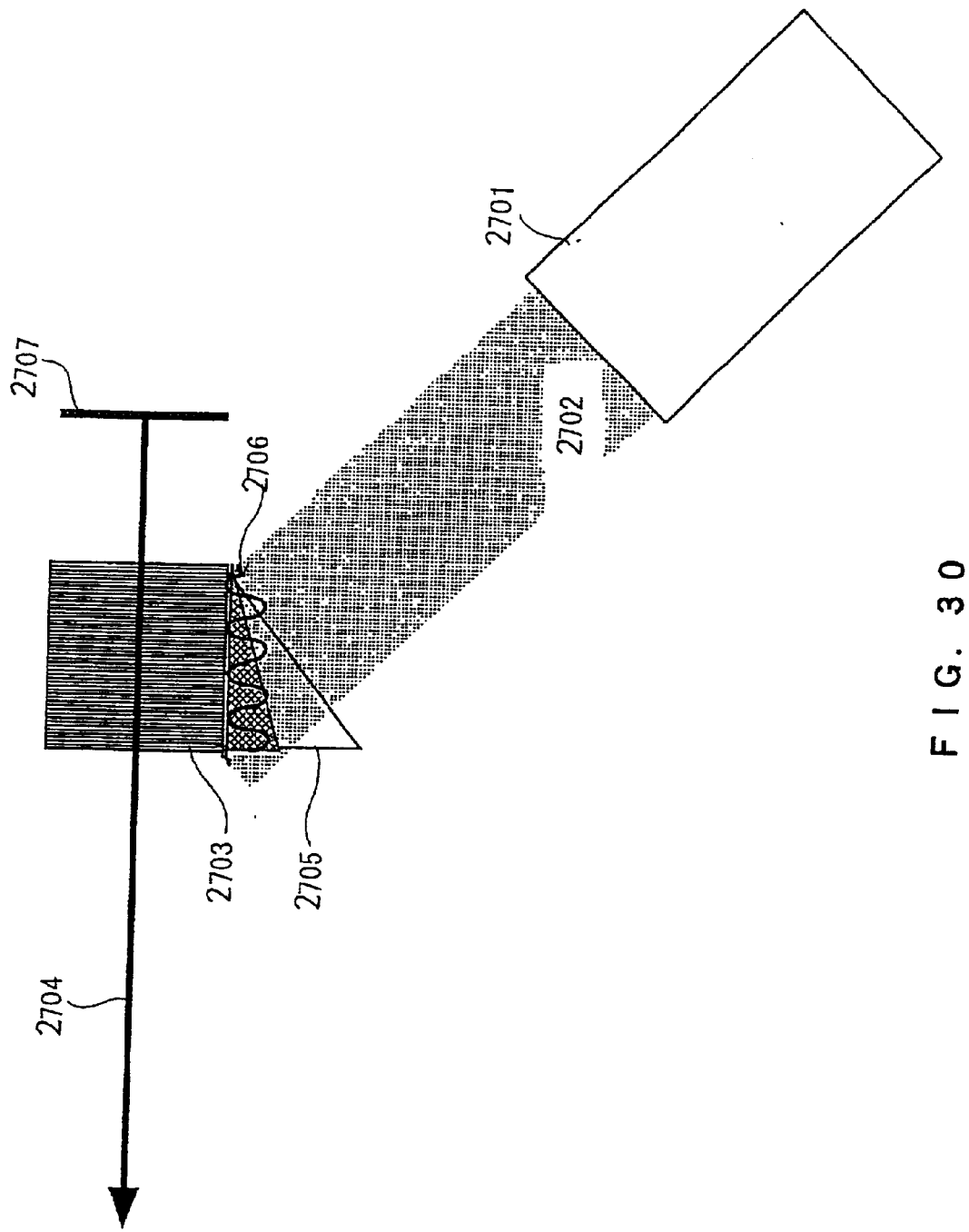
FIG. 30 is a schematic diagram of another solid-state dye laser in accordance with the invention.

FIG. 30 is a schematic diagram showing one example of the solid-state dye laser in accordance with the present invention. This laser is capable of wavelength conversion.

The solid-state dye laser shown in FIG. 30 includes a solid laser medium 2703 having a pumping surface. A prism 2705 is placed in intimate contact with the pumping surface. In this geometry, if dye-pumped light 2702 from a short pulsed laser 2701 acting as an excitation light source is made to hit the pumping surface of the solid-state laser medium 2703 at an angle, the transmitted light and the light reflected inside the prism directly interfere with each other at the boundary surface between the prism 2705 and the solid laser medium 2703. This creates a periodic inverted distribution within the solid laser medium 2703 at the pitch of interference fringes 2706. At this time, if the wavelength of the standing wave within the solid laser medium 2703 satisfies the Bragg condition determined by the pitch of the inverted distribution, then the wavelength meets the resonance condition. As a result, laser light 2704 is generated. The pitch of the interference fringes 2706 can be set to an arbitrary value and the oscillation frequency of the solid laser medium 2703 can be varied by making use of the fact that the pitch of the interference fringes 2706 varies according to the incidence angle of the dye-pumped light 2702.

Therefore, this solid-state dye laser achieves wavelength conversion within the tunable wavelength range of the solid laser medium 2703. If the oscillation wavelength range should be varied, the laser medium may be replaced with a solid laser medium 2703 in which other dye molecules are dispersed. Since it is solid, the replacement is easy to perform. At this time, the concentration of the dye molecules is adjusted so that the resonance conditions remain the same.

In FIG. 30, a resonator is formed by an end mirror 2707. In this structure, the laser pumping conditions are determined by the accuracy at which the end mirror 2707 and the solid laser medium 2703 are machined and by the specifications of the prism 2705. That is, the wavefront of the generated laser light does not depend on the quality of the wavefront of the dye-pumped light 2702 from the short pulsed laser 2701. Accordingly, laser light having a uniform wavefront can be generated by reliably constructing the resonator of the solid-state dye laser. This laser light is passed through the aforementioned phase plate (see FIGS. 19 and 20), whereby erase light having a hollow beam profile optimal for suppression of fluorescence can be created.

In the following specific example, the solid-state dye laser shown in FIG. 30 uses the following solid laser medium 2703 and short pulsed laser 2701. The used sample is a biological one consisting of fluorescence labeler molecules and stained with rhodamine 6G.

First, a block (5 mm×5 mm×5 mm) of rhodamine B in which PMMA (polymethyl methacrylate) is dispersed at a concentration of 1 m mol/l is used as the solid laser medium 2703. The laser pumping surface and the dye-pumped light incident surface of this solid laser medium 2703 are polished almost optically flat.

An Nd:YAG laser is used as the short pulsed laser 2701. In this structure, due to the excitation caused by the second harmonic (532 nm) of the Nd:YAG laser, the conversion efficiency is a maximum where the wavelength generated by the solid laser medium 2703 is about 590 nm. This wavelength range includes the wavelength of $\lambda_2$ necessary for excitation $S_1 \rightarrow S_2$ of rhodamine 6G. The second harmonic (532 nm) is the same as the wavelength $\lambda_1$ of the pump light necessary for excitation $S_0 \rightarrow S_1$ of rhodamine 6G. Therefore, the second harmonic (532 nm) from the Nd:YAG pulsed laser can be used as dye-pumped light and pump light intact. The laser light 2704 generated from the solid laser medium 2703 can be used as erase light. Where the second harmonic from the single Nd:YAG pulsed laser is used as dye-pumped light and as pump light, a light-splitting element such as a half mirror for splitting the second harmonic may be inserted in the optical path of the second harmonic.

FIG. 31 is a schematic representation of another example of the solid-state dye laser in accordance with the present invention. In this example shown in FIG. 31, the wavelength generated from the solid laser medium 2703 is controlled by a diffraction grating 2708 that is an external resonator. In this geometry, the generated wavelength can be selected by rotating the diffraction grating 2708.

Pump light or erase light can be easily produced by using the solid-state dye laser described thus far as a pump light source or an erase light source or both in the double-resonance-absorption microscope in accordance with the invention. Hence, double-resonance absorption and fluorescence suppression can be readily adapted to various sample molecules or fluorescence labeler molecules. Since the excitation light source is the short pulsed laser 2701 capable of producing short pulsed laser light on the subnanometer order as described above, double-resonance absorption and fluorescence suppression can be accomplished more reliably. Because the dispersed dye molecules are not stored in triplet state, the laser oscillation can be performed at high efficiency.

The solid laser medium of the solid-state dye laser can be fabricated by a sol-gel method as mentioned previously. One example of this is described below.

In a sol-gel method, a solution consisting of a metal alkoxide, water, and an alcohol acid is first stirred at an appropriate temperature to cause hydrolysis and depolymerization. The solution changes into a sol in which colloidal particles of a metal oxide appear. If the reaction is progressed further, the entire sol becomes a gel. Any desired shape can be created during this change from sol to gel. For example, a coating film can be fabricated by a dipping method. The material can be shaped into fibrous form by spinning. Furthermore, the material can be shaped into bulky form, powder, granular form, and many other forms. Then, necessary conditions are selected, and the gel is dried. Thus, a porous dry gel is obtained. If this dry gel is heated slowly to an appropriate temperature, the polymerization progresses further, resulting in a metal compound.

Dye molecules are previously dispersed in a glass solution. A solid dye comprising the glass medium doped with dye molecules can be created by the aforementioned process using such a sol-gel method. Furthermore, an organic/inorganic hybrid molecular structure can be imparted to the medium of the solid dye by chemically polymerizing organic molecules with terminal groups of an inorganic compound.

As described in detail thus far, the present invention accomplishes a novel solid-state dye laser that dispenses with cumbersome dye replacement. Where this is used as a pump light source and as an erase light source, a novel double-resonance-absorption microscope having light sources that are excellent in operability and maintainability is offered.

[III] Novel Double-Resonance-Absorption Microscope capable of suppressing mixing of excitation light into a fluorescence signal to thereby prevent deterioration of the S/N and

[IX.a] Novel Double-Resonance-Absorption microscope having excellent three-dimensional spatial resolution.

The present invention provides a double-resonance-absorption microscope having a pump light source for exciting sample molecules from a ground state to a first electronic excited state and an erase light source for exciting the sample molecules in the first electronic excited state to a second or higher electronic excited state. The microscope detects emission of light caused when the excited sample molecules deexcite to the ground state. The pump light has a photon energy less than half of an excitation energy necessary to excite the sample molecules or fluorescence labeler molecules in state $S_0$ to state $S_1$. The erase light has a photon energy less than half of an excitation energy necessary to excite the sample molecules or fluorescence labeler molecules in state $S_1$ to state $S_2$. That is, the double-resonance-absorption microscope in accordance with the invention makes use of a non-resonance-multiphoton excitation process that is one of the non-resonance optical effects.

A non-resonance-multiphoton excitation process in a two-photon case (referred to as "non-resonance two-photon excitation process") is described. Referring to FIG. 32, it is assumed that a substance has two energy levels (electronic excited states) $S_0$ and $S_1$. Let $E_{01}$ be the energy between these two levels. If light of a high photon flux having a photon energy $E_{01}/2$ that is half of the energy $E_{01}$ is made to hit the substance, transition from state $S_0$ to state $S_1$ is permitted. This effect is referred to as a non-resonance-absorption two-photon excitation process.

According to perturbation calculations up to the second order in quantum mechanics, the probability a of transition from state $S_0$ to state $S_1$ during a non-resonance-absorption two-photon excitation process is given by $$|a_2(S_0 \rightarrow S_1)|^2 = \frac{d}{dt}\left(\frac{eF}{h}\right)^4 \cdot \left| \begin{array}{l} x_{j1}\int_0^t \sin(\omega t')\exp(i\omega_{j1})dt' \cdot \\ x_{0j}\int_0^t \sin(\omega t'')\exp(i\omega_{0j})dt'' \end{array} \right|^2 \quad (14)$$

where F sin ($\omega$t) is the amplitude of the excitation light, -er is the electric dipole moment of sample molecules, $\omega$ is the angular frequency of the excitation light, h is Planck's constant, t is time, t' and t" are integral constants of t, $\omega_{j0}$, $w_{1j}'$ are the resonance frequencies of sample molecules where a virtual quantum state j is assumed, and $\chi_{j1}$, $\chi_{0j}$ are matrix elements of the electric dipole moment between the states $S_1$ and $S_2$. $\chi j1$ and $\chi_{0j}$ are given by $$\chi_{km} = \int U_k^* \chi U_m dv \quad (15)$$

where $u_k$, $u_m$ are the wave functions of molecules associated with a transition in ending state k and in starting state m, respectively.

On the other hand, in the case of a normal, one-photon excitation process, the excitation, or transition, is done without any virtual intermediate state. The probability of this transition is given by the following formula using the first-order perturbation theory:

$$|a_1(S_0 \to S_1)|^2 = \frac{d}{dt}\left(\frac{eF}{h}\right)^2 \cdot \left|x_{01}\int_0^t \sin(\omega t')\exp(i\omega_{01}t')dt'\right|^2 \quad (16)$$

As can be seen by comparing FIGS. (14) and (16), the probability of transition $S_0 \to S_1$ is in proportion to the fourth power of the amplitude, or magnitude, of the excitation light in the case of a non-resonance two-photon excitation process (in other words, in proportion to the square of the amplitude of the excitation light). In the case of a one-photon excitation process, the probability is in proportion to the square of the amplitude of the excitation light (in other words, the probability is linearly proportional to the magnitude of the excitation light). That is, in the case of a non-resonance two-photon excited process, the intensity of fluorescence is almost in proportion to the square of the intensity of the excitation light. In the case of a one-photo excited process, the fluorescence intensity is linearly proportional to the magnitude.

Accordingly, a fluorescence signal with quite excellent S/N can be obtained by combining such a non-resonance two-photon excited process with a double-resonance absorption process, i.e., by using a non-resonance two-photon excited process for transition $S_0 \to S_1$ and for transition $S_1 \to S_2$.

Figure 33:
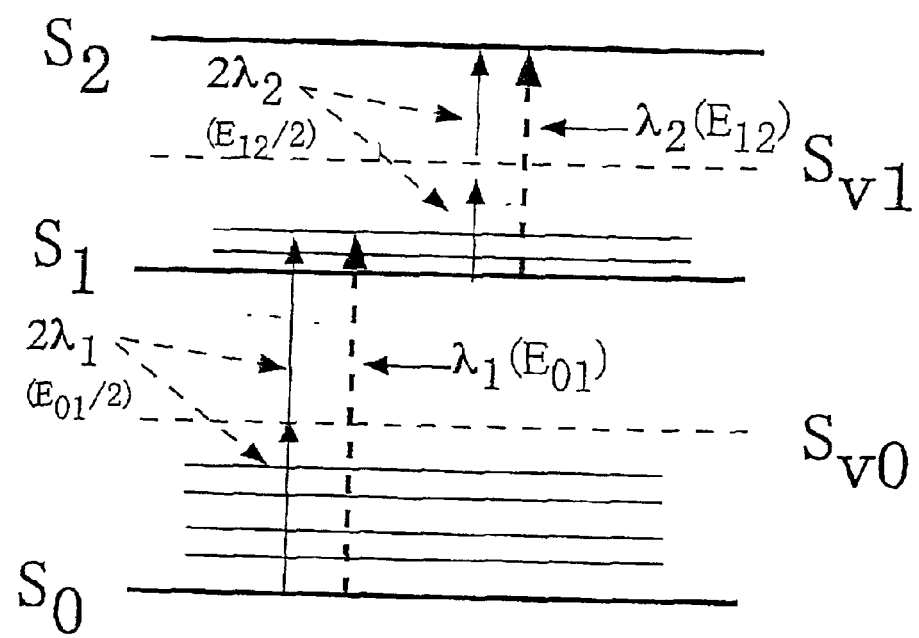
FIG. 33 is a conceptual diagram of a double-resonance absorption process using a non-resonance-two-photon excitation process in accordance with the present invention.
Figure 34:
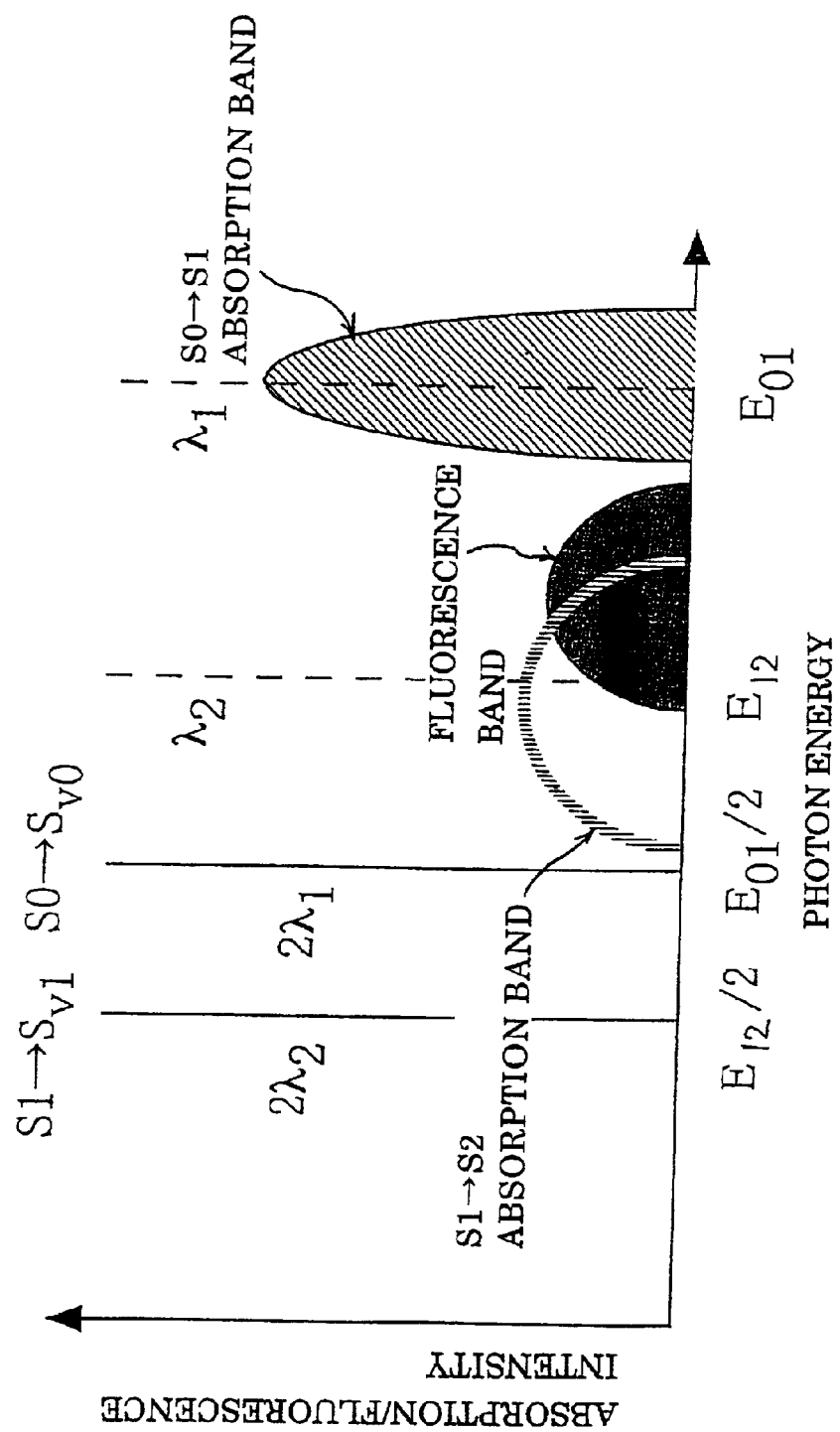
FIG. 34 is a diagram illustrating the relation among excitation light, an absorption band, and a fluorescence band.

This principle is described by referring to FIGS. 33 and 34. FIG. 33 conceptually illustrates combinations of double-resonance absorption processes and non-resonance two-photon excited processes, together with an energy diagram of fluorescence labeler molecules. FIG. 34 illustrates the relation between the photon energy of excitation light and an absorption/fluorescence spectrum of sample molecules.

Referring first to FIG. 33, one kind of pump light has a photon energy $E_{01}/2$ that is half of the energy necessary for normal transition $S_0 \to S_1$. Where this photon energy is converted into a wavelength, this is $2\lambda_1$, which is twice as long as the wavelength occurring during normal transition $S_0 \to S_1$. Using this pump light, excitation is made from state $S_0$ to state $S_1$ via a virtual level $S_{v0}$. Subsequently, excitation from $S_1$ to $S_2$ is made via a virtual level $S_{v1}$, using erase light having a photon energy $E_{12}/2$ that is half of the energy necessary for normal transition $S_1 \to S_2$. Where this photon energy is converted into a wavelength, this is $2\lambda_2$, which is twice as long as the wavelength occurring during normal transition $S_1 \to S_2$. The erase light of energy $E_{12}/2$ is directed to the sample after the pump light of energy $E_{01}/2$ is irradiated and before molecules in state $S_1$ fluoresce.

When only a double-resonance-absorption process occurs as shown in FIG. 34, the photon energy $E_{01}$ of the pump light having a wavelength of $\lambda_1$ belongs to absorption band $S_0 \to S_1$. The photon energy $E_{12}$ of the erase light having a wavelength of $\lambda_2$ belongs to absorption band $S_1 \to S_2$ and to the fluorescence band. On the other hand, the photon energy $E_{01}/2$ of the pump light having wavelength $2\lambda_1$ and the photon energy $E_{12}/2$ of the erase light having wavelength $2\lambda_2$ belong to none of the absorption band $S_0 \to S_1$, absorption band $S_1 \to S_2$, and the fluorescence band.

Accordingly, the excited wavelength is placed in an energy range much lower than the fluorescence band by creating sample molecules in state $S_1$ with the pump light having wavelength $2\lambda_1$ and photon energy $E_{01}/2$, and by exciting the molecules to state $S_2$ with the erase light having wavelength $2\lambda_2$ and photon energy $E_{12}/2$ before the molecules in state $S_1$ fluoresce. The excited wavelength does not overlap the fluorescence band. Hence, the excitation light is not mixed in as background light. Consequently, a fluorescence signal with quite high S/N can be obtained.

A non-resonance two-photon excitation process is used for any one of excitations $S_0 \to S_1$ and $S_1 \to S_2$. That is, any one of the pump light and erase light can have a photon energy that is half the excitation energy. This is advantageous if the wavelength for normal excitation $S_0 \to S_1$ overlaps the fluorescence band, or if the wavelength for normal excitation $S_1 \to S_2$ overlaps the fluorescence band.

The description provided thus far concerns a two-photon, non-resonance, multiphoton excitation process. Similarly, where a non-resonance-absorption excitation process in which three or more photons are associated is used, the double-absorption multiphoton excitation process in accordance with the present invention can effectively prevent mixing of the excitation light. In the nth-order non-resonance multiphoton excitation process, the pump light and erase light have photon energies that are $1/n$ of the energies necessary for normal excitation $S_0 \to S_1$ and excitation $S_1 \to S_2$, respectively. For example, in a non-resonance three-photon excitation process involving three photons, the photon energies of the pump light and the erase light are only one-third of the excitation energy.

Many fluorescence labeler molecules use photon energies during non-resonance multiphoton excitation processes. So-called normal electronic excited levels other than virtual levels do not exist. Therefore, the molecules are transparent to pump light and to erase light. By making use of this property, a super-resolution microscope having quite excellent performance can be accomplished.

Depth resolution in the direction of the optical axis can be imparted to the double-resonance-absorption microscope by using this non-resonance multiphoton excited process. That is, three-dimensional spatial resolution can be imparted to the instrument. For the sake of simplicity, a non-resonance two-photon excitation process is taken as an example.

It is assumed that excitation light has a wavelength of $\lambda_1$. An achromatic optical system is used as a focusing lens. If the light of the wavelength $\lambda_1$ is collected by the whole aperture (having a numerical aperture of NA) of the optical system, the three-dimensional complex amplitude distribution I (x, y, z) in the image space (x, y, z) is given by $$I(x, y, z) = \int_N \int_A e^{-\frac{z}{2f^2}(\xi^2+\zeta^2)} e^{-i\frac{2\pi}{\lambda}(x\xi+y\zeta\eta)} d\xi d\zeta \quad (17)$$

where f is the focal distance and $(\xi, \zeta)$ are coordinates in the pupil plane. Integration is performed over the whole aperture.

According to Eq. (16) above, if the light of the wavelength $\lambda_1$ is irradiated to excite sample molecules to state $S_1$ by a normal one-photon excitation process, the amount of excited molecules $q_{one}$ (x, y, z) is in proportion to I (x, y, z)$^2$. According to Eq. (17), if sample molecules are excited by light having a wavelength of $2\lambda_1$ by means of a non-resonance two-photon excitation process, the amount of excited molecules $q_{two}$ (x, y, z) is in proportion to I (x, y, z)$^4$. If $q_{one}$ (x, y, z) and $q_{two}$ (x, y, z) are normalized and Fourier-trans formed into a frequency space, they are changed into physical amounts (3D OTF) indicating actually observable resolutions. Let $Q_{one}$ (x, y, z) and $Q_{two}$ (x, y, z) be the normalized amount of excited molecules during the one-photon excitation process and the normalized amount of excited molecules during the non-resonance two-photon excited process, respectively. Then, relations given by Eqs. (18) and (19) are obtained:

$$s_{one}(k1_x, k1_y, k1_z) = \qquad (18)$$
$$\iiint Q_{one}(k1_x, k1_y, k1_z)e^{-(xk1_x + yk1_y + zk1_z)}dxdydz$$

$$s_{two}(k2_x, k2_y, k2_z) = \qquad (19)$$
$$\iiint Q_{two}(k2_x, k2_y, k2_z)e^{-(xk2_x + yk2_y + zk2_z)}dxdydz$$

where $k1_x$, $k1_y$, and $k1_z$ are wave-vector components for excitation light having a wavelength of $\lambda_1$, and $k2_x$, $k2_y$ and $k2_z$ are wave-vector components for excitation light having a wavelength of $2\lambda_1$.

Assuming that the pupil plane is symmetrical with respect to the optical axis, a parameter $r = \sqrt{x^2 + y^2}$ is introduced. Cross sections of spatial distributions of $(k1_r, k1_z)$ and $(k2_r, k2_z)$ are foundusing Eqs. (18) and (19), respectively. The results are shown in FIGS. 35(a) and 35(b) respectively. $k1_f$ and $k2_f$ are the wave-vector components of the light having a wavelength of $\lambda_1$ and the light having a wavelength of $2\lambda_1$, taken in the radial direction from the optical axis.

According to FIGS. 35(a) and 35(b), irrespective of whether the process is a non-resonance two-photon excitation processor a one-photon excitation process, the upper limit Kmax and the lower limit Kmin of the spatial frequency range in the radial direction are given by $$K\max = -K\min = 2\frac{NA}{\lambda 1} \qquad (20)$$

where NA is the numerical aperture of the optics. They are substantially identical in spatial resolution but differ considerably in resolution in the direction of the optical axis. During the one-photon excitation process, there are no values in the direction of axis $k1_z$ including the origin. This indicates that no resolution exists at all in the direction of the optical axis. On the other hand, during the non-resonance two-photon excitation process, there are values given by $$K\max = -K\min = \frac{\left(1 - (1 - NA^2)^{\frac{1}{2}}\right)}{\lambda 1} \qquad (21)$$

even in the direction of $k2_z$ that is the direction of the optical axis. That is, there is a depth resolution in the direction of the optical axis. This corresponds to the fact that excited molecules are confined to within a quite narrow space region, because the amount of molecules excited to state $S_1$ is in proportion to the square of the amplitude of the excitation light as indicated by Eq. (14).

Accordingly, when molecules excited to state $S_1$ are created, a non-resonance two-photon excitation process is used. That is, pump light is used which has a photon energy that is half of the excitation energy for exciting sample molecules in a ground state to state $S_1$. Thus, depth resolution in the direction of the optical axis can be imparted to the double-resonance absorption microscope.

If the double-resonance absorption microscope is designed so that if a region that emits when sample molecules in state $S_1$ deexcite to a ground state is partially suppressed by directing pump light and erase light to the sample via an overlapping means as mentioned previously, the instrument can have depth resolution, as well as excellent 2D resolution. Hence, a super-resolution microscope of quite high performance is accomplished. The overlapping means causes a region irradiated with the pump light to overlap with the region irradiated with erase light. For example, the overlapping means is an optical system including a phase plate for shaping the erase light into a hollow beam.

Of course, the theory described thus far can be similarly applied to erase light used to excite molecules from state $S_1$ to state $S_2$. Three-dimensional spatial resolution can be accomplished by setting the photon energy to half of the excitation energy necessary for normal excitation $S_1 \rightarrow S_2$. Also, where a non-resonance multiphoton excitation process in which three or more photons are involved is used, three-dimensional spatial resolution can be similarly attained by setting the photon energies of the pump light and erase light to $1/n$.

With some fluorescence labeler molecules for staining samples, the excitation light wavelength is close to or overlaps the fluorescence wavelength during a one-photon excitation process. Examples of these labeler molecules are listed below. Where a sample is stained with these fluorescence labeler molecules, the above-described effect of the present invention arising from a non-resonance two-photon excitation process (i.e., improvement of the S/N of the fluorescence signal into which background light is not mixed) is made more conspicuous.

Examples of Fluorescence Labeler Molecules 2,2"-Dimethyl-p-terphenyl:
P-terphenyl(PTP):
3,3',2",3"-Tetramethyl-P-quaterphenyl:
2,2""-Dimethyl-P-quaterphenyl:
2-Methyl-5-t-butyl-p-quaterphenyl:
2-(4-Biphenylyl)-5-(4-t-butylphenyl)-1,3,4 2-(4-Biphenylyl)-phenyl-1,3,4-oxadiazol:
2,5,2""5,""'-Tetramethyl-p-quinquephenyl: 3,5,3""5,""'-Tetra-t-butyl-p-quinquephenyl:
2,5-Diphenyloxazol:
oxiazol(BPBD-365
2,5-Diphenylfuran: PQP(p-Quanterphenyl: 2,5-Bis-(4-biphenylyl)-1,3,4-oxadiazol:
p-Quaterphenyl-4-4""-disulfonicacid Disodiumsalt: p-Quaterphenyl-4-4""-disulfonicacid
Dipotassiumsalt: 4,4""-Bis-(2-butyloctyloxy)-p-quanterphenyl:
3,5,3""5,""'-Tetra-t-butyl-p-sexiphenyl: 2-(1-Naphthyl)-5-phenyloxazol:
2-(4-Biphenylyl)-6-phenylbenzoxazotetrasulfonicacid Potassium Salt:
2-(4-Biphenylyl)-6-phenylbenzoxazol-1,3: 4,4'-Diphenylstilbene: [1,1'-Biphenyl]-4-sulfonic acid,
4,4"-1,2-ethene-diylbis-,dipotassium salt: 2,5-Bis-(4-biphenylyl)-oxazol:
2,2'-([1,1'-Biphenyl]-4,4'-diyldi-2,1-ethenediyl)-bis-benzenesulfonic acid Disodium Salt:
7-Amino-4-methylcarbostyryl: 1,4-Di[2-(5-phenyloxazoly)] benzene:
7-Hydroxy-4-methylcoumarin: p-Bis(o-methylstyryl)-benzene:
Benzofuran,2,2'-[1,1'-biphenyl]-4,4'-diyl-bis-tetrasulfonicacid:
7-Dimethylamino-4-methylquinolom-2: 7-Amino-4-methylcoumarin:
2-(p-Dimethylaminostyryl)-pyridylmethyl Iodide: 7-Diethylaminocoumarun:
7-Diethylamino-4-methylcoumarin:
2,3,5,6-1H,4H-Tetrahydro-8-methylginolizino-[9,9a,1-gh]-coumarin:
7-Diethylamino-4-trifluormethylcoumarin: 7-Dimethylamino-4-trifluormethylcoumarin:

7-Amino-4-trifluormethylcoumarin: 2,3,5,6-1H,4H-Tetrahydroquinolizino-[9,9a,1-gh]-coumarin:
7-Ethylamino-6-methyl-4-trifluormethylcoumarin: 7-Ethylamino-4-trifluormethylcoumarin:
2,3,5,6-1H,4H-Tetrahydro-9-carboethoxyquinolizino-[9,9a,1gh]coumarin
2,3,5,6-1H,4H-Tetrahydro-9-(3-pyridyl)-quinolizio-[9,9a,1gh]coumarin
3-(2'-N-Methylbenzimidazolyl)-7-n,n-diethylaminocoumarin:
2,3,5,6-1H,4H-Tetrahydro-9-acetylquinolizino-[9,9a,1-gh]-coumarin:
N-Methyl-4-trifluormethylpiperidino-[3,2-g]-coumarin:
2-(p-Dimethylaminostyryl)-benzothiazolylethyl Iodide:
3-(2'-Benzimidazolyl)-7-N,N-diethylaminocoumarin: Brillantsulfaflavin:
3-(2'-Benzothiazolyl)-7-diethylaminocoumarin:
2,3,5,6-1H,4H-Tetrahydro-8-trifluormethylquinolizino-[9,9a,1gh]coumarin:
3,3'-Diethyloxacarbocyanine Iodide: 3,3'-Dimethyl-9-ethylthiacarbocyanine Iodide: Disodium
Fluorescein (Uranin): 9-(o-Carboxyphenyl)-2,7-dichloro-6-hydroxy-3H-xanthen-3-on2
7-Dichlorofluorescien,Fluorescein 548: Fluorol 555 (Fluorol 7GA):
O-(6-Amino-3-imino-3H-xanthen-9-yl)-benzonic acid (Rhodamine 560)
BenzoicAcid,2-[6-(ethylamino)-3-(ethylamino)-2,7-dimethyl-3H-xanthen9-yl],perchlorate(Rhodamine 575):
Benzonic Acid,2-[6-(ethylamino)-3-(ethylamino)-2,7-dimethyl-3X-xanthen-9-yl]-ethylester, monohydrochloride (Rhodamine 590):
1,3'-Diethyl-4,2'-quinolyloxacarbocyanine Iodide: 1,1'-Diethyl-2,2'-carbocyanine Iodid:
2-[6-(diethylamino)-3-(diethylimino)-3H-xanthen-9-yl] benzon is acid (Rhodamine 610):
Ethanaminium,N-[(6-diethylamino)-9-(2,4-disulfophenyl)-3H-xanthen-3-ylidene)-N-ethylhydroxid,inner salt, sodium salt: Malachit Green:
3,3'-Diethylthiacarbocyanine Iodide: 1,3'-Diethyl-4,2'-quinolylthiacarbocyanine Iodide:
8-(2-Carboxyphenyl)-2,3,5,6,11,12,14,15-octahydro-1H,4H,10H,13H-diquinolizino[9,9a,1-bc:9',9a',1-hi]xanthylium Perchlorate (Rhodamine 640) 4-Dicyanmethylene-2-methyl-6-(p-dimethylaminostyryl)-4H-pyran:
3,3'-Diethyloxadicarbocyanine Iodide:
8-(2,4-Disulfophenyl)-2,3,5,6,11,12,14,15-octahydro-1H,4H,1 OH,13H-diquinolizino[9,9a,1-bc:9',1-hi]xanthene (Sulforhodamine 640):
5,9-Diaminobenzo[a]phenoxazonium Perchorate: 9-Diethylamino-5H-benzo(a)phenoxazin-5-one:
5-Amino-9-diethylimino(a)phenoxazonium Perchlorate:
3-Ethylamino-7-ethylimino-2,8-dimethylphenoxazin-5-ium Perchorate:
8-(Trifluoromethyl)-2,3,5,6,11,12,14,15-octahydro-1H,4H,1OH13H-diquinolizino[9,9a,1-bc:9',9a,1-hi]xanthylium Perchlorate:
1-Ethyl-2-(4-(p-Dimethylaminophenyl)-1,3-butadienyl)-pyridinium Perchlorate:
Carbazine 122: 9-Ethylamino-5-ethylimino-10-methyl-5H-benzo(a)phenoxazoniumPerchlorate:
3-Diethylamino-7-diethyliminophenoxazonium Perchlorate: 3-Diethylthiadicarbocyanine Iodide:
Oxazine 750: 1-Ethyl-4-(4-(p-Dimethylaminophenyl)-1,3-butadienyl)-pyridininum Perchlorate:
1,1',3,3,3',3'-Hexamethylindodicarbocyanine Iodide: 1,1'-Diethyl-4,4'-carbocyanine Iodide:
2-(4-(p-Dimethylaminophenyl)-1,3-butadienyl)-1,3,3-trimethy 1-3H-indolium Perchlorate:
2-(4-(p-Dimethylaminophenyl)-1,3-butadienyl)-3-ethylbenzoth oazolium Perchlorate:
1,1'-Diethyl-2,2'-dicarbocyanine Iodide:
1-Ethyl-4-(4-(9-(2,3,6,7-tetrahydro-1H,5H-benzo(i,j)-chinolinozinium))-1,3-butadienyl)-pyridinium Perchlorate: 3,3'-DimethyloxatricarbocyanineIodide:
1-Ethyl-4-(p-Dimethylaminophenyl)-1,3-butadienyl)-quinolinium Perchlorate:
8-Cyano-2,3,5,6,11,12,14,15-octahydro-1H,4H,10H,13H-diquinolizino[9,9a,1-bc:9a',1-hi]xanthylium Perchlorate (Rhodamine800):
2-(6-(4-Dimethylaminophenyl)-2,4-neopentylene-1,3,5)-3-methylbenzothiazoliumPerchlorate:
1,1',3,3,3',3'-Hexamethylindotricarbocyanine Iodide: IR125
3,3'-Diethylthiatricarbocyanine Iodide IR144
2-(6-(9-(2,3,6,7,-Tetrahydro-1H,5H-benzo(i,j)-chinolizinium-2,4-neopentylene-1,3,5-hexatrienyl)-3-methyllbenzothiazolium Perchlorate:
3,3'-Diethyl-9,11-neopentylenethiatricarbocyinine Iodide:
1,1',3,3,3',3'-Hexamethyl-4,4',5,5'-dibenzo-2,2'-indotricarbocyanine Iodide:
3,3'-Diethyl-4,4',5,5'-dibenzothiatricarbocyanine Iodide: 1,2'-Diethyl-4,4'-dicarbocyanine Iodide:
IR140: 2-(8-(4-p-Dimethyhlaminophenyl)-2,4-neopentylene-1,3,5,7-octatetraenyl)-3-methylbenzothiazolium Perchlorate:
IR132 2-(8-(9-(2,3,6,7-Tetrahydro-1H,5H-benzo(i,j) chinolizinium))-2,4-neopentylene-1,3,5,7-octatetraenyl)-3-methylbenzothiazolium Perchlorate:
IR26:
IR 5

Embodiments of the present invention are described with reference to the accompanying drawings. The invention is described in further detail using these embodiments.

EXAMPLE 4

Figure 36:
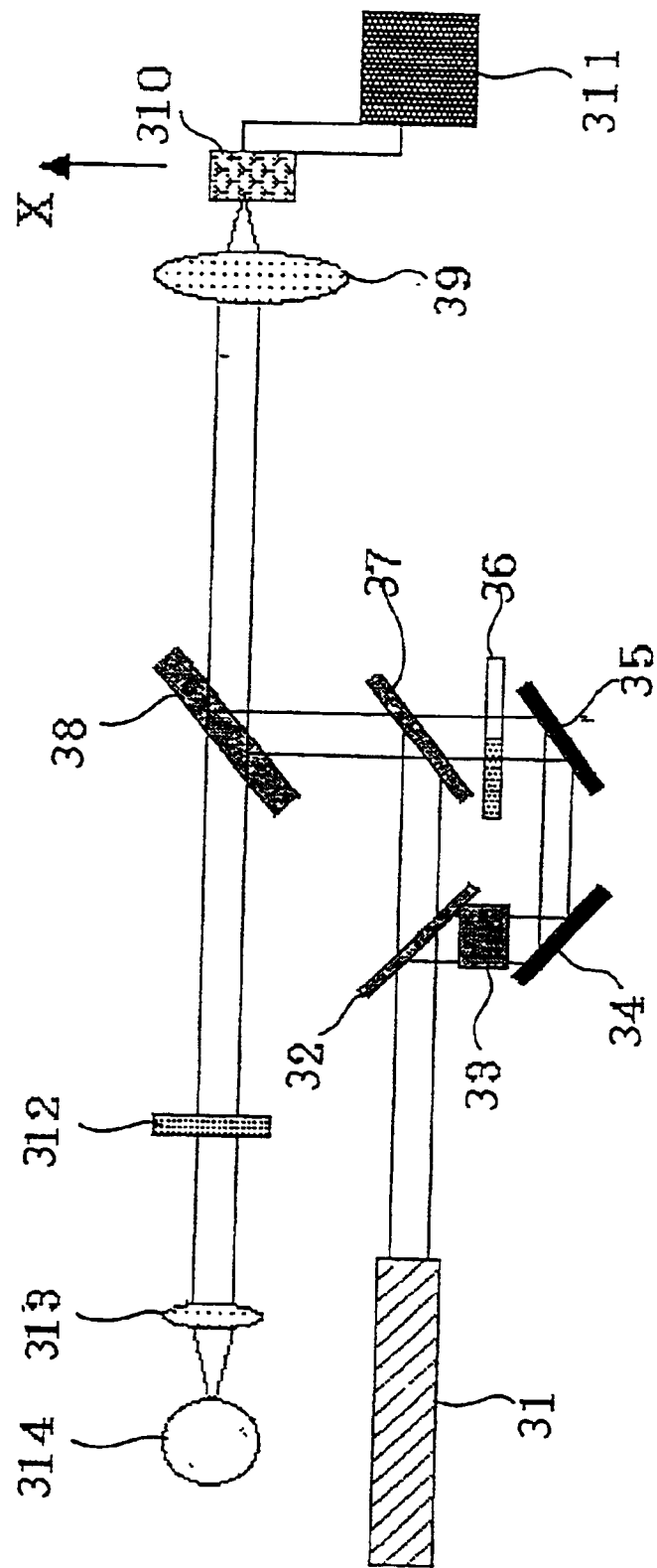
FIG. 36 is a schematic diagram of a double-resonance-absorption microscope in accordance with the invention.

FIG. 36 is a diagram showing the main portions of the structure of one example of a double-resonance absorption microscope in accordance with the present invention. The double-resonance absorption microscope shown in FIG. 36 constitutes a laser scanning fluorescence microscope and can effect partial overlap between the regions irradiated with pump light and erase light, respectively, as well as utilization of a double-resonance absorption process and a non-resonance multiphoton excitation process. This double-resonance absorption microscope shown in this FIG. 36 comprises a light source, a sample observation system, and a detection system which are separately described in the following sections [III/IX.a-1], [III/IX.a-2], and [III/IX.a-3], respectively. The non-resonance multiphoton excitation process exploits a non-resonance two-photon excitation process. The sample 10 is a biological one that acts as fluorescence labeler molecules and is stained with rhodamine 6G.

[III/IX.a-1] Light Source

As a fundamental light source, an Nd:YAG laser 31 using a supersaturated dye and emitting picosecond pulsed laser light is used. Its fundamental wave has a wavelength of 1064 nm and a photon energy of about 1.165 eV. Pump light and erase light are generated from the fundamental wave. A conversion formula photon (electron) energy (eV)=1239.8 wavelength (nm) is used.

[III/IX.a-1.a] Pump Light

The pump light will be described first. To excite rhodamine 6G from state $S_0$ to $S_1$ by a normal one-photon excitation process, a photon energy $E_{01}$ of about 2.3 eV is necessary. Rhodamine 6G starts absorption band $S_0 \to S_1$ at about 550 nm, i.e., about 2.25 eV where converted into a photon energy (see FIG. 10). Therefore, rhodamine 6G can be excited from state $S_0$ to $S_1$ by a non-resonance two-photon excitation process and by using the fundamental wave from the Nd:YAG laser 31, the fundamental wave having a wavelength of $2\lambda_1$=about 1064 nm and a photon energy $E_{01}/2$=about 1.165 eV.

The pump light has a photon energy $E_{01}/2$ and a wavelength of $2\lambda_1$. The intensity of this pump light which is necessary to excite rhodamine 6G by a non-resonance two-photon excitation process from state $S_0$ to $S_1$ is described. In Eq. (14) above, let the photon flux of the pump light having a wavelength of $2\lambda_1$ be I ($2\lambda_1$). The number of fluorescence labeler molecules exited from state $S_0$ to $S_1$ by a non-resonance two-photon excitation process in a unit time is given by $$\frac{dn_1(t)}{dt} = a_2(S_0 \to S_1)n_0(t) \quad (22)$$

where $n_0(t)$ and $n_1(t)$ are the number of fluorescence labeler molecules in state $S_0$ and the number of fluorescence labeler molecules in state $S_1$, respectively, per unit volume when time t has elapsed since irradiation of the laser light. A physical amount $\sigma_{01}$ ($2\lambda_1$) is defined as given by Eq. (23) and termed the absorption cross section in a non-resonance two-photon excitation process.

$$\sigma 01(2\lambda_1) = \frac{a_2(S_0 \to S_1)}{I(2\lambda_1)^2} \quad (23)$$

Let $N_0$ be the number of fluorescence labeler molecules per unit volume. The differential equation of Eq. (22) can be solved into the form:

$$n_1(t) = N_0[1-\exp\{-\sigma_{01}, (2\lambda_1)I(2\lambda_1)^2 t\}] \quad (24)$$

If the relation given in Eq. (25) below is satisfied, most fluorescence labeler molecules are excited to state $S_1$, and an amount of emission necessary for observation of fluorescence can be obtained.

$$\sigma_{01}(2\lambda_1)I(2\lambda_1)^2 t \sim 1 \quad (25)$$

For example, if the pulse width t of the laser light from the Nd:YAG laser 31 is assumed to be about 30 psec, the absorption cross section $\sigma_{01}$ ($2\lambda_1$) of rhodamine 6G in a non-resonance two-photon excitation process is less than approximately $10^{-50}$ cm$^4$ sec/photon. Therefore, the photon flux I ($2\lambda_1$) of the laser light necessary to excite rhodamine 6G from state $S_0$ to state $S_1$ by a non-resonance two-photon excitation process is less than about $10^{30}$ photons/cm$^2$/sec. Where the fundamental wave from the Nd:YAG laser 31 having a pulse width t of approximately 30 psec is focused into a submicrometer size, the intensity of the laser per pulse is less than 10 nJ/pulse. This can be sufficiently supplied from a commercially available Nd:YAG laser. Consequently, another advantage is that an economical, easily available laser can be used in anon-resonance two-photon excitation process.

[III/IX.a-1.b] Erase Light

Erase light is next described. To excite rhodamine 6G from state $S_1$ to state $S_2$ by a normal one-photon excitation process, a photon energy $E_{12}$ of about 1.92 eV is necessary. Rhodamine 6G starts absorption band $S_1 \to S_2$ at about 640 nm, i.e., about 1.94 eV where converted into a photon energy. Accordingly, the fundamental wave from the Nd:YAG laser 31 is converted into a wave having a wavelength $2\lambda_2$ of about 1197 nm and a photon energy $E_{12}/2$ of about 1.036 eV. This is used as erase light. In this way, rhodamine 6G can be excited from state $S_1$ to $S_2$ during a non-resonance two-photon excitation process.

This erase light can be created from the Nd:YAG laser 31 using a Raman shifter 33 consisting of a crystal of $Ba(NO_3)_2$ in the same way as in the technique disclosed in Japanese patent application No. 97924/1998. Where laser light is passed through the Raman shifter 33 consisting of a crystal of $Ba(NO_3)_2$, Stokes lines successively shifted to the lower-frequency side by a wave number of 1045 cm$^{-1}$ are produced. These Stokes lines are completely coherent. If the fundamental wave of a wavelength of 1064 nm from the YAG laser 31 is entered, the first-order Stokes line having a wavelength of 1197.4 nm is generated. If rhodamine 6G is excited from state $S_1$ to $S_2$ with this first-order Stokes line by a non-resonance two-photon excitation process, then interlevel transition with a gap of about 599 nm (photon energy of 2.07 eV) is achieved. Accordingly, for-rhodamine 6G the first-order Stokes line having a wavelength of 1197 nm can be used as erase light.

Subsequently, the necessary intensity of erase light having a photon energy of $E_{12}/2$ and a wavelength of $2\lambda_2$ (i.e., the intensity necessary to excite rhodamine 6G from state $S_1$ to state $S_2$ by a non-resonance two-photon excitation process) is described.

First, irradiation of pump light and erase light and measurement of a fluorescence signal are carried out at a timing as illustrated in FIG. 37, which depicts the irradiation and measurement timing used in the time division measurement method disclosed in the above-cited Japanese patent application No. 97924/1998. This time division measurement method is especially advantageous where the pulse widths $t_p$ and $t_e$ of pump light and erase light, respectively, are shorter than the lifetime $\tau$ of fluorescence of fluorescence labeler molecules. First, fluorescence labeler molecules are excited from state $S_0$ to $S_1$ with the pump light having a pulse width of $t_p$. Immediately after irradiation of the pump light, the erase light having a pulse width of $t_e$ is irradiated to excite fluorescence labeler molecules from state $S_1$ to state $S_2$. At this time, in the present embodiment, the regions irradiated with the pump light and erase light, respectively, are made to overlap each other partially to suppress fluorescence from spatial regions that do not need to be observed (see FIG. 6). Then, the fluorescence signal from the fluorescence region $A_0$ other than the fluorescence-suppressed region $A_1$ is detected during the time $t_g$ from the instant when the irradiation of the erase light ends to the instant when emission of the fluorescent labeler molecules ends.

This irradiation and measurement timing is assumed. Let $n_1(t_p)$ be the number of molecules in state $S_1$ created when the pump light is irradiated during the time $t_p$ according to Eq. (24). The number of molecules in state $S_1$ when the erase light is irradiated during the time $t_e$ is given by the following derivative equation:

$$\frac{dn_1(t)}{dt} = -[a_2(S1 \to S2) + a_2(f)]n_1(t) \quad (26)$$

where $a_2(S_1 \to S_2)$ and $a_2(f)$ are the probability of transition $S_1 \to S_2$ and the stimulated emission probability, respectively, by a non-resonance two-photon excitation process. With respect to the transition probability and stimulated emission probability, cross sections $\sigma_{12}(2\lambda_2)$ and $\sigma_f(2\lambda_2)$ are defined. Solving Eq. (26) gives rise to $$n_1(t_e) = n_1(t_p)\exp[-\{\sigma_f(2\lambda_{12})+\sigma_f(2\lambda_2)\}I(2\lambda_2)^2 t_e] \qquad (27)$$

where $n_1(t_e)$ is the number of fluorescence labeler molecules in state $S_1$ within a unit volume in the fluorescence-suppressed region $A_1$. The fluorescence labeler molecules emit fluorescent light from the fluorescence-suppressed region $A_1$ in proportion to the number $n_1(t_e)$. Therefore, in order to enhance super-resolution, the number $n_1(t_e)$ of fluorescence labeler molecules in the fluorescence-suppressed region $A_1$ needs to be reduced to a minimum. For example, it is suppressed to below 10% of the number $n_1(t_e)$ of fluorescence labeler molecules in the fluorescence-suppressed region $A_1$. In this case, Eq. (27) leads to $$0.1 \geq \frac{n_1(t_e)}{n_1(t_p)} = \exp[-\{\sigma_f(2\lambda_{12})+\sigma_f(2\lambda_2)\}I(2\lambda_2)^2 t_e] \qquad (28)$$

Rewriting this results in $$\{\sigma_f(2\lambda_{12})+\sigma_f(2\lambda_2)\}I(2\lambda_2)^2 t_e \geq 2.3 \qquad (29)$$

In the case of rhodamine 6G, $\sigma_{12}(2\lambda_2)+\sigma_f(2\lambda_2)$ is on the order of $10^{-50}$ cm$^4$ sec/photon at a wavelength of 599 nm. It is assumed that the erase light has a pulse width $t_e$ of 30 psec. A calculation using Eq. (29) indicates that the photon flux I $(2\lambda_2)$ necessary for the erase light is about $10^{30}$ photons/cm$^2$/sec similarly to the pump light.

Therefore, the pump light having the required intensity, a photon energy of $E_{01}/2$, and a wavelength of $2\lambda_1$ and the erase light having the required intensity, a photon energy of $E_{12}/2$, and a wavelength of $2\lambda_2$ can be generated with a single Nd:YAG laser 31. In the example of FIG. 36, the fundamental wave from the single Nd:YAG laser 31 is split into two by a half mirror 32. The transmitted light is used as pump light, while the reflected light is wavelength-converted by the Raman shifter 33 as mentioned previously and used as erase light.

The erase light obtained in this way is entered into a dichroic mirror 37 acting as a beam combiner by reflecting mirrors 34 and 35 placed behind the Raman shifter 33. The reflecting mirrors 34 and 35 are coated with an interference film. The unwanted fundamental wave from the YAG laser 31 that is not wavelength-converted may be cut by the Raman shifter 33.

[III/IX.a-1.a] Overlapping of Pump Light and Erase Light

Figure 38:
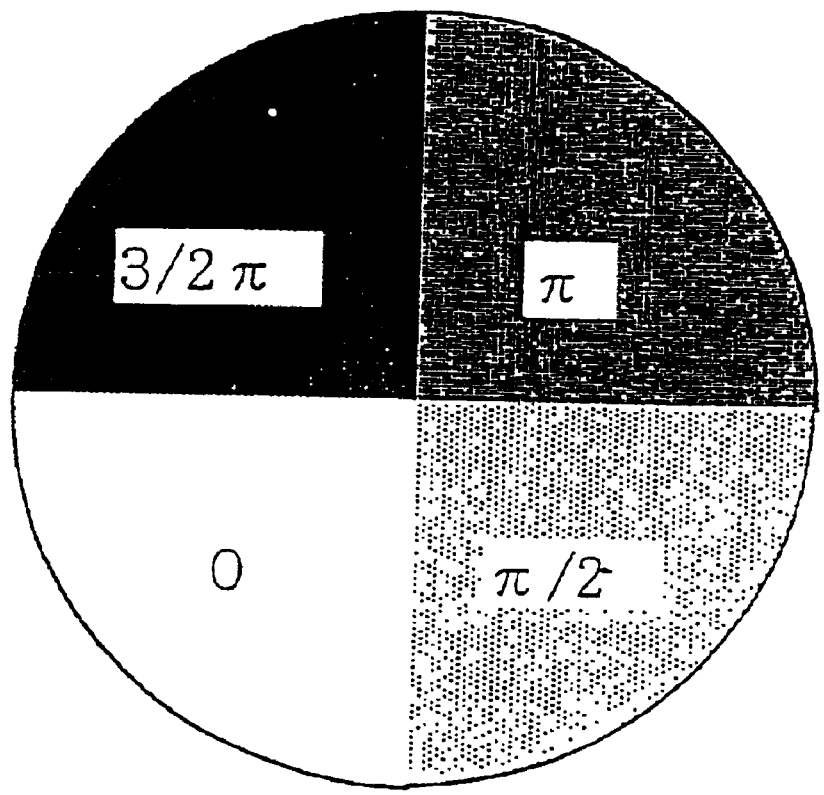
FIG. 38 is a schematic view of a phase plate used to form a hollow beam.

In the present embodiment, a phase plate 36 is placed in the optical path to the dichroic mirror 37 to shape the erase light into a hollow beam. A structure as shown in FIG. 38 can be used as this phase plate 36. The face of the phase plate 1514 as shown in FIG. 38 is equally divided into four regions around the optical axis. These regions are shifted by $\pi/2$ successively. Those points which are symmetrical with respect to the optical axis are shifted in phase by $\pi$. After passing through the phase plate 36, the erase light becomes a hollow beam having a zero intensity in its center. The intensity distribution of this beam is symmetrical with respect to the axis.

The erase light in the hollow beam form is combined with the pump light by the dichroic mirror 37 so as to travel on the same optical axis. This causes the hollow erase light beam to overlap with the pump light, creating fluorescence region $A_0$ and fluorescence-suppressed region $A_1$.

Accordingly, it can be said that the means for causing the regions irradiated with pump light and erase light, respectively, to overlap with each other is the phase plate 36 or a combination of the phase plate 36 and the dichroic mirror 37.

[III/IX.a-2] Sample Observation System

The pump light and erase light created as described above and made coaxial are reflected by a half mirror 38 and focused onto a sample 310 via an objective lens 39 in a sample observation system. As mentioned previously, the sample 3 10 is a biological cell stained with rhodamine 6G. This sample 310 is placed on a three-dimensional motion stage 311 and can move in two dimensions on the focused surface and in one dimension along the optical axis. The 3D motion stage 311 can be driven by an inch worm PZT (piezoelectric device), for example, and can be placed in position at a high positional resolution of the order of nanometers.

[III/IX.a-3] Fluorescence Detection System

The fluorescence detection system is made up of a photomultiplier 314, an eyepiece lens 313, and an IR-cutting filter 312, and is quite simple in structure. Use of a non-resonance two-photon excitation process can quite effectively suppress the phenomenon that pump light and erase light are mixed into the fluorescence signal as background light. To completely remove stray light arising from the pump light and erase light, the IR-cutting filter 312 may be withdrawably inserted in the fluorescence optical path.

This IR-cutting filter 312 may cut off light having a wavelength of 1 μm, for example. Using this filter, stray light originating from the pump light, and erase light can be completely cut off. The fluorescence band of rhodamine 6G is at around 570 nm and spaced widely from the wavelength 500 nm of the original light source. Therefore, even with an inaccurate IR-cutting filter not having very high performance, stray light can be removed sufficiently.

Furthermore, the wavelengths $2\lambda_1$ and $2\lambda_2$ of the pump light and erase light, respectively, do not overlap the fluorescence band and so it is not necessary to remove the wavelength-overlapping fluorescence signal, unlike the prior art double-resonance absorption microscope. Consequently, signals in all the fluorescence bands can be measured without waste. Additionally, a photo multiplier that is cheap and easily available on the market can be used as the detector itself.

For example, in the double-resonance absorption microscope disclosed in Japanese patent application No. 97924/1998, many expensive and accurate optical elements such as a spectroscope and a notch, filter are used to separate excitation light from the fluorescence signal. In addition, cumbersome operations have been required. That is, the spectroscope is combined with an ICCD camera, and the whole fluorescence spectrum is measured. Erase light and pump light are removed on a computer. Moreover, the system of the ICCD camera and the spectroscope is quite expensive. This places a heavy burden on the user.

On the other hand, where a time division measurement method as already described in connection with FIG. 37 is used, if the excitation light is mixed in, it can be completely cut off during measurement of fluorescence. Hence, the S/N can be improved greatly.

As described thus far, the double-resonance absorption microscope in accordance with the present invention is simple in structure but can produce a fluorescence signal with quite high S/N and high signal intensity.

EXAMPLE 5

The depth resolution of the double-resonance absorption microscope in accordance with the invention illustrated in FIG. 36 is described, the depth resolution being taken in the direction of the optical axis.

First, we quantitatively discuss what fluorescence intensity distribution is produced by a non-resonance two-photon excitation process using Eq. (17) above. It is assumed that fluorescence labeler molecules are spatially distributed uniformly in a space. Calculational conditions are listed in Table 1 below.

TABLE 1

| | |
|---|---|
| Numerical aperture of focusing optical system | 0.75 |
| Fluorescence labeler molecules | Rhodamine 6G |
| State of dispersion of fluorescence labeler molecules | Uniform concentration staining |
| Life of fluorescence of fluorescence labeler molecules | 3 [nsec] |
| Absorption cross section $\sigma_{01}$ ($2\lambda_1$) of fluorescence labeler molecules | $10^{-50}$ [cm$^4$ sec/photon] (1064 nm) |
| Absorption cross section $\sigma_{12}$ ($2\lambda_2$) of fluorescence labeler molecules | $10^{-50}$ [cm$^4$ sec/photon] (1197 nm) |
| Wavelength of pump light | 1064 [nm] |
| Wavelength of erase light | 1197 [nm] |
| Pulse width of pump light and erase light | 30 [psec] |
| Interval of pump light and erase light | NO |
| Fluorescence measurement method | Time division measurement method |
| Absorption cross section $\sigma_{01}$ ($\lambda_1$) of one photon in $S_0 \to S_1$ | $4 \times 10^{-16}$ [cm$^{-2}$] (532 nm) |
| Absorption cross section $\sigma_{12}$ ($\lambda_2$) of one photon in $S_1 \to S_2$ | $0.5 \times 10^{-16}$ [cm$^{-2}$] (599 nm) |
| Stimulated emission cross section $\sigma_{21}$ ($\lambda_2$) of one photon in $S_2 \to S_1$ | $0.5 \times 10^{-16}$ [cm$^{-2}$] (599 nm) |

FIG. 39 shows the fluorescence intensity distribution of the fluorescence from a sample by pumping light excitation at the focal plane, taken in the horizontal direction (X-axis direction). FIG. 40 shows the fluorescence intensity distribution plotted against the distance from the origin (or, the focal point) in the Z-axis direction. In these figures, the solid-line curves indicate distributions where a non-resonance two-photon excitations process is used. The broken-line curves indicate distributions where a one-photon excitation process is used. The fluorescence intensity distributions were calculated using Eqs. (18) and (19).

As can be seen from FIGS. 39 and 40, the fluorescence intensity distribution in the case of a one-photon excitation process is more concentrated in the vicinity of the optical axis than in the case of a non-resonance two-photon excitation process, because the excitation wavelength of the pump light is short. On the other hand, the fluorescence intensity distribution in the case of a non-resonance two-photon excitation process is converged more quickly than in the case of a one-photon excitation process. At locations remote from the focal point, the intensity is zero. That is, in the non-resonance two-photon excitation process, excited rhodamine 6G molecules are localized close to the focal point. Fluorescent light is emitted only from certain locations within the 3D space of the sample. This can impart three-dimensional resolution to the double-resonance absorption microscope.

Figure 41:
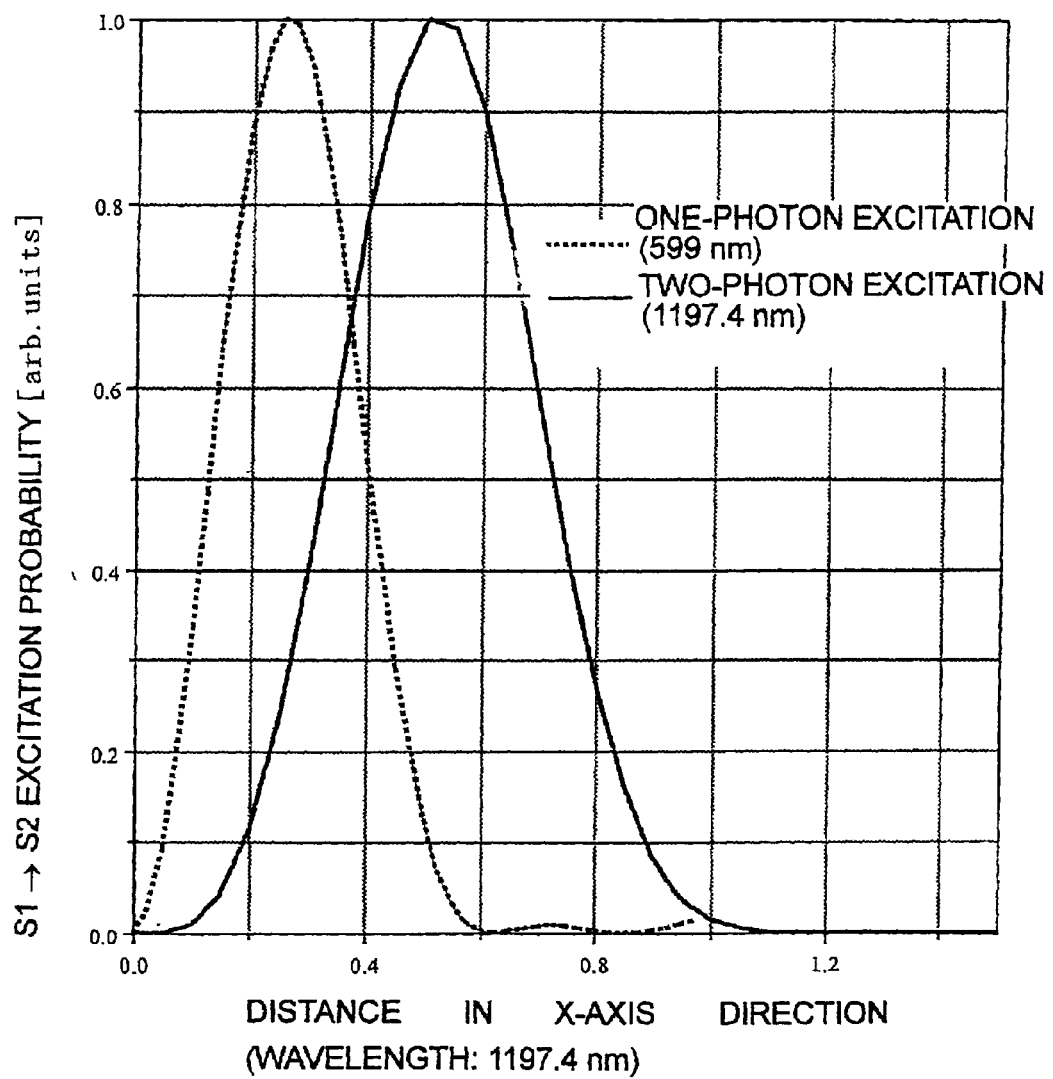
FIG. 41 is a diagram illustrating the probability of excitation $S_1 \rightarrow S_2$ in the X-axis direction within a focal plane where a one-photon excitation process (indicated by the dotted line) and a non-resonance two-photon excitation process (indicated by the solid line) are used.

FIG. 41 shows examples of the probability of excitation $S_1 \to S_2$ at the focal plane caused by the erase light where a one-photon excitation process and a non-resonance two-photon excitation process are used. If the erase light is shaped into a hollow beam and becomes a first-order Bessel Beam, the probability of excitation $S_1 \to S_2$ can be calculated using Eq. (30) below. In Eq. (30), a calculation is made on the assumption that m=1. This probability of excitation $S_1 \to S_2$ is in proportion to the first power of the intensity of the laser light in the case of a one-photon excitation process. The probability is in proportion to the square of the laser light intensity in the case of a two-photon excitation process.

These probabilities obey Eqs. (18) and (19).

$$I(x, y, z) = \int_N \int_A e^{-\frac{z}{2f^2}(\xi^2+\zeta^2)} e^{-im\phi-i\frac{2\pi}{\lambda}(x\xi+y\zeta\eta)} d\xi d\xi \tag{30}$$

Results of calculations indicate that the fluorescence is suppressed according to the spatial distribution shown in FIG. 41. Since it is assumed that the erase light is shaped into a hollow beam, the profile does not affect the depth resolution in the direction of the optical axis, whether the process is a one-photon excitation process or a non-resonance two-photon excitation process. However, the profile taken in the plane perpendicular to the optical axis affects the 2D resolution, because the profile is somewhat more widened in the case of the non-resonance two-photon excitation process and has a wider hollow region.

Then, fluorescence intensity distributions are found when fluorescence is suppressed successfully, using the fluorescence suppression characteristic curve given by Eq. (27) and the beam profiles shown in FIGS. 39, 40, and 41. FIG. 42 shows the fluorescence intensity distribution in the horizontal direction (X-axis direction) within the focal plane near the focal point where a non-resonance two-photon excitation process is used. FIG. 43 shows the fluorescence intensity distribution in the direction of the optical axis (Z-axis direction) within the focal plane near the focal point where a non-resonance two-photon excitation process is used. Eq. (30) was used for calculations. It was assumed that the sample was stained with rhodamine 6G, the erase light had a wavelength of 1197 nm, and the photon flux was $10^{32}$ photons/cm$^2$/sec.

Laser light having a pulse width of 30 psec is assumed. If the light is focused by an achromatic lens with NA=0.75, the specification is roughly equal to 10 $\mu$J/pulse. This light intensity is very weak and has a realistic value that can be sufficiently supplied from a commercially available laser. As can be seen from FIG. 42, the double-resonance absorption microscope built in accordance with the present invention and using a non-resonance two-photon excitation process achieves a fluorescence size of about $\lambda/20$ where the wavelength of 1064 nm of the pump light is taken as a unit. In other words, a spatial resolution of 50 nm can be obtained by making use of infrared radiation. On the other hand, FIG. 43 shows the depth resolution in the direction of the optical axis. A depth resolution of about $4\lambda$ is derived.

FIG. 44 shows spatial resolutions obtained by Fourier-transforming the fluorescence intensity distributions calculated in FIGS. 42 and 43 into a spatial frequency domain. As can be seen from FIG. 44, the present invention provides a depth resolution in the direction of the optical axis, which has not been attained by the prior art double-resonance absorption microscope. This corresponds to the fact that there exist frequency components along $k_{1z}$ that is the optical axis.

It can be understood from the description provided thus far that the double-resonance absorption microscope in accordance with the present invention and shown in FIG. 36 provides a spatial resolution in the vertical direction (depth direction) due to a non-resonance two-photon excitation process, together with super-resolution in the lateral direction due to spatial overlapping of pump light and erase light. Where the phase plate 36 is withdrawably inserted in the optical path of the erase light, if only depth resolution is required in measurements of fluorescence signals, the phase plate 36 may be withdrawn. If 2D resolution is also required, the phase plate 36 may be inserted. In this way, the mode of operation can be switched between these two modes of operation.

EXAMPLE 6

In the double-resonance absorption microscope described previously in connection with FIG. 36, a non-resonance two-photon excitation process is used for both excitation $S_0 \rightarrow S_1$ (pump light) and excitation $S_1 \rightarrow S_2$ (erase light). In the present invention, a non-resonance two-photon excitation process can be used for only one of excitation $S_0 \rightarrow S_1$ and excitation $S_1 \rightarrow S_2$.

Figure 45:
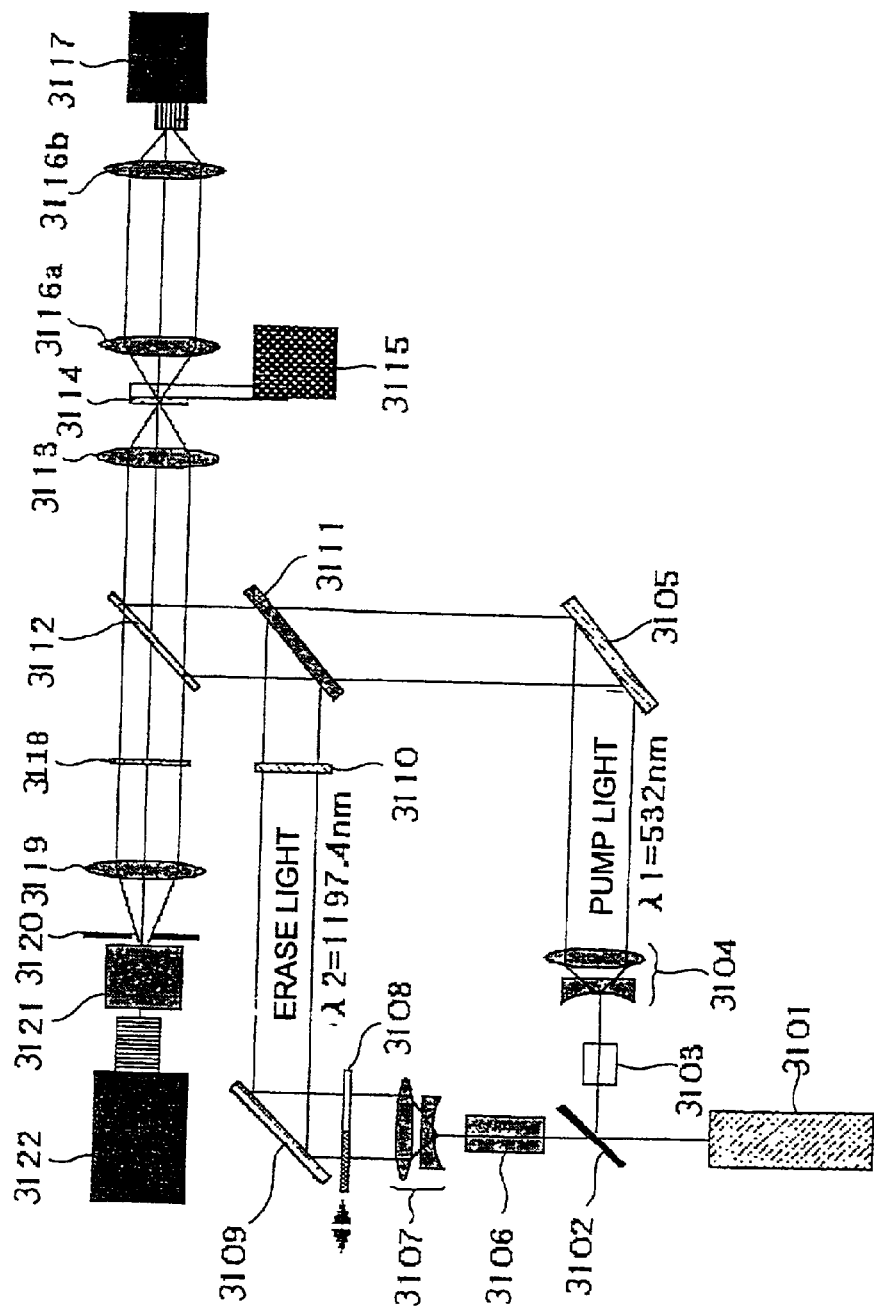
FIG. 45 is a schematic diagram of another double-resonance absorption microscope in accordance with the present invention.

FIG. 45 shows a double-resonance absorption microscope in accordance with the present invention, the microscope being designed so that a one-photon excitation process is used for excitation $S_0 \rightarrow S_1$ and a non-resonance two-photon excitation process is used for excitation $S_1 \rightarrow S_2$. This microscope shown in FIG. 45 constitutes a laser scanning fluorescence microscope similar to the instrument shown in FIG. 36. This microscope can cause the regions irradiated with the pump light and the erase light, respectively, to overlap with each other. A non-resonance two-photon excitation process is used as a non-resonance multiphoton excitation process. A sample 3114 is a biological sample stained with rhodamine 6G and which acts as fluorescence labeler molecules.

Accordingly, the pump light has a photon energy $E_{01}$ of about 2.33 eV and a wavelength $\lambda_1$ of about 532 nm. These are necessary for excitation $S_0 \rightarrow S_1$ in a normal one-photon excitation process. The erase light has a photon energy $E_{12}/2$ of about 1.036 eV and a wavelength $2\lambda_2$ of about 1197 nm. These are necessary for excitation $S_1 \rightarrow S_2$ in a non-resonance two-photon excitation process.

First, pump light due to a one-photon excitation process is created by obtaining the fundamental wave (having a wavelength of 1064 nm and a pulse width of 30 psec) of an Nd:YAG laser 3101, splitting the wave by a half mirror 3102, passing one part of the wave through a KTP crystal 3103 to convert it to its double wave having a wavelength of 532 nm. This pump light is enlarged by a telescope 3104 and passed into a dichroic mirror 3111 acting as a beam combiner by a reflecting mirror 3105.

The other part of the fundamental wave split by the half mirror 3102 passes through a Raman shifter 3106, producing a first-order Stokes line having a wavelength of 1197.4 nm. In this way, erase light due to a non-resonance two-photon excitation process is created. The Raman shifter 3106 is made of a crystal of $Ba(NO_3)_2$ in the same manner as in the case of FIG. 36, and performs a wavelength conversion of incident light on the longer wavelength side (where expressed in terms of photon energy, on the lower energy side) with integral multiples of the resonance wave number 1047 cm$^{-1}$ of the crystal lattice. This erase light is enlarged by the telescope 3107 and then shaped into a hollow beam by a phase plate 3108.

Figure 46:
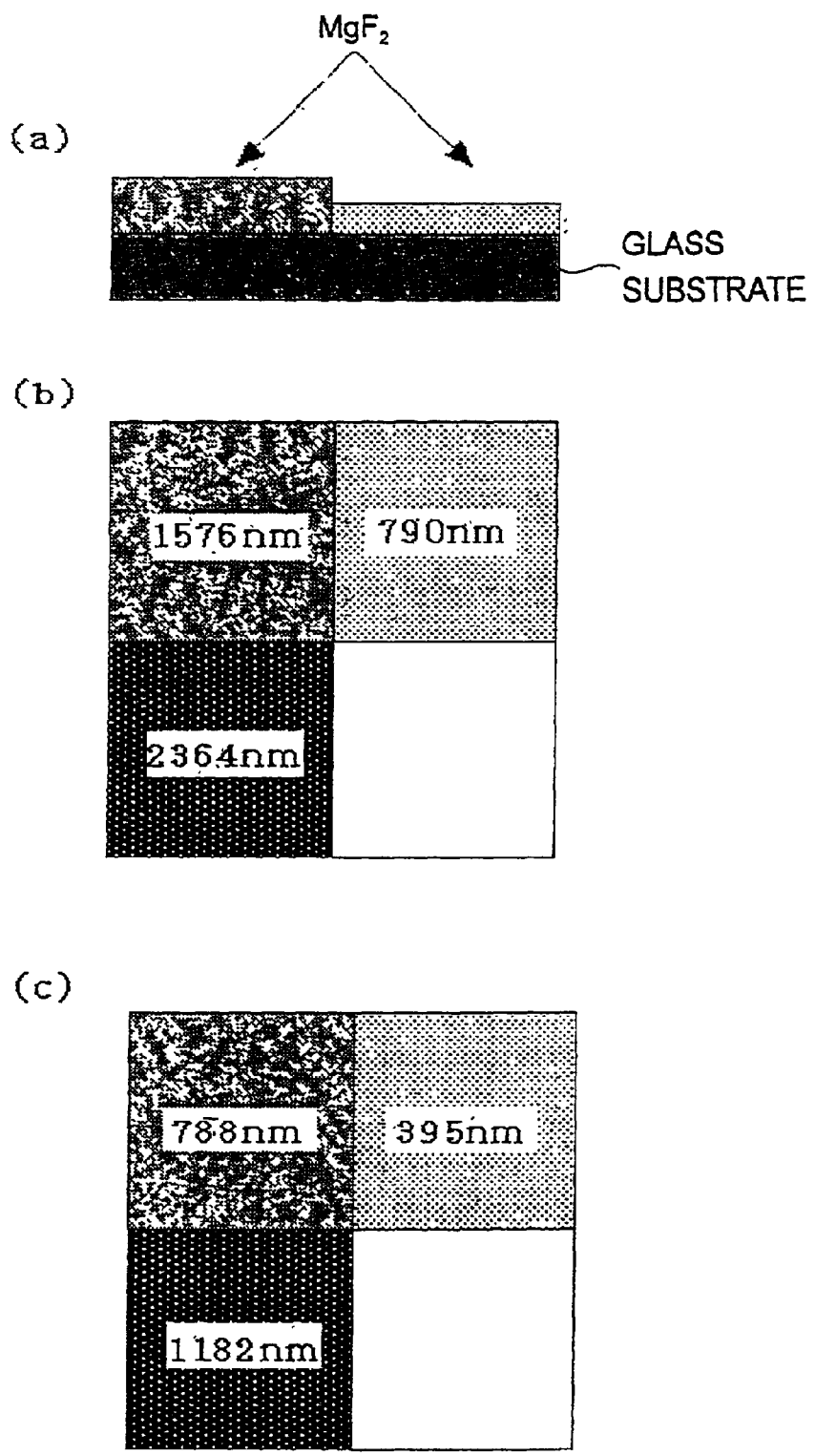
FIG. 46(a) is a schematic cross section of a phase plate.
FIG. 46(b) is a schematic plan view of a phase plate for light of wavelength 1197.4 nm.
FIG. 46(c) is a schematic plan view of a phase plate for light of wavelength 599 nm.

FIG. 46(b) shows one example of the phase plate 3108 for wavelength 1197 nm. A cross section of this phase plate 3108 is shown in FIG. 46(a). A face of a glass substrate is divided into four regions on which magnesium fluoride is deposited. These regions have different film thicknesses of magnesium fluoride such that erase light beams passing through positions symmetrical with respect to the optical axis are shifted in phase by r for wavelength of 1197 nm. As a result, erase light having an ideal hollow beam profile exhibiting zero intensity on the optical axis can be created. Preferably, the phase plate 3108 can be detachably inserted. Also, the erase light can be optionally shaped into a hollow beam. In the description given here, it is assumed that the erase light is shaped into a hollow beam to impart super-resolution in the lateral direction and that the hollow erase light beam is made to overlap one part of the pump light.

The erase light shaped into a hollow beam is directed into a dichroic mirror 3111 by a reflecting mirror 3109. A notch filter 3110 is inserted in the optical path between the reflecting mirror 3109 and the dichroic mirror 3111. As the erase light passes through this notch filter 3110, light of wavelength of 1064 nm that is the fundamental wave of the Nd:YAG laser 3101 not converted by the Raman shifter 3106 is cut off. Consequently, only erase light having a wavelength of 1197 nm is extracted.

Then, the pump light having a photon energy $E_{01}$ of about 2.33 eV and a wavelength $\lambda_1$ of about 532 nm and the erase light having a photon energy $E_{12}/2$ of about 1.036 eV and a wavelength $2\lambda_2$ of about 1197 nm are made coaxial by the dichroic mirror 3111 and guided into the sample observation optical system.

In FIG. 45, the KTP crystal 3103 is placed on the half mirror 3102 on the side of the optical path of the pump light. The erase light can also be created if the crystal is located on the incident side of the half mirror 3102. In particular, some of the fundamental wave passed through the KTP crystal 3103 is not converted into its double wave. If the laser intensity is sufficient, the fundamental wave not converted enters the Raman shifter 3106. In consequence, erase light having an intensity sufficient to induce excitation $S_1 \rightarrow S_2$ can be created.

The pump light and the hollow erase light that are made coaxial are brought onto the optical axis by the half mirror 112 and focused onto the sample surface by the objective lens 113.

In the present embodiment, an observational microscope optical system is also mounted behind the sample 3114. Light transmitted through the sample 3114 is observed by a CCD camera 3119 via lenses 3116a, 3116b for the transmitted light.

On the other hand, fluorescence emitted from the sample surface passes through the objective lens 3113 and the half mirror 3112. This notch filter 3118 cuts the stray light from the pump light having a wavelength $\lambda_1$ of about 532 nm. Since the erase light has a wavelength of $2\lambda_2$ and is not mixed into the fluorescence signal, it is not necessary to remove the fluorescence signal using a notch filter or the like.

The fluorescent light from which the stray light from the pump light has been removed is focused onto the diameter of a pinhole 3120 by a focusing lens 3119, the pinhole being located at a confocal position. The light then passes through a pinhole 3123 and is separated according to wavelength by a spectroscope 3121. Subsequently, the fluorescence spectrum is directly taken by an ICCD camera 3122.

The fluorescence signal has excellent 2D resolution due to overlapping irradiation of the pump light and the hollow erase beamlight. In addition, the non-resonance two-photon excitation process regarding the erase light gives excellent depth resolution. Of course, neither pump light nor the erase light is mixed as background light into the fluorescence signal and, therefore, the S/N is quite high.

This fluorescence signal can be converted into a 3D image using a computer (not shown), for example, in the manner described below.

A three-dimensional motion stage 3115 on which a sample is carried is scanned in two dimensions within a plane perpendicular to the optical axes of the pump light and erase light. At the same time, the stage is moved linearly in the direction of the optical axis. The fluorescence signal from each scan point is supplied into the computer from the ICCD camera 3122. A three-dimensional fluorescence image of the sample 3114 is obtained by imaging data about each-fluorescence signal by computer graphics. In particular, the computer drives a controller (not shown) for an Nd:YAG laser 3101 acting as a fundamental light source to control the timing of laser oscillation. At the same time, the computer controls the three-dimensional motion stage 3115 to scan the sample 3114 in synchronism with the timing of the laser oscillation. Similarly, data about fluorescence spectral signals from the sample 3114 is supplied from the ICCD camera 3122 in synchronism with the timing of the laser oscillation.

Since the pulse width of 30 psec of the pump light and erase light is much shorter than the life 3 nsec of the fluorescence from rhodamine 6G, the gating of the measurement time of the ICCD camera 3122 and the optical path length of the Nd:YAG laser 3101 can be adjusted by making use of the aforementioned time division measurement method. Using the timing illustrated in FIG. 37, $t_p$ is the pulse width 30 psec of the pump light, $t_e$ is the pulse width 30 psec of the erase light, and $t_g$ is the pulse width of a gating pulse for measurement of the ICCD camera 3122. Consequently, if a trace amount of pump light or erase light should be mixed into the fluorescence signal, it can be prevented from being introduced into the ICCD camera 3122 during fluorescence measurement. This can improve the S/N further.

Where this time division measurement method is used, the structure may be simplified by removing the notch filter 3118. Of course, where emphasis is placed on the S/N rather than on the optical system configuration, the time division measurement method can also be used without removing the notch filter 3118.

The example of FIG. 45 is based on a mechanical scan of the three-dimensional motion stage 3115. Of course, the laser beam itself can be scanned using a galvano mirror for swinging the half mirror 3111.

The double-resonance absorption microscope in accordance with the present embodiment described thus far is designed so that a one-photon excitation process is used for excitation $S_0 \rightarrow S_1$ and a non-resonance two-photon excitation process is used for excitation $S_1 \rightarrow S_2$. Conversely, advantages similar to those described above can be accomplished using a structure where a non-resonance two-photon excitation process and a one-photon excitation process are used for excitation $S_0 \rightarrow S_1$ and excitation $S_1 \rightarrow S_2$, respectively. In this case, with respect to the pump light, the KTP crystal 3103 in the optical path of the pump light is removed. The fundamental wave 1064 nm (=$2\lambda_1$) of the Nd:YAG laser 3101 is used as pump light intact. With respect to the erase light, the KTP crystal 3103 is inserted in the optical path of the erase light on the incident side of the Raman shifter 3106. The fundamental wave 1064 nm is converted into its double wave 532 nm by the KTP crystal 3103. The second-order Stokes line having a wavelength of 599 nm (=$\lambda_2$) is produced from the double wave 532 nm by the Raman shifter 3106. This line is used as the erase light. A phase plate as shown in FIG. 46(c) and corresponding to wavelength 599 nm is used as the phase plate 3108. The erase light of 599 nm becomes an ideal hollow beam. A notch filter capable of cutting stray light from the erase light of 599 nm is used as the notch filter 3118.

It is to be noted that the present invention is not limited to the embodiments described thus far. Rather, various changes and modifications are possible. For example, in the embodiments described thus far, a sample is stained with rhodamine 6G as a typical example of fluorescence labeler molecules. Similar advantages, i.e., improved S/N and 3D spatial resolution, can be attained by using other fluorescence labeler molecules. Pump light having the required photon energy and the required wavelength and erase light having the required photon energy and the required wavelength may be generated using wavelength-variable OPA, OPO, or OPG laser system utilizing nonlinear electrooptical effects according to the fluorescence labeler molecules.

As described in detail thus far, the present invention can offer a novel double-resonance absorption microscope which is capable of suppressing deterioration of S/N due to mixing of excitation light into the fluorescence signal and which has excellent three-dimensional spatial resolution.

[IX.b] Another Novel Double-Resonance-Absorption Microscope Having a Superb Three-dimensional Space Resolution In order to achieve a three-dimensional spatial resolution, a double-resonance-absorption microscope in accordance with the invention of the present application comprises at least a light source for a pump light of a wavelength $\lambda_1$ which excites a sample molecule to a first electronic excited state of a singlet state from a ground state, either or both of a light source for a probe light of a wavelength $\lambda_2$ which excites the sample molecule to a second electronic excited state or a higher excited state of a singlet state from the first electronic excited state, and a light source for a probe light of a wavelength $\lambda_3$ which excites the sample molecule, transited to a triplet level lower in energy than the first electronic excited state from the first electronic excited state, to a higher excited triplet level from the triplet level. An overlap component is provided for overlapping a part or all of the irradiating areas of the pump light and the probe light with each other. A sample is irradiated with the pump light and the probe light through the overlap component, and a transient Raman scattering light emitted from the irradiating areas of both lights is detected by using a double-resonance absorption process for the pump light and the probe light and a transient Raman scattering process in combination.

An ordinary transient Raman scattering light in a transition from a second electronic excited state of a singlet state and a transient Raman scattering light in a transition from an excited triplet level via a triplet level are available as transient Raman scattering lights to be detected and observed by this double-resonance-absorption microscope. The former is called a singlet transient Raman scattering light and the latter is called a triplet transient Raman scattering light to facilitate explanation. Each case will be described below. Furthermore, the probe light of the wavelength $\lambda_2$ in the case of detecting the singlet transient Raman scattering light is called a singlet probe light, and the probe light of the wavelength $\lambda_3$ in the case of detecting the triplet transient Raman scattering light is called a triplet probe light.

[IX.b-1] Singlet Transient Raman Scattering Light

Figure 47:
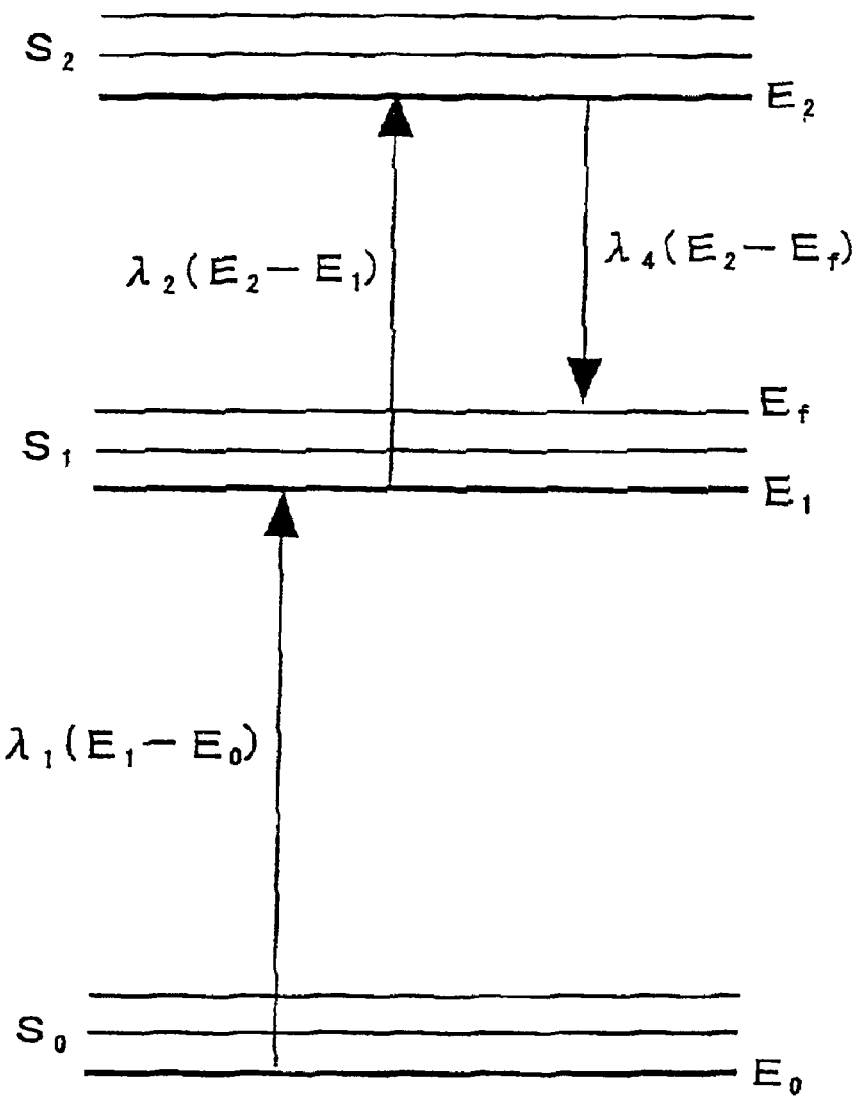
FIG. 47 is a conceptual diagram illustrating singlet transient Raman scattering light.

FIG. 47 is a conceptual view illustrating a singlet transient Raman scattering light. First, as shown in FIG. 47, a sample molecule in a ground state $S_0$ (=energy $E_0$) is excited to a first electronic excited state $S_1$ (=energy $E_1$) by a light (hereinafter called a pump light) of a wavelength $\lambda_1$ (=a wavelength corresponding to photon energy $E_1-E_0$). The sample molecule in the $S_1$ state is then excited to a second electronic excited state $S_2$ (=energy $E_2$) by a singlet probe light of a wavelength $\lambda_2$ (=a wavelength corresponding to photon energy $E_2-E_1$; a wavelength corresponding to energy $E_1$ in the case when the sample molecule is excited to an electronic excited state higher than the second electronic excited state) within the lifetime of the $S_1$ state. The electronic excited state $S_2$ includes the so-called imaginary quantum state that is not usually present, but is present instantaneously only when a strong laser electric field is applied to the molecule. The spin multiplicity of the $S_1$ and $S_2$ states is usually I, and the $S_1$ and $S_2$ states are classified as a singlet state in spectroscopy. In this case, photons having photon energy corresponding to the difference in energy ($E_2 \to E_f$=wavelength $\lambda_4$) between the energy level of the $S_2$ state and the high-order vibrational level $E_f$ of the $S_1$ state are scattered from the sample molecule in the $S_2$ state. A light scattered in this process is called a transient Raman scattering light. This process can be called a kind of resonance Raman scattering process, and the sectional area of the scattering light is very large.

When this transient Raman scattering light is detected, fluorescence making a transition from the $S_2$ state to the $S_1$ state, serving as a background signal, is very unlikely generated. A resonance Raman light from the transient state is observed in a waveband to which attention is paid. In other words, only the transient Raman scattering light is observed. In addition, when the sample molecule in the ground state is excited to the $S_1$ state by the pump light, intense fluorescence emits from the $S_1$ state in the case of a usual sample molecule. However, since the wave range of the fluorescence is far shorter than the wave band wherein the transient Raman scattering light is observed, it is possible to separate and extract only the transient Raman scattering light by using a simple sharp-cut filter. Furthermore, because of the double-resonance absorption process by irradiation of the two wavelength lights (the pump light and the singlet probe light), the transient Raman scattering light is limited by the two wavelength lights. As a result, the chemical composition of the sample can be identified accurately. Moreover, in the transient Raman scattering process, only the light having a specific electric-field vector with respect to a molecular axis responds intensively. For this reason, when the transient Raman scattering light is measured while the polarization directions of the pump light and the singlet probe light are determined, it is possible to identify the orientation direction of the molecule.

[IX.b-2] Triplet Transient Raman Scattering Light

Figure 48:
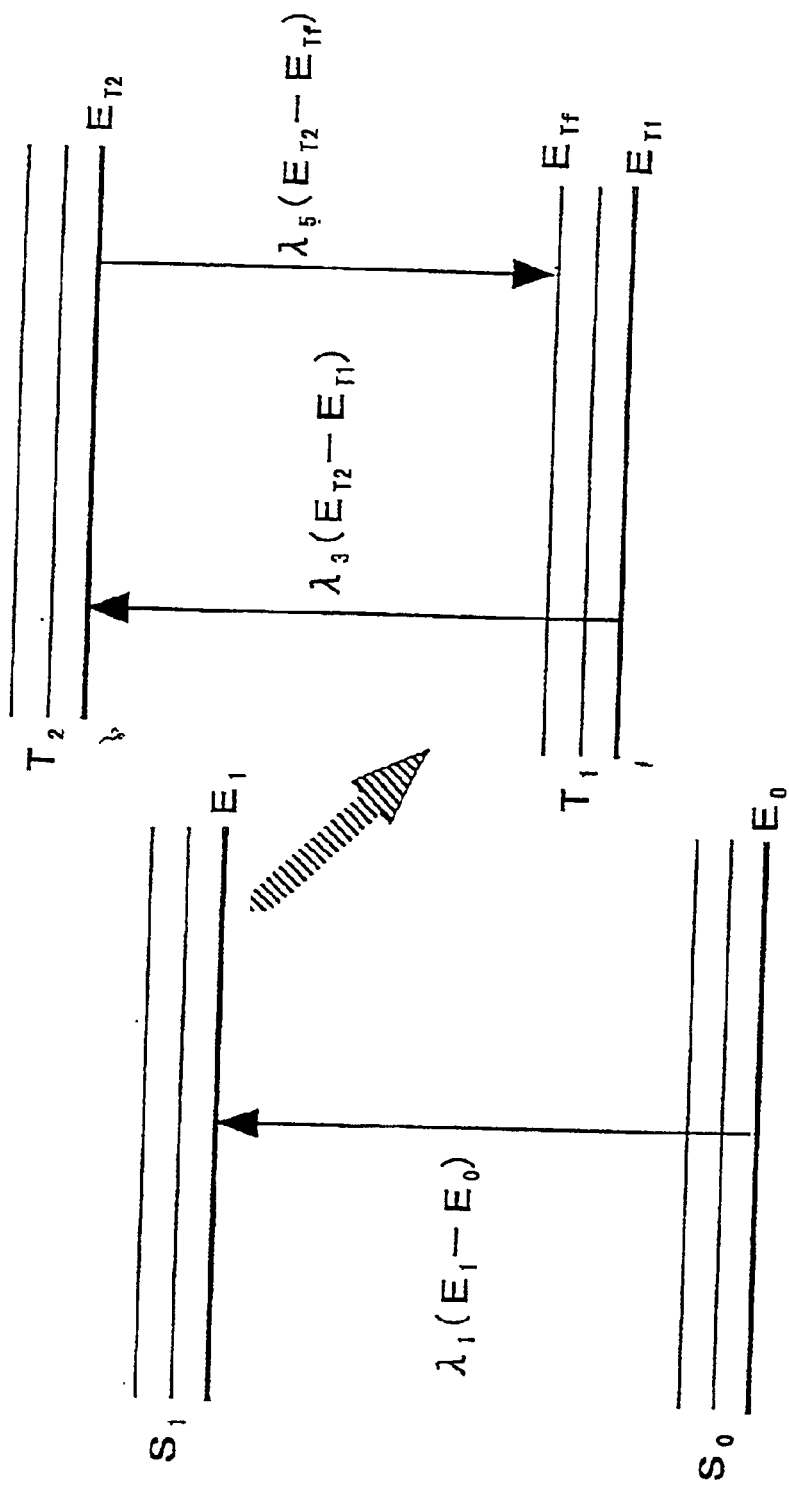
FIG. 48 is a conceptual diagram illustrating triplet transient Raman scattering light.

Next, the double-resonance-absorption microscope of the present invention can detect even a transient Raman scattering light based on a triplet level having energy lower than that of the first electronic excited state of the singlet state. FIG. 48 is a conceptual view illustrating the triplet transient Raman scattering light.

When a sample molecule in the ground state $S_0$ is excited to the $S_1$ state by a pump light of a wavelength $\lambda_1$, the excited sample molecule deexcites to the ground state in a fluorescence process. On the other hand, the excited sample molecule also makes a transition to the triplet level $T_1$ (=energy $E_{T1}$) having energy lower than that in the singlet first electronic excited state $S_1$ at a high probability as shown in FIG. 48. This triplet level $T_1$ has a spin multiplicity different from that in the ground state $S_0$, and optical transition is inhibited, thereby becoming the so-called spin forbidden transition. For this reason, the lifetime of the triplet level $T_1$ is very long, that is, a lifetime on the order of $\mu$ seconds in many cases. In addition, the probability of the fluorescence process from the triplet level $T_2$ (=energy $E_{T2}$ higher than the triplet level $T_1$ in energy is very low. By using this, the sample molecule in the ground state $S_0$ is excited to the $S_1$ state by the irradiation of the pump light. After a fluorescence emission process (for example, after several nseconds, depending on the sample molecule), by the irradiation of a triplet probe light of a wavelength of $\lambda_3$ corresponding to the difference in energy ($E_{T2}-E_{T1}$) between the triplet level $T_1$ and the triplet level $T_2$ (hereinafter called an excited triplet level) higher than the triplet level $T_1$, the sample molecule having made a transition to the triplet level $T_1$ is exited to the excited triplet level $T_2$. This generates a transient Raman scattering light of a wavelength $\lambda_5$ (=a wavelength corresponding to $E_{T2}-E_{Tf}$), making a transition from a specific vibrational level of the excited triplet level $T_2$ to the higher vibrational level $E_{Tf}$ of the triplet level $T_1$. Since no fluorescence is generated from the excited triplet level $T_2$, the transient Raman scattering light can be detected and observed at a very high S/N ratio.

[IX.b-3] Plane Resolution and Three-Dimension Resolution by Detection of Transient Raman Scattering Light The above-mentioned transient Raman scattering light (lights in the singlet and triplet states are generally identified in this way to simplify explanation) is generated from only an area of a sample wherein the pump light of the wavelength $\lambda_1$ and the singlet probe light of the wavelength $\lambda_2$ or the triplet probe light of the wavelength $\lambda_3$ are overlapped spatially with each other. For example, as shown in FIG. 49, when the pump light and the probe light (light in the singlet and triplet states are generally identified in this way to simplify explanation) are condensed at a diffraction limit, the overlapping irradiating areas of both light beams are substantially limited to one condensed spot area. The observation resolution thus obtained can be made higher than the diffraction limits of the emitted lights. FIG. 49 shows the beam profiles of the pump light and the probe light condensed on the face of the sample. In the figure, $0.61 \times \lambda_1/NA$ and $0.61 \times \lambda_2/NA$ are the condensing radii of the pump light and the probe light on the basis of Rayleigh's limit and correspond to the diffraction limits.

Hence, by the irradiation of the pump light and the probe light overlapped with each other and by narrowing the overlapped area, the detection of a transient Raman scattering light by using the double-resonance absorption process can be achieved at an excellent plane resolution higher than the diffraction limits of beams. An area wherein a transient Raman scattering light is generated in this way is herein called a Raman active area. In the conventional double-resonance-absorption microscope for detecting fluorescence, the area (fluorescence area $A_0$) wherein the light beams of two wavelengths are not overlapped with each other is a fluorescence emission area, i.e., an observation area, as shown in the above-mentioned FIG. 6. In the double-resonance-absorption microscope in accordance with the invention of the present application, however, the overlapping area of the pump light and the probe light is a Raman active area, i.e., an observation area.

When explained more quantitatively, since the transient Raman scattering light is generated from the Raman active area limited by the pump light and the probe light, the Raman active area is localized on the optical axis. For example, as shown in FIG. 50, the pump light of the wavelength $\lambda_1$ and the probe light of the wavelength $\lambda_2$ (explanation is given in the case of the wavelength $\lambda_2$ to simplify explanation although the same explanation is applicable to the case of the wavelength $\lambda_3$) are combined coaxially by a half mirror and condensed on the face of the sample by an aplanatic lens with a numerical aperture NA. In this case, according to an image formation theory using wave optics, the energy intensity profiles on the x-y focal surfaces of the pump light and the probe light condensed on the face of the sample are given by the following Eq. 31 and Eq. 32, respectively.

$$I_{\lambda 1}(x, y) = \left[\frac{2E_{\lambda 1}J_1(2\pi\xi_1)}{2\pi\xi_1}\right]^2 \quad \text{(Eq.31)}$$

$$\xi_1 = \frac{NA}{\lambda_1}\sqrt{x^2 + y^2}$$

$$I_{\lambda 2}(x, y) = \left[\frac{2E_{\lambda 2}J_1(2\pi\xi_2)}{2\pi\xi_2}\right]^2 \quad \text{(Eq.32)}$$

$$\xi_2 = \frac{NA}{\lambda_2}\sqrt{x^2 + y^2}$$

where $J_1(2\pi\xi_1)$ and $J_1(2\pi\xi_2)$ designate linear Bessel functions, and $E_{\lambda 1}$ and $E_{\lambda 2}$ designate the intensities of the electric fields of the pump light and the probe light.

Generally, when the intensity $I^{\lambda,1}$, (x, y) of the pump light is low, the number of molecules $n_1$ to be excited from the ground state $S_0$ to the $S_1$ state is proportional to $I_{\lambda 1}$, (x, y). On the other hand, the intensity of the transient Raman scattering light is also proportional to $I_{\lambda 2}$ (x, y) of the probe light. As a result, the intensity $I_{signal}$ (x, y) of the scattering light generated in the transient Raman scattering process is expressed as follows by using a certain constant of proportion C.

$$I_{signal}(x, y) = C\left[\frac{J_1\left(2\pi\frac{NA}{\lambda_1}\sqrt{x^2+y^2}\right)}{\sqrt{x^2+y^2}} \cdot \frac{J_1\left(2\pi\frac{NA}{\lambda_2}\sqrt{x^2+y^2}\right)}{\sqrt{x^2+y^2}}\right]^2 \quad \text{(Eq.33)}$$

As being obvious from Eq. 33, the Raman active area on the surface of the sample is limited to an area wherein the number of molecules is proportional to the second power of the linear Bessel function and inversely proportional to the fourth power of r; $r=(x^2+y^2)^{1/2}$ and is the distance from the intersection of the focal plane and the optical axis. In accordance with the conventional and known fluorescence microscope and the Raman spectroscopy method, a signal light emitting area is determined by the diffraction limit equation Eq. 31 for the pump light. When the equation Eq. 33 is compared with the equation Eq. 31, the signal light emitting area in Eq. 33 is obviously narrower. This indicates that the sample can be observed at a plane resolution exceeding the diffraction limit. It is thus possible to achieve a super-resolution even in the case of detecting a transient Raman scattering light.

FIG. 51 shows the standardized profiles of the intensity $I_{\lambda 1}$, (x, y) of the pump light, the intensity $I_{\lambda 2}$ (x, y) of the probe light and the intensity $I_{signal}$ (x, y) of the transient Raman scattering light. Referring to FIG. 51, it is also found that the profile of the intensity $I_{signal}$ (x, y) of the transient Raman scattering light around the optical axis is narrower than the profile of the $I_{\lambda 1}$ (x, y) of the pump light and the profile of the intensity $I_{\lambda 2}$ (x, y) of the probe light. It is thus possible to confirm that a plane resolution at a super-resolution level has been achieved by the transient Raman scattering process.

Furthermore, the double-resonance-absorption microscope in accordance with the invention of the present application, which is intended to detect a transient Raman scattering light, can also achieve a resolution in the direction of the optical axis, i.e., a three-dimensional resolution. For example, as described clearly in "O puls E, No. 213, p107–116, by Kunio Tsuruta," when the number of molecules being proportional to the second power of the linear Bessel function and inversely proportional to the fourth power of r are present just as with the intensity distribution $I_{signal}$ (x, y) of the light-responding area expressed by Eq. 33, a light-responding area is also localized in the direction of the optical axis, thereby having a vertical resolution, i.e., a three-dimensional spatial resolution. In reality, Eq. 33 has the same type of function as that of the point image intensity distribution function of a cofocal laser-scanning microscope with a pinhole in the front face of its device for receiving a detected light (see O puls E, No. 213, p107–116, by Kunio Tsuruta). The equation thus indicates quantitatively that a light-responding area in the sample is also localized in the direction of the optical axis.

When the wave optics theory is used on the assumption that the number of molecules excited from the ground state $S_0$ to the $S_1$ state is proportional to the intensity of the pump light and that the intensity of the transient Raman scattering light is also proportional to the intensity of the probe light, the light-responding area can be calculated three-dimensionally as described below.

First, when a laser beam of a wavelength of $\lambda$ is condensed by an aplanatic lens with a numerical aperture NA, a micro-beam having a three-dimensional electric field distribution function f(x, y, z) given by the following Eq. 34 is formed at the focus.

$$f(x, y, z) = \int\int_{NA} e^{\frac{z}{2f^2}(\xi^2+\zeta^2)} e^{-i\frac{2\pi}{\lambda}(x\xi+y\zeta\eta)} d\xi d\zeta \quad \text{(Eq.34)}$$

where ($\xi$, $\zeta$) represent the coordinates of a pupil face, and f represents a focal length. Hence, the intensity profiles of the pump light of the wavelength $\lambda_1$ and the probe light of the wavelength $\lambda_2$ are given by the following Eq. 35 and Eq. 36, respectively.

$$I_{\lambda 1}(x, y, z) = \left[\int\int_{NA} e^{\frac{z}{2f^2}(\xi^2+\zeta^2)} e^{-i\frac{2\pi}{\lambda_1}(x\xi+y\zeta\eta)} d\xi d\zeta\right]^2 \quad \text{(Eq.35)}$$

$$I_{\lambda 2}(x, y, z) = \left[\int\int_{NA} e^{\frac{z}{2f^2}(\xi^2+\zeta^2)} e^{-i\frac{2\pi}{\lambda_2}(x\xi+y\zeta\eta)} d\xi d\zeta\right]^2 \quad \text{(Eq.36)}$$

By using the fact that the number of the molecules to be excited from the ground state $S_0$ to the $S_1$ state is proportional to the intensity of the pump light and that intensity of the Raman scattering light is also proportional to the intensity of the probe light, the three-dimensional intensity $I_{signal}$ (x, y, z) of the scattering light generated in the transient Raman scattering process is expressed as follows by using a certain constant of proportion C.

$$I_{signal}(x, y, z) = C\left[\int\int_{NA} e^{\frac{z}{2f^2}(\xi^2+\zeta^2)} e^{-i\frac{2\pi}{\lambda_1}(x\xi+y\zeta\eta)} d\xi d\zeta\right]^2 \cdot \left[\int\int_{NA} e^{\frac{z}{2f^2}(\xi^2+\zeta^2)} e^{-i\frac{2\pi}{\lambda_2}(x\xi+y\zeta\eta)} d\xi d\zeta\right]^2 \quad \text{(Eq.37)}$$

When the calculated $I_{signal}$ (X, Y, Z) is Fourier-transformed in a frequency space, a three-dimensional OTF: $S_{signal}$ ($k_x$, $k_y$, $k_z$), which is a physical quantity given by the following equation and being observable in reality, is obtained.

$$S_{signal}(k_x, k_y, k_z) = \int\int\int I_{signal}(x, y, z) e^{-(xk_x+yk_y+zk_z)} dxdydz \quad \text{(Eq.38)}$$

Furthermore, when Eq. 35 is Fourier-transformed in a similar way, a three-dimensional OTF: $S_{usual}$ ($k_x$, $k_y$, $k_z$) for a usual fluorescence microscope, given by the following equation, is obtained.

$$S_{usual}(k_x, k_y, k_z) = \int\int\int I_{\lambda 1}(x, y, z)e^{-(xk_x+yk_y+zk_z)}dxdydz \quad (Eq.39)$$

where $k_x$, $k_y$ and $k_z$ are wave vector components for the excited light of the wavelength $\lambda_1$. Assuming that the pupil face is symmetrical with respect to the optical axis, when a parameter of $r=(x^2+y^2)^{1/2}$ introduced, and when the space distribution section of $(k1_r, k1_z)$ in the case of a usual single photon excitation process and the space distribution section of $(k2_r, k2_z)$ in the case of a transient Raman scattering process are calculated by using Eq. 38 and Eq. 39, the space distribution sections are obtained as shown in FIGS. 52A and 52B, for example. FIGS. 52A and 52B show resolutions in the cases of the single photon excitation process and the transient Raman scattering process, respectively. In FIGS. 52A and 52B, $k1_r$ and $k2_r$ are wave vector components in the radial direction from the optical axis.

Referring to FIGS. 52A and 52B, the upper limit $k_{max}$ and the lower limit $k_{min}$ of the space frequency band in the radial direction are expressed as follows by using the numerical aperture NA of the optical system in both cases of the usual single photon excitation process and the transient Raman scattering process.

$$K_{max} = -K_{min} = 2\frac{NA}{\lambda_1} \quad (Eq.40)$$

This indicates that the upper and lower limits of the spatial resolution in the transverse direction have an identical value. However, a significant difference is found in the resolution in the direction of the optical axis. In other words, in the usual single photon excitation process, no value is present in the $k1_z$ axis direction including the origin, and no resolution is present at all in the direction of the optical axis. On the other hand, in the transient Raman scattering process, a value is present as expressed below even in the direction of the optical axis $k2_z$.

$$K_{max} = -K_{min} = \frac{\left(1-(1-NA^2)^{\frac{1}{2}}\right)}{\lambda_1} \quad (Eq.41)$$

It is thus found that a resolution in the so-called depth direction is present. When examined physically, this corresponds to the fact that the optically active area in the transient Raman scattering process is localized in a very narrow spatial area indicated in Eq. 37. As a result, in the as double-resonance-absorption microscope in accordance with the invention of the present application, it is possible to achieve an excellent three-dimensional spatial resolution by using the transient Raman scattering process.

[IX.b-4] Sample Analysis

Furthermore, in the invention of the present application, a transient Raman scattering light is measured while changing the intervals of the time of the irradiation of the pump light and the probe light to a sample, and while changing the polarization states, wavelengths or intensities of both the lights, independently of one another. By this measurement, it is possible to obtain detailed information regarding the sample, such as the chemical change of a specific molecule in the sample with the passage of time and the structural change of the specific molecule due to irradiation with the pump light.

As described above, in the double-resonance-absorption microscope in accordance with the present invention, by using the double-resonance absorption process and the transient Raman scattering process in combination, the plane resolution in the transverse direction and the resolution in the depth direction of the optical axis direction can have super-resolutions exceeding the diffraction limit of the emitted light, and detailed sample analysis is also made possible.

EXAMPLE 7

Figure 53:
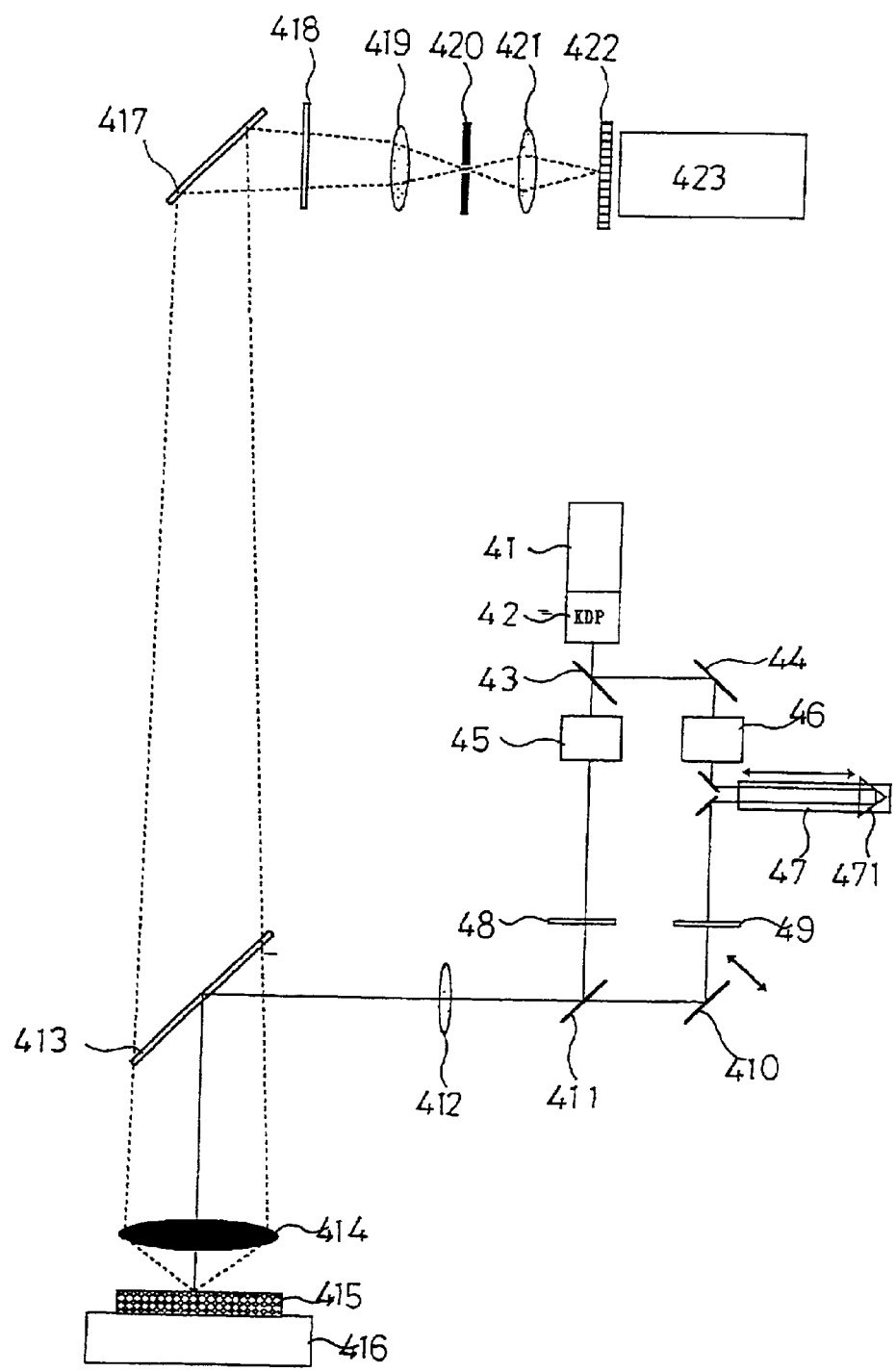
FIG. 53 is a schematic diagram of a double-resonance-absorption microscope in accordance with the present invention.

FIG. 53 is a schematic view showing an embodiment of the double-resonance-absorption microscope in accordance with the invention of the present application.

In this embodiment, a picosecond Nd:YAG laser 41 is provided as a basic light source. By changing the wavelength of its basic wave using a KDP crystal 42, higher harmonics, such as 532 nm, 355 nm, 266 nm, etc. are generated by oscillation. By using an optical parametric generator 45, these light beams are converted so as to have a wavelength $\lambda_1$ wherein a sample molecule to be observed can be excited from $S_0$ to $S_1$, and the light thus obtained is used as a pump light.

Furthermore, a part of the double harmonic is taken out via a half mirror 43, and enters another optical parametric generator 46 via a half mirror 44. The light is then converted so as to have a wavelength $\lambda_2$, wherein the sample molecule can be excited from $S_1$ to $S_2$, or a wavelength $\lambda_3$, wherein the sample molecule can be excited from T1 to T2. The light thus obtained is used as a singlet probe light or a triplet probe light. The probe light is optically delayed by a delay optical system 47 to obtain an appropriate time difference between the probe light and the pulse pump light. The time difference can be controlled easily by the parallel translation of a prism 471 mounted on the delay optical system 47. More specifically, by the optical delay due to the optical path control of the delay optical system 47 serving as an irradiation time control means, the singlet probe light of the wavelength $\lambda_2$ is emitted to reach the face of the sample before the sample molecule makes a transition from the first electronic excited state $S_1$ of the singlet state to the triplet level $T_1$ after the irradiation of the pump light. On the other hand, after the irradiation of the pump light, the triplet probe light of the wavelength $\lambda_3$ is emitted to reach the face of the sample after the sample molecule makes a transition from the first electronic excited state $S_1$ of the singlet state to the triplet level $T_1$.

The probe light, the irradiation time of which is controlled as described above, enters a dichroic mirror 411 via a polarizer 49 and a swaying mirror 410 on its optical path. The pump light enters the dichroic mirror 411 via a polarizer 48 on its optical path. Both of the light beams take the same optical path by virtue of the dichroic mirror 411. The polarizers 48 and 49 serving as polarized state changing means can freely rotate around the polarization planes of the pump light and the probe light.

Furthermore, by controlling the optical path of the probe light with respect to the pump light by using the swaying mirror 410 serving as an overlap means, the irradiating areas of the light beams can be overlapped partially with each other on the condensing plane as shown in the above-mentioned FIG. 49. The irradiating areas of the lights may be overlapped entirely as a matter of course. However, in order to have a higher plane resolution as described above, it is desired that the irradiating areas should be overlapped partially and that the overlapped area should be made smaller.

The pump light and the probe light, the irradiating areas and time periods of which are controlled as described above, are formed by a relay lens 412, enter a half mirror 413, pass through an objective lens 414, and condense on a sample 415. The sample 415 is mounted on a sample scanning stage 416.

When the singlet probe light is emitted after the irradiation of the pump light as described above, a singlet transient Raman scattering light is generated from the sample 415. When the triplet probe light is emitted, a triplet transient Raman scattering light is generated from the sample 415.

The transient Raman scattering light passes through the half mirror 413, is reflected by a half mirror 417 and enters a detecting optical system. The detecting optical system of this embodiment comprises a polarizer 418, a lens 419, a pinhole 420, a lens 421, a transmission diffraction grating 422 and an ICCD camera 423. In this case, the transient Raman scattering light condenses at the center of the pinhole 420 by the lens 419 via the polarizer 418, and enters the ICCD camera 423 having high sensitivity and based on a photoelectric conversion principle by using the lens 421 via the transmission diffraction grating 422. The pinhole 420 functions as a spatial filter and removes fluorescence and the like generated by the optical system and the like other than the sample 415, thereby being capable of raising the S/N ratio of the measurement. Furthermore, since the transmission diffraction grating 422 functions as a spectrum meter, the optical system can measure not only the transient Raman scattering light but also Raman spectra and time response for laser irradiation. It is thus possible to analyze the chemical structure and composition of the sample 415. Moreover, by relatively changing the polarization planes of the pump light and the probe light by using the polarizers 48 and 49, the space orientation information regarding the composition of the sample 415 can also be obtained.

As described above, the double-resonance-absorption microscope shown in FIG. 53 thus achieves a super-resolution microscope of a high-functional analysis type having excellent plane and three-dimensional resolutions by measuring a transient Raman scattering light.

FIG. 54 is a schematic block diagram showing an example of an electrical system for controlling the double-resonance-absorption microscope shown in FIG. 53. A whole microscope system including the double-resonance-absorption microscope is basically controlled by a computer 4101.

First, the computer 4101 controls the oscillation of an Nd:YAG laser 41 and controls the drive of the sample scanning stage 416 for the sample 415. The timing of the system wholly conforms to the clock signal of the computer 4101. The clock signal is divided by a frequency divider 4102 into a frequency at which laser oscillation is possible. Furthermore, the frequency-divided clock signal is delayed and wave-shaped by a gate & delay generator 4103 to obtain a Q switch signal for laser control. The obtained signal controls the Nd:YAG laser 41.

A transient Raman scattering light at each laser shot is monitored by the CCD array 4104 of the ICCD camera 423. More specifically, the transient Raman scattering light emitted from the sample 415 by a laser shot is subjected to spectroscopic processing by the transmission diffraction grating 422 and detected as a Raman spectrum by the CCD array 4104. The storage data of each pixel of the CCD array 4104 is transferred to the memory of the computer 4101 at each laser shot in synchronization with the movement of the sample scanning stage 416 and the emission of the laser. By numerical operation by the computer 4101, only the data of the wavelength of a specific Raman scattering light is extracted from the Raman spectrum data stored in the memory (not shown) of the computer 4101, and the two-dimensional scanning image of the sample 415 is formed.

By analyzing the two-dimensional scanning image with respect to each of the measured wavelengths as described above, not only the image due to the transient Raman scattering light can be obtained, but also the Raman spectrum can also be measured. Thus, the two-dimensional composition analysis of the sample 415 can be carried out in a diversified manner. The two-dimensional scanning image data, analysis data and the like are stored in a storage means (not shown), and output to an external output means, such as a display 4105 and a printer 4106.

EXAMPLE 8

An example of a molecule wherein a singlet transient Raman scattering light and a triplet transient Raman scattering light can be observed properly will be introduced herein.

In paratetraphenyl having three benzene rings connected in series, for example, an absorption band from $S_0$ to $S_1$ is present and centered at a wavelength of 300 nm, and a transient absorption band from $S_1$ to $S_2$ expands around 500 nm. The transient Raman scattering spectra of its C—CH group and the like are developed on the long wavelength side from 500 nm.

Furthermore, in each derivative of 5-dibenzosuberene, its absorption band from $S_0$ to $S_1$ is present around a wavelength of 280 nm, and the transient absorption band from $S_1$ to $S_2$ expands around 600 nm. The molecule is obtained in a high yield of several tens of percent or more, and its level shifts to the lowest triplet level $T_1$. A transient absorption band is present from the lowest triplet level $T_1$ to a higher triplet level near 420 nm. Since fluorescence is not emitted at all after absorption in the transient absorption band, it is possible to detect a transient Raman scattering light at an excellent S/N ratio. In addition, the transition from the $S_1$ state to the lowest triplet level $T_1$ takes a time of several $\mu$ seconds. The time interval between the pump light and the probe light can be made large. Hence, the Raman scattering light can be separated easily from the pump light, and the S/N ratio can be raised further.

The above description is also applicable similarly to each flavoprotein molecule in flavin nucleotide, an interesting compound in biology. It is thus possible to fractionate Chemical groups, such as C=C, C=O, $CH_2$—, CHOH— and CN—.

In the double-resonance-absorption microscope in accordance with the present invention, a sample molecule to be excited should be a cation from the viewpoint of highly accurate measurement or the like of a transient Raman scattering light.

As described above in detail, the present invention provides a completely novel double-resonance-absorption microscope capable of achieving plane and three-dimensional resolutions at a super-resolution exceeding the diffraction limit of an emitted light, and also capable of performing accurate sample analysis.

[X] A Novel Fluorescence Correlation Method

A novel fluorescence correlation method in accordance with the present invention will be described below.

A conventional fluorescence correlation method capable of performing fluorescence analysis at a single molecule level has been used for a long time to perform analysis regarding the diffusion movement of particles, such as Brownian movement. For example, it is assumed that a narrow laser excitation beam is applied to a dilute solution of fluorescence molecules to measure the intensity of fluorescence for a long time. The intensity of fluorescence is proportional to N: the number of fluorescence molecules in a measurement area. Hence, the magnitude of a fluctuation becomes $(1/N)^{1/2}$ when expressed in terms of S/N.

The fluorescence correlation method is a method for measuring the magnitude of a small fluctuation of fluorescence and time correlation described later. A time during which a fluorescence correlation function is halved, that is, a correlation time $T_0$, is expressed by the following equation.

$$\tau_0 = \frac{W^2}{4D} \quad (\text{Eq.42})$$

In Eq. 42, D is a translation diffusion coefficient of a fluorescence molecule, and W is the radius of a laser beam at the time when the intensity distribution function of the laser beam in the radial direction is a Gaussian distribution. Physically, the $\tau_0$ corresponds to a time during which the fluorescence molecule crosses a laser beam due to diffusion.

At the time of measuring the fluctuation of fluorescence, the output current f(t) of a photomultiplier tube is measured. In the case when a laser beam is not extremely large, the amount of fluorescence is proportional to f(t). In reality, obtaining a fluorescence correlation function is none other than obtaining a correlation function regarding time with respect to f(t). This correlation function, G(x), is expressed by the following equation:

$$G(\tau) = \frac{\int_0^T f(t)f(t+\tau)dt}{\int_0^T f(t)f(t)dt} \quad (\text{Eq.43})$$

If the intensity of the laser has a distribution close to a Gaussian distribution, the equation can be simplified as follows:

$$G(\tau) = \frac{1}{N} \cdot \frac{1}{1+\frac{\tau}{\tau_0}} \quad (\text{Eq.44})$$

Furthermore, the fluorescence correlation method is used to measure a physical quantity for obtaining the translation diffusion coefficient (D in Eq. 42) of the fluorescence molecule as described above. However, the method can basically measure any quantity by using the same principle, provided that the quantity is a thermodynamic quantity causing a fluctuation of fluorescence.

Figure 55:
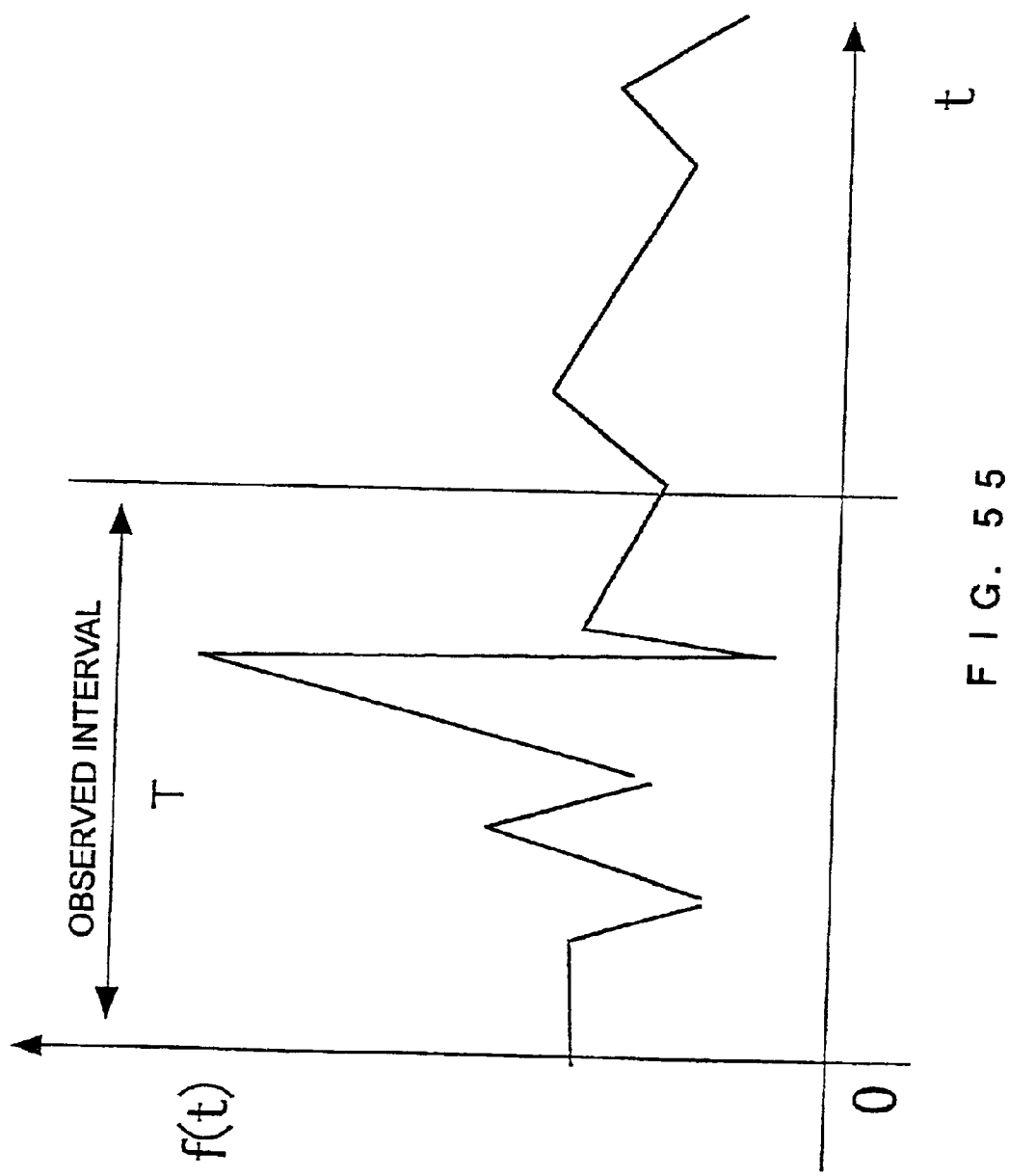
FIG. 55 is a diagram illustrating the prior art fluorescence correlation method.

For example, when a fluorescence molecule flows and crosses a laser beam, a fluctuation of fluorescence is observed. In addition, when a fluorescence molecule combines with other molecules by a chemical reaction or the like, the velocity of the molecule can be observed as a fluctuation. In other words, the progress of the chemical reaction can be known in real time. Furthermore, the rotation motion of a molecule can also be measured by polarization analysis. It is obvious that the number of molecules present in an observation area can also be measured directly from the intensity of G(τ). More specifically, for example, as shown in FIG. 55, a fluctuation function f(t) within a specific amount of time during which an expected fluctuation phenomenon is completed is measured, and a correlation function should be obtained by using the above-mentioned Eq. 43 on the basis of the measured f(t). Generally speaking, fluorescence correlation analysis for pigment molecules by using a continuous oscillation argon or krypton laser has become mainstream as an excitation light source.

Figure 56:
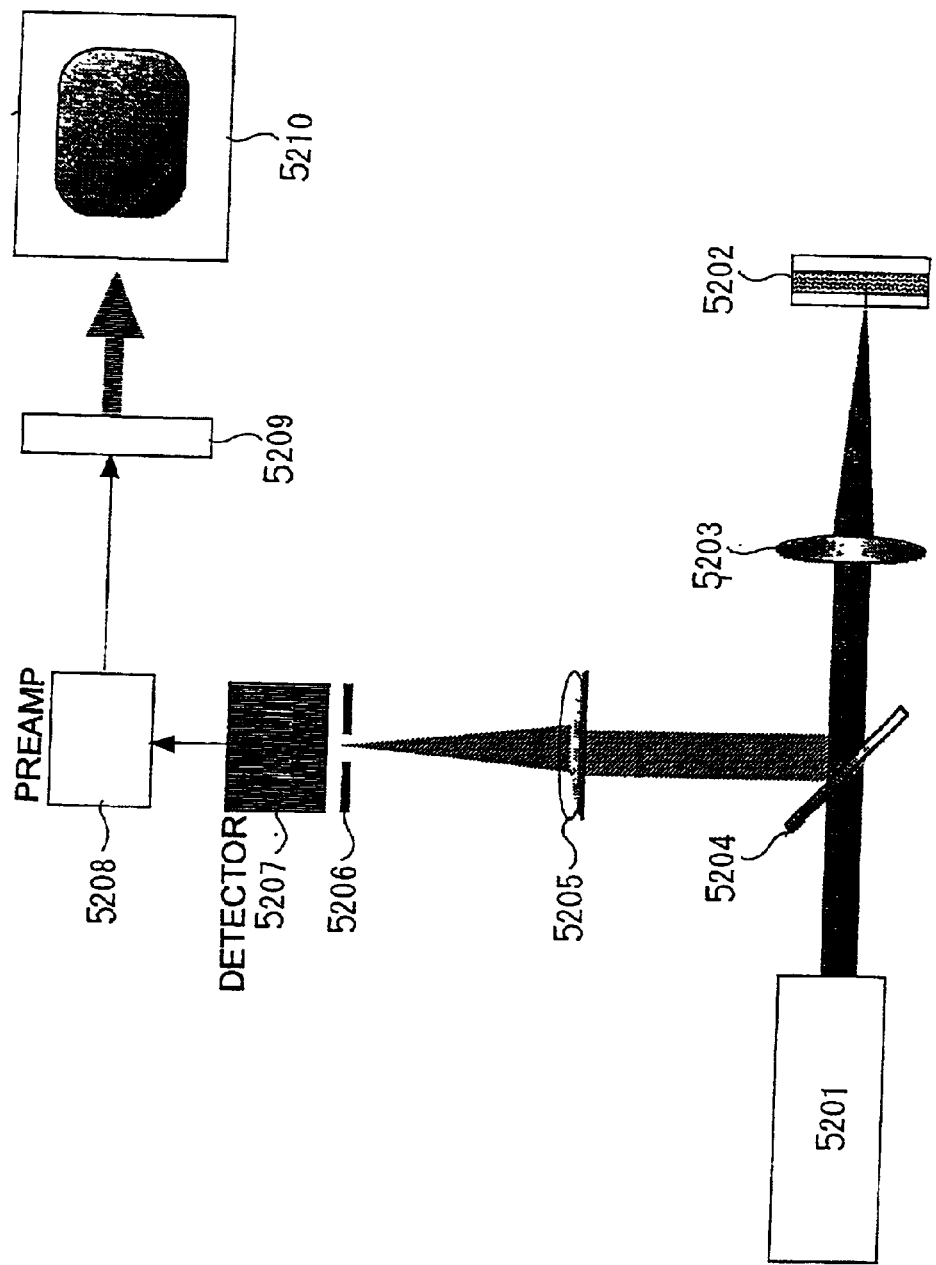
FIG. 56 is a schematic diagram of a typical example of a system for performing fluorescence correlation analyses using the prior art fluorescence correlation method.

FIG. 56 shows a typical example of a system for fluorescence correlation analysis by using the fluorescence correlation method. The system shown in FIG. 56 uses a continuous oscillation laser 5201, such as an argon laser, as an excitation light. The laser beam is condensed by a lens 5203 so that an observation sample solution 5202 including a fluorescent dye is irradiated. Fluorescence is subjected to collimation by a lens 5203, folded by a beam split mirror 5204 and condensed again by a lens 5205. The condensed fluorescence passes through a pinhole 5206 and is detected by a detector 5207, such as a photomultiplier tube or a CCD. The detected, fluorescence is output as a current. The current is amplified by a preamplifier 5208 and converted into digital data by an analog-digital converter 5209. In the end, the digital fluorescence signal is stored in the memory of a computer 5210 as time-series data. Inside the computer 5210, correlation function G(τ) is calculated in accordance with Eq. 43.

However, the conventional fluorescence correlation method has the following problems in actual practice.

Figure 57:
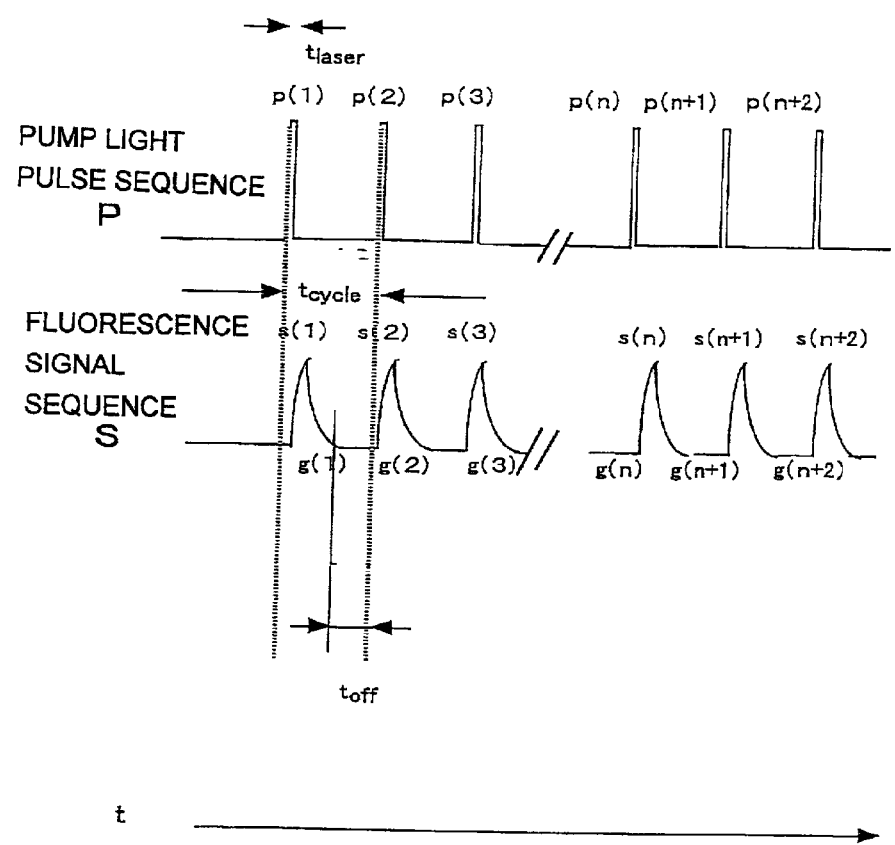
FIG. 57 is a time chart illustrating the relation between pump light and a fluorescence signal in a measuring system using a pulsed laser as an excitation light source.

The conventional fluorescence correlation method is based on the understanding that fluorescence changes continuously with time used as a function within an amount of time. On the other hand, in the case of a measurement system using a high-repetition pulse laser as an excitation light source, the emission of the excitation light becomes intermittent as shown in FIG. 57, for example. As a result, a fluorescence signal is observed as an intermittent pulse wave. For this reason, the conventional fluorescence correlation method cannot be used.

More specifically, in the case when a high-repetition pulse laser is used as an excitation light source, there is a time period $t_{off}$ during which no excitation pulse is present and no fluorescence signal is present as shown in FIG. 57. In this time period, signal components having no relation to the fluctuation of a fluorescence molecule, such as just noise from detectors or extraneous stray light, are observed. If a fluorescence correlation is obtained from Eq. 43 at this time, integration is carried out while such signal components having no relation to a fluorescence phenomenon remain included. In an extreme case, if the time period $t_{on}$ of fluorescence emission is shorter than $t_{off}$, a fluorescence correlation function indicating the fluctuations of the dark currents of detectors, such as a photomultiplier tube, is measured, instead of measuring a fluorescence correlation function indicating the fluctuation of the fluorescence molecule. For this reason, the conventional fluorescence correlation method is not applicable to a system wherein a pulse laser is used as an excitation light source.

Furthermore, in the above-mentioned novel double-resonance-absorption microscope in accordance with the present invention as well as the conventional double-resonance-absorption microscope developed by the inventor of the present invention, a pulse laser is frequently used as an excitation light source. Hence, the conventional fluorescence correlation method cannot be used for these microscopes.

Figure 58:
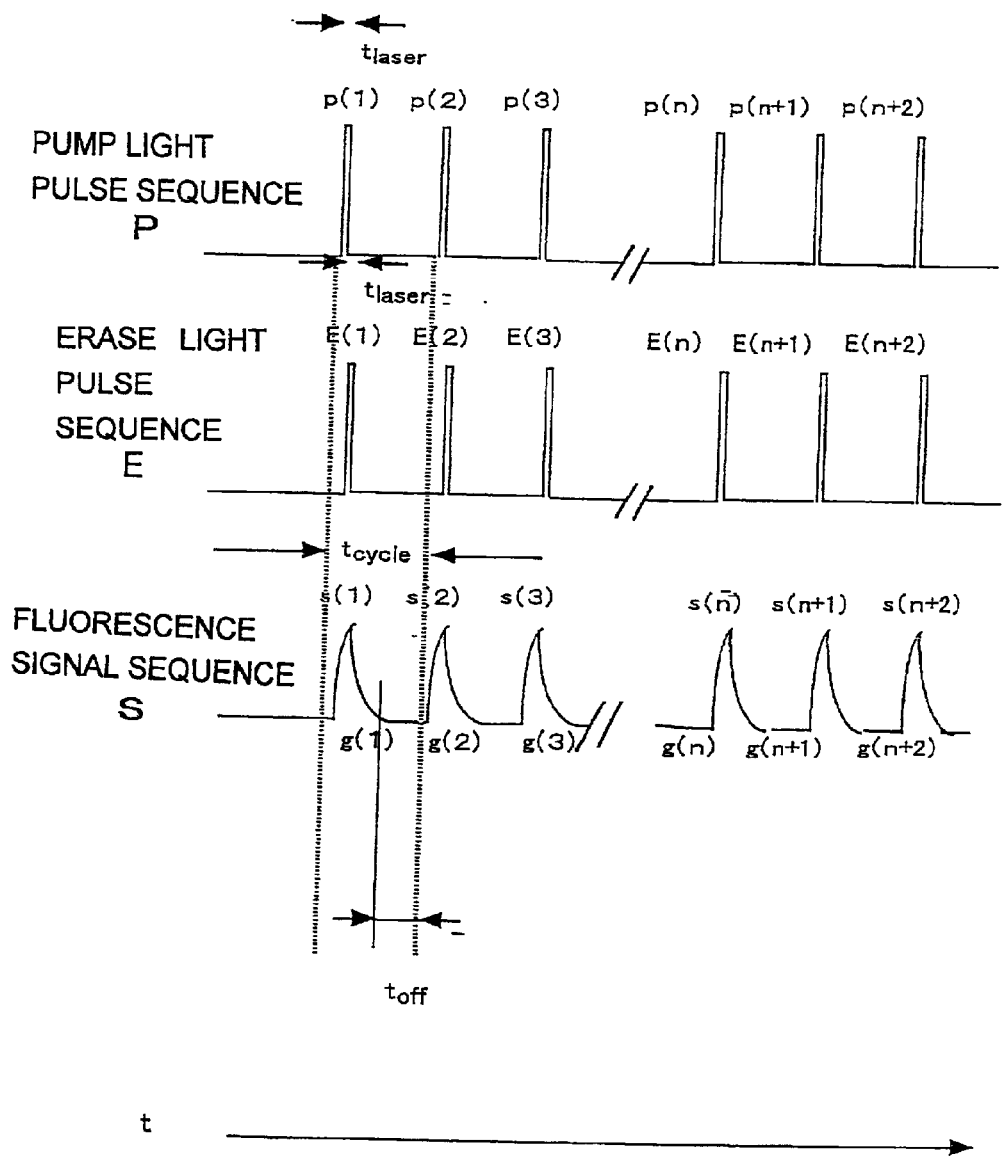
FIG. 58 is a time chart illustrating the relation among pump light, erase light, and a fluorescence signal in a double-resonance absorption microscope.

In other words, in the double-resonance-absorption microscope, as shown in FIG. 58 for example, it is necessary to irradiate a sample with a pump light and an erase light (a probe light in the case when the transient Raman scattering process is used in combination (see [IX. b])) at delicately controlled timing. Furthermore, the erase light for inhibiting fluorescence is required to have a very high intensity. For this reason, even if an appropriate filter is provided on an optical path to a detector, stray light from the pump light and the erase light (stray light from the erase light having a high intensity, in particular) may enter the detector. If only one fluorescence molecule is present in the observation area, the intensity of the fluorescence signal becomes relatively lower with respect to the stray light. Hence, even if fluorescence correlation is measured, undesired "fluctuation of the light source" is measured.

To solve the above-mentioned problems, a novel fluorescence correlation method in accordance with the present invention is intended so that a fluorescence correlation function due to only a fluorescence phenomenon can be measured accurately by a double-resonance-absorption microscope using pulse light sources and by other various systems.

Figure 59:
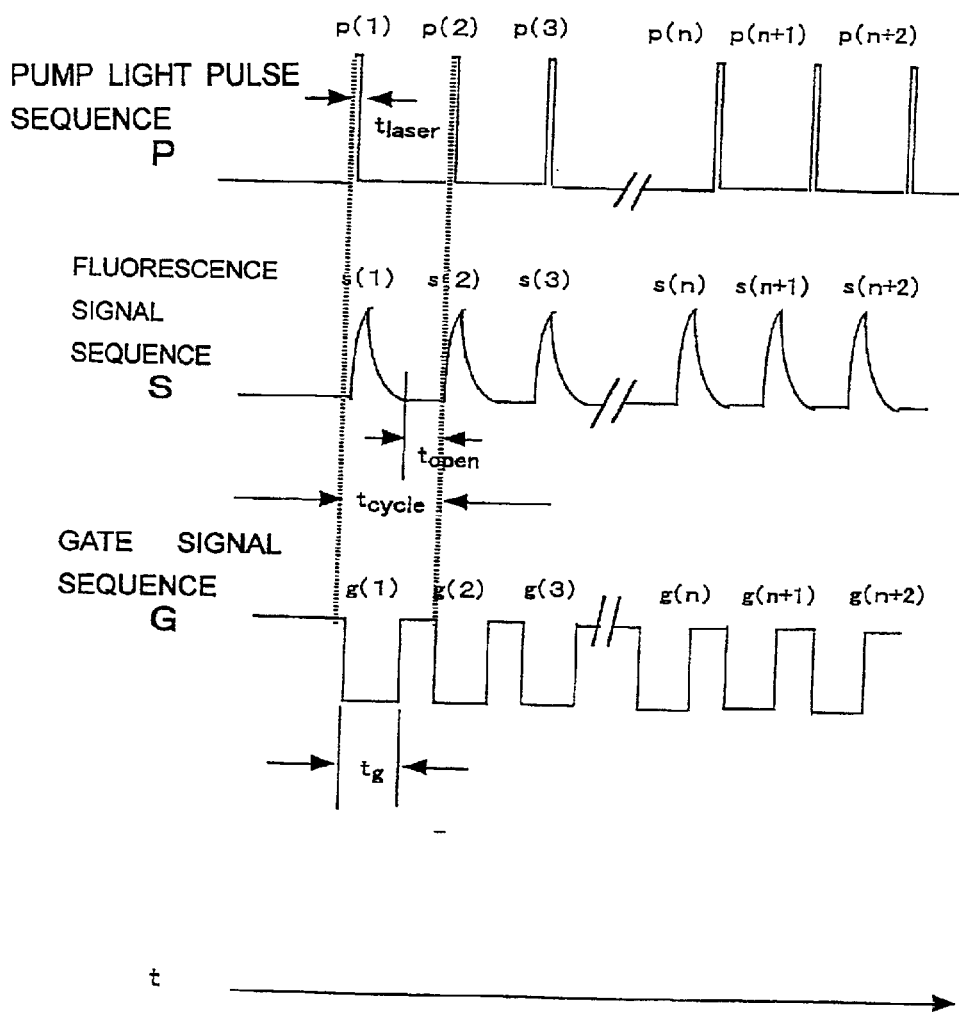
FIG. 59 is a diagram illustrating the principle of a fluorescence correlation method in accordance with the present invention.

FIG. 59 is a view showing the fluorescence correlation method of the present invention. In FIG. 59, P designates a pulse train of a pulse excitation light (indicated as a pump light in the figure) from a pulse light source, such as a pulse laser oscillating at a cycle of $t_{cycle}$ and a pulse width of $t_{laser}$, indicating that emission is performed intermittently pulse-wise. S designates a fluorescence signal train, indicating that a fluorescence molecule is making emission at a fluorescence lifetime $t_g$ depending on the pulse-wise light irradiation. G designates the pulse train of a gate signal, a negative signal having a cycle of $t_{cycle}$ and a pulse width of $t_g$. The cycle of this pulse train of the gate signal is completely synchronized with the cycle of the fluorescence emission. The pulse train has no phase shift, and has the same pulse width as the width of the lifetime of fluorescence.

FIG. 59 also shows a time period $t_{open}$ wherein the pulse of the gate signal for pulse laser control is present although no fluorescence signal is present. Since no fluorescence signal is present in this time period $t_{open}$, the time period $t_{open}$ does not relate to measurement at all. If an attempt is made to obtain a fluorescence correlation function by using the above-mentioned Eq. 43 in accordance with the conventional fluorescence correlation method in the situations described above in a measurement time T, the meaningless integration period $t_{open}$ is included in the calculation. As a result, unnecessary fluctuations due to detectors and light sources are integrated.

To solve this problem, in the fluorescence correlation method of the present invention, the time period $t_{open}$ appearing periodically is eliminated from the integration period, thereby improving the quality of the signal. More specifically, the fluorescence correlation method of the present invention uses a correlation function given by the following equation:

$$G(\tau)^* = \frac{\sum_{j=0}^{M} \int_{j \cdot t_{cycle}}^{j \cdot t_{cycle}+t_g} f(j \cdot t_{cycle}+t)f(j \cdot t_{cycle}+\tau+t)dt}{\sum_{j=0}^{M} \int_{j \cdot t_{cycle}}^{j \cdot t_{cycle}+t_g} f(j \cdot t_{cycle}+t)f(j \cdot t_{cycle}+t)dt} \quad (Eq.45)$$

where τ designates an integral multiple of $t_{cycle}$ and is given by the following equation:

$$\tau = i \cdot t_{cycle} \quad (Eq. 46)$$

where i designates an integer.

Figure 60:
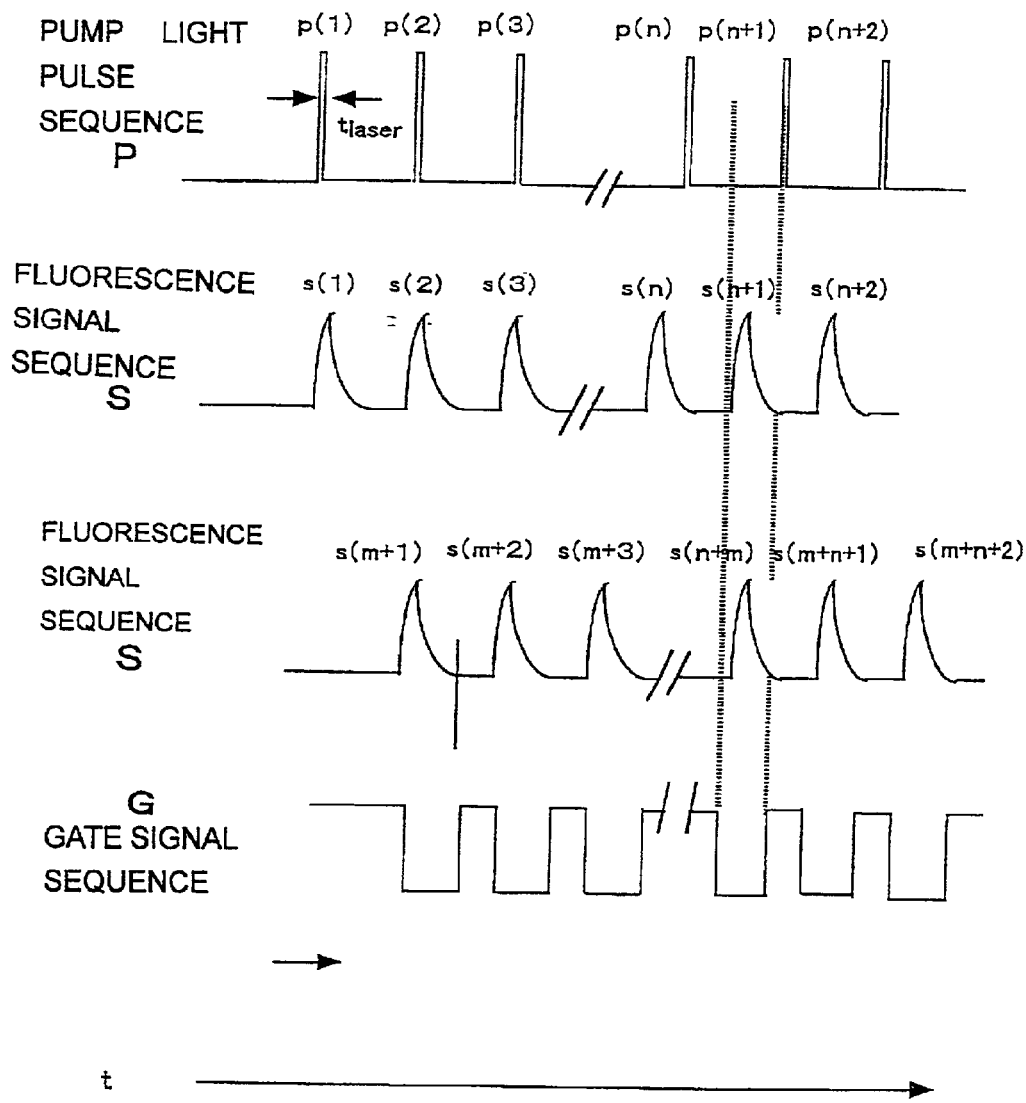
FIG. 60 is another diagram illustrating the principle of the fluorescence correlation method in accordance with the present invention.

FIG. 60 shows this relationship. In other words, as shown in FIG. 60, the product of a fluorescence signal s(j) and a pulse signal s(j+1) is integrated while the phase is shifted completely by $t_{cycle}$ multiplied by integer i in a quantization manner. Then, the sum of all j values with respect to n in the measurement time is calculated. This results in calculating the numerator of the right side of Eq. 45. As for the denominator, the product of s(j) and s(j+1) should only be subjected to the same operation. The correlation function G (τ)* obtained by the calculation is not continuous but has discrete values at intervals of $t_{cycle}$ as indicated by Eq. 46 (see FIG. 61). It is needless to say that the envelope of the values has the same physical meaning as that of G(τ) of Eq. 43.

Hence, in accordance with the fluorescence correlation method of the present invention, only the fluctuation solely due to a fluorescence phenomenon can be detected, without including any unnecessary fluctuations due to detectors and light sources. It is thus possible to achieve fluorescence analysis at high sensitivity and high accuracy.

Furthermore, in the case when the fluorescence correlation method of the present invention is used for the above-mentioned double-resonance-absorption microscope for example, a pulse light source is synchronized with a gate signal for controlling the timing of capturing a signal in a detector. In addition, f(t) is obtained by measuring a fluorescence signal generating intermittently in time sequence. Then, calculation should only be carried out on the basis of Eq. 45 by using hardware or software means.

EXAMPLE 9

FIG. 62 is a schematic block diagram showing an example of a fluorescent correlation measurement system for achieving the fluorescence correlation method of the present invention.

The whole fluorescent correlation measurement system shown in FIG. 62 is basically controlled by a computer 5101. First, the computer 5101 generates a reference clock signal. On the basis of this signal, the computer 5101 controls the oscillation of a pulse laser 5102 serving as a pulse light source, controls the drive of a sample (not shown) on which a sample 5103 is mounted, and controls various data.

More specifically, the timing of the system conforms entirely to the clock signal of the computer 5101. This clock signal is frequency-divided by a frequency divider 5104 into a frequency at which laser oscillation is possible. First, the frequency-divided clock signal is delayed and wave-shaped by a gate & delay generator 5105 so as to be converted into a Q switch pulse signal for laser control. The oscillation of the pulse laser 5102 is controlled by this Q switch pulse signal. On the other hand, a pulse signal from the gate & delay generator 5105, synchronized with the Q switch pulse signal, is used so that the sample scanning stage for the sample 5103 is driven in synchronization with the oscillation of the pulse laser 5102. Furthermore, a gate pulse signal, i.e., a gate signal synchronous with the Q switch pulse signal and required for fluorescence correlation measurement, is supplied from the gate.& delay generator 5105 to a line selector 5108 to be described later.

The pulse laser beam from the pulse laser 5102 oscillated in accordance with the Q switch pulse signal is condensed and emitted to the sample 5103 via various optical systems. Fluorescence is generated from the sample 5103 at each shot of the pulse laser beam.

The fluorescence generated at each shot of the pulse laser beam is detected by a detector 5106. The detector 5106 basically comprises a spectroscope, such as a diffraction grating, and an ICCD camera, for example. The ICCD camera has a basic configuration wherein a photoelectron conversion face is provided on each of the front and rear sides of a micro-channel plate. In the ICCD camera, incident light is converted into electrons by the front-side photoelectron conversion face, the electrons are amplified by the micro-channel plate, and the amplified electrons are converted again into light by the rear-side photoelectron conversion face. The spectroscope, such as a diffraction grating, is disposed ahead of the input side of the ICCD camera. In this case, fluorescence generated at each shot is subjected to spectroscopic processing by the spectroscope at the detector 5106 and is detected as a fluorescence spectrum by the ICCD camera. The total light amount in its fluorescence wavelength area is output as an analog signal from the ICCD camera. This analog signal is amplified by a preamplifier 5107 and input to the line selector 5108.

The line selector 5108 is a device that allows one of two analog signals input independently of each other to pass depending on the polarity of a gate pulse signal. In this embodiment, analog fluorescence signals are input to the line selector 5108 via the preamplifier 5107. In addition, the gate pulse signal from the gate & delay generator 5105 is also input to the line selector 5108 as described above. When the gate pulse signal has a negative level the line selector 5108 allows the fluorescence signal from the pre-amplifier 5107 to pass. When the gate pulse signal has a positive level, the line selector 5108 outputs a ground-level signal, i.e., a zero-level signal. The pulse laser 5102 oscillates at the lowering edges of the gate pulse signal, and the pulse width of the oscillation is exactly equal to the time width of the output signal from the preamplifier 5107. For this reason, the fluorescence signal passes through the line selector 5108 only during the time of fluorescence emission, i.e., the time corresponding to the pulse width. This corresponds to the above-mentioned FIG. 59. in effect, only the fluorescence signal passes through the line selector 5108.

Intrinsically, the gate pulse signal is generated by frequency-dividing the system clock signal of the computer 5101. The pulse frequency of the gate pulse signal is thus an integral submultiple of the system clock signal. The output signal of the line selector 5108 is sampled at the frequency of the system clock signal.

The system clock signal also drives a counter 5111. The output of the counter 5111 gives the memory addresses of a line memory 5110. In synchronization with this memory address signal, the fluorescence signal is digitized by an A/D converter 5109 and stored in the line memory 5110. By this data transfer, all the data in the observation time, required to obtain the fluorescence correlation function at the time when a specific observation area is irradiated with a laser beam, is stored in the line memory 5110.

The data stored in the line memory 5110 is transferred to the memory of the computer 5101 via an I/O port 5112 at the timing requested by the computer 5101.

By repeating the above-mentioned procedure, data required to calculate the fluorescence correlation function for each pixel is transferred to the memory of the computer 5101 in synchronization with the movement of the sample scanning stage and laser emission.

The fluorescence spectrum data stored in the memory of the computer 5101 is converted into the fluorescence correlation function for each pixel by the numerical operation of the computer 5101.

This fluorescence correlation measurement system may have a configuration wherein the fluorescence image of the sample 5103, obtained by the irradiation of the light of a mercury lamp or the like, is monitored simultaneously by a CCD camera and the image data is stored in a frame memory as necessary. In this case, the whole fluorescence image of the sample 5103 can be monitored as necessary, separate from a two-dimensional scanning image. Furthermore, the computer 5101 carries out image display and image processing as necessary. Obtained image data is output by an output means, such as a display 5113 or a video printer 5114.

Figure 63:
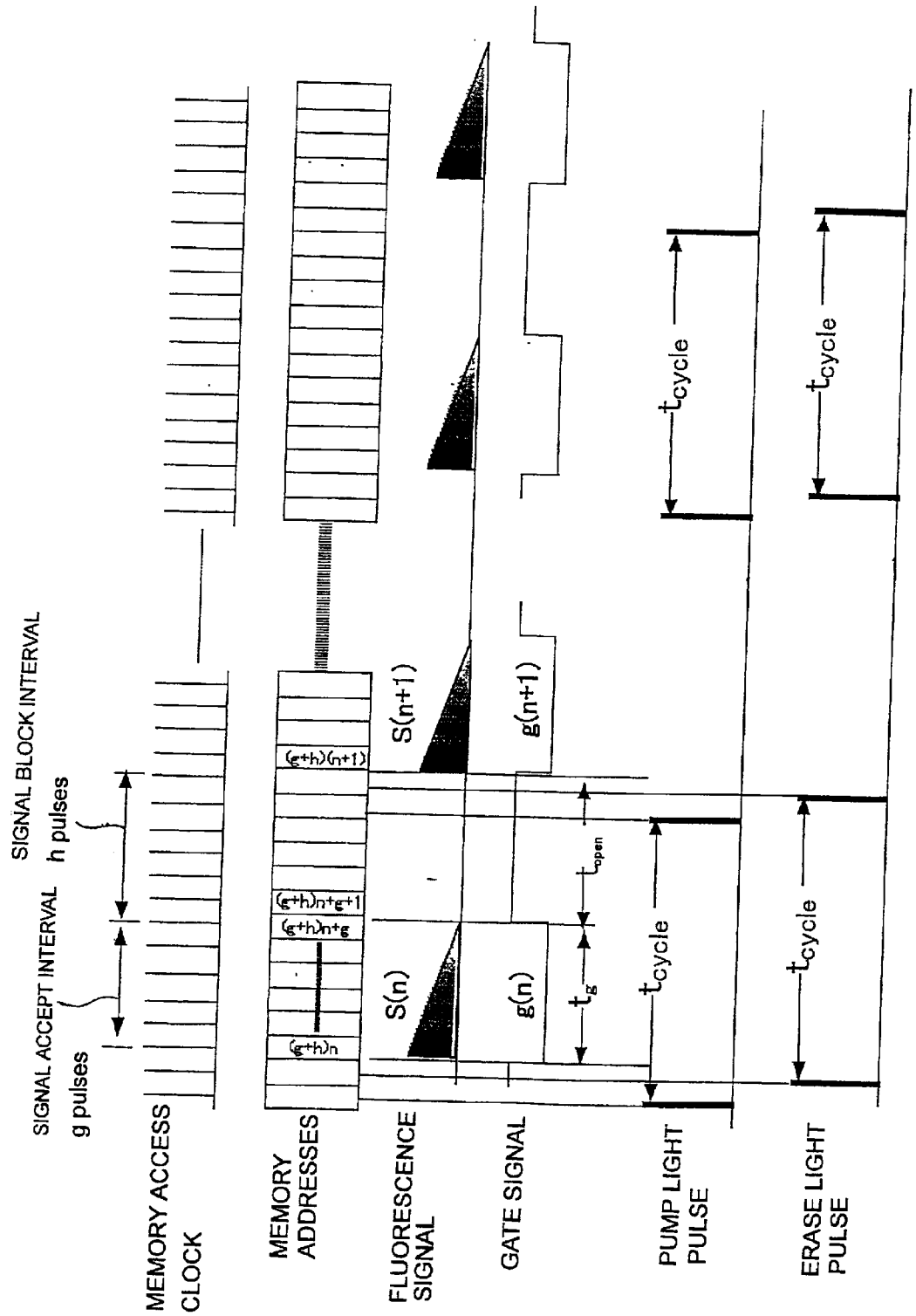
FIG. 63 is a time chart where a fluorescence signal consisting of a pulse sequence (from the S(n)th pulse to the S (n+1) th pulse) is applied to a line memory 110 on each laser shot in the fluorescence correlation measurement system shown in FIG. 62.

How the fluorescence signal is stored in the line memory 5110 will be further described below referring to FIG. 63. FIG. 63 is a time chart in the case when the S(n)th pulse and the S(n+1)th pulse of the pulse train of a fluorescence signal, each generated at each laser shot, are input to the line memory 5110. In FIG. 63, on the assumption that the fluorescence correlation method of the present invention is applied to double-resonance-absorption microscopes using the double-resonance absorption process or double-resonance-absorption microscopes using both the double-resonance absorption process and the transient Raman scattering process in combination, two wavelength lights, a pump light and an erase light (a probe light in the case when the transient Raman scattering process is also used in combination (see [IX. b])), are generated by using the laser beam from the pulse laser 5102.

In FIG. 63, the memory access clock signal corresponds to the system clock signal of the computer 5101. The addresses of the line memory 5110 are output from the counter 5111 at the timing of the memory access clock signal. The clock signal is converted into a gate pulse signal (a gate signal in FIG. 63) and a Q switch pulse signal via the frequency divider 5104 and the gate & delay generator 5105 as described above. The gate pulse signal for controlling the line selector 5108 has a negative level during the time width $t_g$ of each pulse of the fluorescence signal and has a positive level during the time width $t_{open}$ during which the fluorescence signal is not present. The pulses of the pump light and the erase light generate periodically at intervals of the time width $t_{cycle}$. The fluorescence signal and the gate pulse signal are output at intervals of $t_{cycle}$ as a matter of course. The time widths herein have the relationship of $t_{cycle} = t_g + t_{open}$.

FIG. 63 will be described below in accordance with another time sequence. First, the pulse signal of the pump light is generated by the Q switch pulse signal obtained by frequency-dividing the memory clock signal. Then, the pulse signal of the erase light delayed by the amount of an optical path is generated. The fluorescence signal S(n) having the time width $t_g$ is output from the preamplifier 5107 by the pulse signals of the pump light and the erase light. The cycle of the gate pulse signal is completely synchronous with the cycle of laser drive, i.e., the cycle of the Q switch pulse signal. However, the gate pulse signal develops a negative level (g(n) in FIG. 63), slightly delayed after the generation of the pump light and the erase light, and this state continues during the time $t_g$. The gate pulse signal repeats this change at intervals of $t_{cycle}$ during the time T sufficient to obtain a fluorescence correlation. With the operation described above, the line selector 5108 supplies the signal generated during the time period when S(n) is present to the A/D converter 5109. During the other time periods, the line selector 5108 supplies a zero-level ground voltage signal. As a result, signals due to the fluctuation of the detector 5106 and laser scattering light are not output from the line selector 5108 and not input to the A/D converter 5109.

The timing of the sampling for A/D conversion coincides with the timing of the system clock signal supplied by the computer 5101. Data is written in specific addresses of the line memory 5110 in accordance with the timing. As important assumptions at this time, the frequency of the gate pulse signal must be lower than that of the system clock signal, and a piece of digital data must be obtained from the fluorescence signal S (n) at least at one laser shot. In FIG. 63, sampling is carried out for (g+h) pieces of data in the period $t_{cycle}$. More specifically, the effective fluorescence signal S(n) is subjected to sampling for the g pieces, and the zero level signal substantially irrelevant to the fluorescence correlation is subjected to sampling for the h pieces. The sampling frequency thus becomes the repetition frequency of the laser oscillation multiplied by (g+h) as a matter of course. In other words, the laser drive pulse signal (i.e., the Q switch pulse signal) is obtained by frequency-dividing the system clock signal by (g+h). In FIG. 63, the digitized data of S(n) is stored in the range of the address n(g+h) to the address n(g+h)+g in accordance with the addresses specified by the counter 5111. In effective zero signals are present in the range of the address n(g+h)+g+1 to the address (1+n)(g+h). In this way, the fluorescence signal data in the range of S (1) to S (M) is stored in the range of the address 1 to the last address inside the line memory 5110.

As described above, the fluorescence correlation function at one measurement point can be obtained from the fluorescence signal data in the range of S(1) to S(M) measured during the observation period T. More specifically, the data in the line memory 5110 is transferred once to the memory of the computer 5101 via the I/O port 5112. As a result, M(g+h) pieces of digital data in total are present in the memory of the computer 5101. It is herein assumed that an array name D1 is given to this data group and that the arrays in the range of D(1) to D(M(g+h)) are used as specific data for the calculation of the fluorescence correlation function G(τ)*. In this case, since the fluorescence data S(n) is present intermittently, τ has discrete values, that is, only the integral multiple values of (g+h) corresponding to the intervals of the laser repetition. When it is assumed that the label integer is k, k has an integer value in the range of 1 to M. For this reason, the function is given as a discrete array group G(k)* at the time when numerical operation is carried out inside the computer 5101. By carrying out the integration calculation given by the following Eq. 47 in accordance with Eq. 45, the fluorescence correlation function G(k)* in the observation period can be obtained at each observation point. Since the integration in Eq. 45 generates a non-contiguous function, it is changed to a form of summation.

$$G(k)^* = \frac{\sum_{j=1}^{M-K} \sum_{i=j(g+h)}^{j(g+h)+g} D(i+k(h+g))D(i)}{\sum_{j=1}^{M} \sum_{i=j(g+h)}^{j(g+h)+g} D(i)D(i)} \quad (\text{Eq. 47})$$

In Eq. 47, integration time periods unnecessary for numerical operation are omitted. Hence, the correlation function can be calculated without using the line selector 5108 in principle. Furthermore, when the storage state in the memory in FIG. 63 is viewed, zero values are present in the line memory 5110 during the period $t_{open}$. A double-summation in consideration of the integration period shown in Eq. 47 is not always necessary, and the simplified numerical operation of the following Eq. 48 may be carried out instead.

$$G(k)^* = \frac{\sum_{i=1}^{(M-K)(h+g)} D(i+k(h+g))D(i)}{\sum_{i=1}^{M(h+g)} D(i)D(i)} \quad (\text{Eq. 48})$$

Since only one summation is performed in Eq. 48, numerical operation is processed simply. Operation algorithms and hardware design can thus be simplified.

In the case when correspondence can be achieved for the memory addresses wherein the data of the pulse train S(n) of the fluorescence signal is present, the above-mentioned fluorescence correlation method of the present invention is applicable to the system shown in FIG. 56.

As described above, in accordance with the fluorescence correlation method of the present invention, the fluorescence correlation function is obtained while eliminating data components in periods having no fluorescence signal components at all between intermittent fluorescence signals. Hence, components other than those of the fluctuation of the fluorescence molecule can be eliminated accurately. Therefore, by measuring only the fluorescence correlation function solely due to the fluctuation of the fluorescence molecule and by analyzing the obtained fluorescence correlation function, the physical quantities from the sample 5103, such as the transfer rate, the viscosity and the number of the fluorescence molecules, can be obtained accurately. Furthermore, by making two-dimensional rearrangement in the memory of the computer 5110, the two-dimensional image of the sample 5103 can be formed in a diversified manner. In other words, the fluorescence correlation method of the present invention can achieve excellent fluorescence analysis by fluorescence correlation measurement even when a pulse light source is used as an excitation light source.

EXAMPLE 10

FIG. 64 is a schematic view showing an embodiment of a double-resonance-absorption microscope. The double-resonance-absorption microscope shown in FIG. 64 is a double-resonance-absorption microscope wherein both the double-resonance-absorption process and the transient Raman scattering process are used in combination. The configuration of this microscope is completely the same as that of the microscope shown in FIG. 53 (see [IX. b]). In this case, an Nd:YAG laser 51 is used as the light source for a pump light and a probe light, that is, a pulse light source. The fluorescence correlation method of the present invention can achieve excellent fluorescence analysis by measuring the fluorescence correlation function solely due to the fluctuation of the fluorescence molecule in a way similar to that described above.

A similar effect can also be achieved by the above-mentioned various double-resonance-absorption microscopes using only the double-resonance-absorption process. Specifically, the double-resonance-absorption microscopes include at least a light source for a pump light of a wavelength $\lambda_1$ which excites a sample molecule to a first electronic excited state from a ground state, a light source for an erase light of a wavelength which excites the sample molecule to a second electronic excited state or a higher excited state from the first electronic excited state, and an overlap component for partially overlapping irradiating areas of the pump light and the erase light with each other. Thus, an emission area upon deexcitation of the sample molecule from the first electronic excited state to the ground state is partially inhibited by irradiating the pump light and the erase light through the overlap component, or optical response from the overlapping irradiating areas of the pump light and the erase light on the sample is detected.

Hence, when the fluorescence correlation method of the present invention is used for a double-resonance-absorption microscope provided with a pulse light source serving as the light source for the pump light and the erase light or the probe light, a super-resolution is achieved (image formation in a spatial resolution of several tens of nm, for example) as a characteristic of the double-resonance-absorption microscope. In addition, various physical quantities can be analyzed and mapped two-dimensionally by using the fluorescence correlation function.

The components of the double-resonance-absorption microscope shown in FIG. 64 are the same as those shown in FIG. 53. The configuration of the microscope will be described below again.

The double-resonance-absorption microscope wherein both the double-resonance absorption process and the transient Raman scattering process are used in combination, comprises at least a light source for a pump light of a wavelength $\lambda_1$ which excites a sample molecule to a first electronic excited state of a singlet state from a ground state, a light source for a probe light of a wavelength $\lambda_2$ which excites the sample molecule to a second electronic excited state or a higher excited state of a singlet state from the first electronic excited state (in the case of using a singlet transient Raman scattering process) or a light source for a probe light of a wavelength $\lambda_3$ which excites the sample molecule, transited to a triplet level lower in energy than the first electronic excited state from the first electronic excited state, to a higher excited triplet level from the triplet level (in the case of using a triplet transient Raman scattering process), and an overlap component for overlapping a part or all of the irradiating areas of the pump light and the probe light with each other. A sample is irradiated with the pump light and the probe light through the overlap means, and a transient Raman scattering light emitted from an area in the sample where the pump light and the probe light overlap with each other is detected, as one basic configuration.

Alternatively, the double-resonance-absorption microscope comprises both of a light source for a probe light of a wavelength $\lambda_2$ and a light source for a probe light of a wavelength $\lambda_3$, and further comprises an irradiation time control component for controlling the time to irradiate a sample with the probe light of the wavelength $\lambda_2$ and the probe light of the wavelength $\lambda_3$. The sample is irradiated with the pump light and the probe light through the overlap component, and by the irradiation time control component, the probe light of the wavelength $\lambda_2$ is applied to the sample before the sample molecule transits to the triplet level from the first electronic excited state and the probe light of the wavelength $\lambda_3$ is applied to the sample after the sample molecule transits to the triplet level from the first electronic state. A transient Raman scattering light emitted from an area in the sample where the pump light and the probe light overlap with each other is detected, as another basic configuration.

The double-resonance-absorption microscope shown in FIG. 64 is an embodiment of the latter basic configuration.

First, by changing the wavelength of the basic wave of an Nd:YAG laser 51 using a KDP crystal 52, higher harmonics, such as 532 nm, 355 nm, 266 nm, etc. are generated by oscillation. By using an optical parametric generator 55, these lights are converted so as to have a wavelength $\lambda_1$ wherein a sample molecule to be observed can be excited from $S_0$ to $S_1$, and the light thus obtained is used as a pump light.

Furthermore, a part of the double harmonic is taken out via a half mirror 53, and enters another optical parametric generator 56 via a half mirror 54. The light is then converted so as to have a wavelength $\lambda_2$ wherein the sample molecule can be excited from $S_1$ to $S_2$ or a wavelength $\lambda_3$ wherein the sample molecule can be excited from $T_1$ to $T_2$, and the light thus obtained is used as a singlet probe light or a triplet probe light. The probe light is optically delayed by a delay optical system 57 to obtain an appropriate time difference between the probe light and the pulse pump light. The time difference can be controlled easily by the parallel translation of a prism 571 mounted on the delay optical system 57. More specifically, by the optical delay due to the optical path control of the delay optical system 57 serving as an irradiation time control means, the singlet probe light of the wavelength $\lambda_2$ is emitted to reach the face of the sample before the sample molecule makes a transition from the first electronic excited state $S_1$ of the singlet state to the triplet level $T_1$ after the irradiation of the pump light. On the other hand, after the irradiation of the pump light, the triplet probe light of the wavelength $\lambda_3$ is emitted to reach the face of the sample after the sample molecule makes a transition from the first electronic excited state $S_1$ of the singlet state to the triplet level $T_1$.

The probe light, the irradiation time of which is controlled as described above, enters a dichroic mirror 511 via a polarizer 59 and a swaying mirror 510 on its optical path. The pump light enters the dichroic mirror 511 via a polarizer 58 on its optical path. Both of the beams of light take the same optical path by virtue of the dichroic mirror 511. The polarizers 58 and 59 serving as polarized state changing means can freely rotate around the polarization planes of the pump light and the probe light.

Furthermore, by controlling the optical path of the probe light with respect to the pump light by using the swaying mirror 510 serving as an overlap component, the irradiating areas of the beams of light can be overlapped partially with each other on the condensing plane. The irradiating areas of the beams of light may be overlapped entirely as a matter of course. However, in order to have a higher plane resolution, it is desired that the irradiating areas should be overlapped partially and that the overlapped area should be made smaller.

The pump light and the probe light, the irradiating areas and time periods of which are controlled as described above, are formed by a relay lens 512, enter a half mirror 513, pass through an objective lens 514, and condense on a sample 515. The sample 515 is mounted on a sample scanning stage 516.

When the singlet probe light is emitted after the irradiation of the pump light, a singlet transient Raman scattering light is generated from the sample 515. When the triplet probe light is emitted, a triplet transient Raman scattering light is generated from the sample 515.

The transient Raman scattering light passes through the half mirror 513, is reflected by a half mirror 517 and enters a detecting optical system. The detecting optical system of this embodiment comprises a polarizer 518, a lens 519, a pinhole 520, a lens 521, a transmission diffraction grating 522 and an ICCD camera 523. In this case, the transient Raman scattering light condenses at the center of the pinhole 520 by the lens 519 via the polarizer 518, and enters the ICCD camera 523 having high sensitivity and based on a photoelectric conversion principle by using the lens 521 via the transmission diffraction grating 522. The pinhole 520 functions as a spatial filter and removes fluorescence and the like generated by the optical system and the like other than the sample 515, thereby being capable of raising the S/N ratio of the measurement. Furthermore, since the transmission diffraction grating 522 functions as a spectrum meter, the optical system can measure not only the transient Raman scattering light but also Raman spectra and time response for laser irradiation. It is thus possible to analyze the chemical structure and composition of the sample 515. Moreover, by relatively changing the polarization planes of the pump light and the probe light by using the polarizers 58 and 59, the space orientation information regarding the composition of the sample 515 can also be obtained.

As described above, the double-resonance-absorption microscope shown in FIG. 64 thus becomes a super-resolution microscope of a high-functional analysis type having excellent plane and three-dimensional resolutions by measuring a transient Raman scattering light. By using the above-mentioned fluorescence correlation method of the present invention together with the microscope, a wider variety of fluorescence analysis can be achieved.

The double-resonance-absorption microscope using the transient Raman scattering process detects a transient Raman scattering light from the overlapping areas of the pump light and the erase light on the sample. However, the signal that can be detected from the overlapping areas of the pump light and the erase light on the sample is not limited to the transient Raman scattering light, but fluorescence may be emitted from the second electronic excited state depending on a molecule. It is thus needless to say that the fluorescence correlation method of the present invention can be used with the double-resonance-absorption microscope for detecting optical response from the overlapping areas of both lights.

As described above in detail, the present invention provides a novel fluorescence correlation method capable of accurately measuring a fluorescence correlation function solely due to a fluorescence phenomenon even when a pulse light source is used.

What is claimed is:

1. A double-resonance absorption microscope, comprising:
   a pump light source for emitting a pump light having a wavelength $\lambda_1$ so as to excite a sample molecule from a ground state to a first electronic excited state;
   an erase light source for emitting an erase light having a wavelength $\lambda_2$ so as to excite the sample molecule from the first electronic excited state to at least a second electronic excited state;
   an overlap component for partially overlapping irradiating areas of the pump light and the erase light with each other so that an emission area is partially inhibited during de-excitation of the sample molecule from the first electronic excited state to the ground state by irradiating the pump light and the erase light through said overlap component;
   a spatial filter located on an optical path of the erase light to be emitted from said erase light source, said spatial filter including a condenser lens, a collimate lens, and a pinhole located between said condenser lens and said collimate lens, wherein said condenser lens, said collimate lens, and said pinhole are arranged so as to condense the erase light into said pinhole, to collimate the erase light having passed through said pinhole into a parallel beam, and to suppress wavefront disturbance of the erase light; and
   a phase modulation element for providing the erase light having passed through said spatial filter with a phase difference of $\pi$ around an optical axis of the erase light so as to produce a first-order Bessel beam.

2. The double-resonance absorption microscope of claim 1, wherein said phase modulation element comprises a substrate transparent and optically flat with respect to the erase light, and comprises an optical thin film evaporated on said substrate such that said optical thin film has a thickness distribution for providing the erase light with the phase difference of $\pi$ around the optical axis of the erase light.

3. The double-resonance absorption microscope of claim 1, wherein said phase modulation element comprises a substrate transparent and optically flat with respect to the erase light, said substrate being etched so as to be operable to provide the erase light with the phase difference of $\pi$ around the optical axis of the erase light.

4. The double-resonance absorption microscope of claim 3, wherein said erase light source is operable to emit erase light having a pulse width wider than a pulse width of the pump light, said pump light source and said erase light source being operable to emit pump light and erase light, respectively, such that an irradiation duration of the pump light completely overlaps an irradiation duration of the erase light.

5. The double-resonance absorption microscope of claim 4, further comprising a pulse width controller for widening the pulse width of the erase light so that the pulse width of the erase light is wider than the pulse width of the pump light.

6. The double-resonance absorption microscope of claim 5, wherein said pulse width controller comprises a pulse stretcher optical system including:
   a half mirror for providing light separation; and
   a reflection optical system for forming a loop optical path including said half mirror thereon.

7. The double-resonance absorption microscope of claim 4, further comprising an irradiation timing controller for controlling a timing of the pump light and the erase light reaching the sample molecule so that an irradiation duration of the pump light completely overlaps an irradiation duration of the erase light.

8. The double-resonance absorption microscope of claim 7, wherein said irradiation timing controller is operable to control an optical path difference of the pump light and the erase light so as to control the timing of the pump light and the erase light reaching the sample molecule.

9. The double-resonance absorption microscope of claim 7, wherein said pump light source comprises a pump light pulse laser and said erase light source comprises an erase light pulse laser independent of said pump light pulse laser, said irradiation timing controller being operable to control a Q-switch of each of said pump light pulse laser and said erase light pulse laser so as to control the timing of the pump light and the erase light reaching the sample molecule.

10. The double-resonance absorption microscope of claim 1, wherein a sample is dyed with a fluorescent labeler molecule having at least three electronic states including a ground state, the sample molecule comprising the fluorescent labeler molecule.

11. The double-resonance absorption microscope of claim 1, wherein at least one of said pump light source and said erase light source comprises a solid dye laser including:
   a solid laser medium wherein a dye molecule having more than two quantum levels is dispersed; and
   a short pulse laser for exciting said solid laser medium.

12. A double-resonance absorption microscope, comprising:
- a pump light source for emitting a pump light having a wavelength $\lambda_1$ so as to excite a sample molecule from a ground state to a first electronic excited state;
- an erase light source for emitting an erase light having a wavelength $\lambda_2$ so as to excite the sample molecule from the first electronic excited state to at least a second electronic excited state;
- overlap means for partially overlapping irradiating areas of the pump light and the erase light with each other so that an emission area is partially inhibited during de-excitation of the sample molecule from the first electronic excited state to the ground state by irradiating the pump light and the erase light through said overlap means;
- spatial filtering means located on an optical path of the erase light to be emitted from said erase light source, said spatial filtering means including a condenser lens, a collimate lens, and a pinhole located between said condenser lens and said collimate lens, wherein said condenser lens, said collimate lens, and said pinhole are arranged so as to condense the erase light into said pinhole, to collimate the erase light having passed through said pinhole into a parallel beam, and to suppress wavefront disturbance of the erase light; and
- phase modulation means for providing the erase light having passed through said spatial filtering means with a phase difference of $\pi$ around an optical axis of the erase light so as to produce a first-order Bessel beam.

13. The double-resonance absorption microscope of claim 12, wherein said phase modulation means comprises a substrate transparent and optically flat with respect to the erase light, and comprises an optical thin film evaporated on said substrate such that said optical thin film has a thickness distribution for providing the erase light with the phase difference of $\pi$ around the optical axis of the erase light.

14. The double-resonance absorption microscope of claim 12, wherein said phase modulation means comprises a substrate transparent and optically flat with respect to the erase light, said substrate being etched so as to be operable to provide the erase light with the phase difference of $\pi$ around the optical axis of the erase light.

15. The double-resonance absorption microscope of claim 14, wherein said erase light source is operable to emit erase light having a pulse width wider than a pulse width of the pump light, said pump light source and said erase light source being operable to emit pump light and erase light, respectively, such that an irradiation duration of the pump light completely overlaps an irradiation duration of the erase light.

16. The double-resonance absorption microscope of claim 15, further comprising pulse width control means for widening the pulse width of the erase light so that the pulse width of the erase light is wider than the pulse width of the pump light.

17. The double-resonance absorption microscope of claim 16, wherein said pulse width control means comprises a pulse stretcher optical system including:
- a half mirror for providing light separation; and
- a reflection optical system for forming a loop optical path including said half mirror thereon.

18. The double-resonance absorption microscope of claim 15, further comprising an irradiation timing control means for controlling a timing of the pump light and the erase light reaching the sample molecule so that an irradiation duration of the pump light completely overlaps an irradiation duration of the erase light.

19. The double-resonance absorption microscope of claim 18, wherein said irradiation timing control means is operable to control an optical path difference of the pump light and the erase light so as to control the timing of the pump light and the erase light reaching the sample molecule.

20. The double-resonance absorption microscope of claim 18, wherein said pump light source comprises a pump light pulse laser and said erase light source comprises an erase light pulse laser independent of said pump light pulse laser, said irradiation timing control means being operable to control a Q-switch of each of said pump light pulse laser and said erase light pulse laser so as to control the timing of the pump light and the erase light reaching the sample molecule.

21. The double-resonance absorption microscope of claim 12, wherein a sample is dyed with a fluorescent labeler molecule having at least three electronic states including a ground state, the sample molecule comprising the fluorescent labeler molecule.

22. The double-resonance absorption microscope of claim 12, wherein at least one of said pump light source and said erase light source comprises a solid dye laser including:
- a solid laser medium wherein a dye molecule having more than two quantum levels is dispersed; and
- a short pulse laser for exciting said solid laser medium.

* * * * *